(12) United States Patent
Lançois et al.

(10) Patent No.: US 11,708,369 B2
(45) Date of Patent: Jul. 25, 2023

(54) HETEROAROMATIC COMPOUNDS HAVING ACTIVITY AGAINST RSV

(71) Applicant: Janssen Sciences Ireland Unlimited Company, County Cork (IE)

(72) Inventors: David Francis Alain Lançois, Louviers (FR); Jérome Émile Georges Guillemont, Andé, FL (US); Pierre Jean-Marie Bernard Raboisson, Wavre (BE); Peter Rigaux, Overijse (BE); Antoine Benjamin Michaut, Le Vaudreuil (FR); Sabrina Dany France Quatrevaux, Cléon (FR); Sovy Chao, Villers-le-lac (FR); Dirk André Emmy Roymans, Turnhout (BE)

(73) Assignee: Janssen Sciences Ireland Unlimited Company, County Cork (IE)

( * ) Notice: Subject to any disclaimer, the term of this patent is extended or adjusted under 35 U.S.C. 154(b) by 0 days.

(21) Appl. No.: 17/050,419

(22) PCT Filed: Apr. 19, 2019

(86) PCT No.: PCT/EP2019/060216
§ 371 (c)(1),
(2) Date: Oct. 23, 2020

(87) PCT Pub. No.: WO2019/206828
PCT Pub. Date: Oct. 31, 2019

(65) Prior Publication Data
US 2021/0094958 A1 Apr. 1, 2021

(30) Foreign Application Priority Data
Apr. 23, 2018 (EP) .................... 18168671

(51) Int. Cl.
*A61K 31/437* (2006.01)
*A61K 31/4353* (2006.01)
*C07D 487/04* (2006.01)
*C07D 417/04* (2006.01)

(52) U.S. Cl.
CPC ................. *C07D 487/04* (2013.01)

(58) Field of Classification Search
CPC .............. A61K 31/437; A61K 31/4353; C07D 4877/04; C07D 471/04
USPC ........ 514/259.3, 259.31, 300, 303; 544/282; 546/121
See application file for complete search history.

(56) References Cited

U.S. PATENT DOCUMENTS

| | | |
|---|---|---|
| 5,972,966 A | 10/1999 | deSolms |
| 5,977,134 A | 11/1999 | Ciccarone et al. |
| 6,177,443 B1 | 1/2001 | Madsen et al. |
| 6,218,404 B1 | 4/2001 | Bigge et al. |
| 6,608,203 B2 | 8/2003 | Cameron et al. |
| 6,765,096 B1 | 7/2004 | Aono et al. |
| 6,919,376 B2 | 7/2005 | Llompart et al. |
| 7,507,842 B2 | 3/2009 | Oehler et al. |
| 7,642,272 B2 | 1/2010 | Shankar et al. |
| 7,662,826 B2 | 2/2010 | Seno et al. |
| 7,893,096 B2 | 2/2011 | Valiante, Jr. |
| 8,450,343 B2 | 5/2013 | Huang et al. |
| 8,691,938 B2 | 4/2014 | DeGoey et al. |
| 8,829,027 B2 | 9/2014 | Eckhardt et al. |
| 8,946,238 B2 | 2/2015 | Boojamra et al. |
| 10,208,048 B2 | 2/2019 | Lançois |
| 10,611,769 B2 | 4/2020 | Lançois |
| 2003/0073681 A1 | 4/2003 | Hauske et al. |
| 2010/0063047 A1 | 3/2010 | Borchardt et al. |
| 2010/0204265 A1 | 8/2010 | Baskaran et al. |
| 2013/0164280 A1 | 6/2013 | Boojamra et al. |

FOREIGN PATENT DOCUMENTS

| | | |
|---|---|---|
| CN | 105777632 A | 7/2016 |
| WO | 199619483 A1 | 6/1996 |
| WO | 199701275 A1 | 1/1997 |
| WO | 2004029042 A1 | 4/2004 |
| WO | 2004037817 A1 | 6/2004 |
| WO | 2005000315 A1 | 1/2005 |
| WO | 2005035516 A1 | 4/2005 |
| WO | 2005042530 A1 | 5/2005 |
| WO | 2005058871 A1 | 6/2005 |
| WO | 2005061513 A1 | 7/2005 |
| WO | 2006030925 A1 | 3/2006 |
| WO | 2006034341 A2 | 3/2006 |
| WO | 2006136561 A1 | 12/2006 |
| WO | 2007044085 A2 | 4/2007 |
| WO | 2007060409 A1 | 5/2007 |
| WO | 2008063671 A2 | 5/2008 |
| WO | 2009/023179 A2 | 2/2009 |
| WO | 2010104306 A2 | 9/2010 |
| WO | 2010111058 A1 | 9/2010 |
| WO | 2011163518 A1 | 12/2011 |

(Continued)

OTHER PUBLICATIONS

Jordan, V. C. Nature Reviews: Drug Discovery, 2, 2003, 205.*

(Continued)

*Primary Examiner* — Douglas M Willis

(57) ABSTRACT

The invention concerns compounds of formula (I) having antiviral activity, in particular, having an inhibitory activity on the replication of the respiratory syncytial virus (RSV). The invention further concerns pharmaceutical compositions comprising these compounds and the compounds for use in the treatment of respiratory syncytial virus infection.

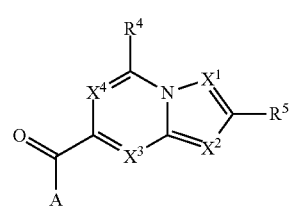

(I)

20 Claims, No Drawings

(56) References Cited

FOREIGN PATENT DOCUMENTS

| WO | 2012051361 | A1 | | 4/2012 | |
|---|---|---|---|---|---|
| WO | 2013158776 | A1 | | 10/2013 | |
| WO | 2015042297 | A1 | | 3/2015 | |
| WO | 2015106025 | A1 | | 7/2015 | |
| WO | 2016017980 | A1 | | 2/2016 | |
| WO | 2016071293 | A2 | | 5/2016 | |
| WO | 2016/091774 | | | 6/2016 | |
| WO | 2016/174079 | A1 | | 11/2016 | |
| WO | 2016174079 | A1 | | 11/2016 | |
| WO | 2019106004 | A1 | | 6/2019 | |
| WO | 2019149734 | A1 | | 8/2019 | |
| WO | 2019206828 | A1 | | 10/2019 | |
| WO | WO-2019206828 | A1 | * | 10/2019 | ......... A61K 31/4725 |
| WO | 2020109224 | | | 6/2020 | |
| WO | 2020234333 | A1 | | 11/2020 | |

OTHER PUBLICATIONS

Dörwald, F. Zaragoza. Side Reactions in Organic Synthesis: A Guide to Successful Synthesis Design, Weinheim: WILEY-VCH Verlag GmbH & Co. KGaA, 2005, Preface.*

Hallack et al., "Glycosaminoglycan Sulfation Requirements for Respiratory Syncytial Virus Infection," Journal of Virology, vol. 74(22):pp. 10508-10513 (Nov. 2000).

Wyde et al., "CL387626 exhibits marked and unusual antiviral activity against respiratory syncytial virus in tissue culture and in cotton rats", Antiviral Research, vol. 38: pp. 31-42 (1998).

International Search Report and Written Opinion dated May 17, 2019 for International Patent Application No. PCT/EP2019/060216.

Herr et al. 5-subsituted-1H-tetrazoles as carboxylic acid isosteres: Medicinal Chemistry and Synthetic Methods, Bioorganic & Medicinal Chemistry, 2002, vol. 10, pp. 3379-3393, Feb. 3, 2015.

* cited by examiner

HETEROAROMATIC COMPOUNDS HAVING ACTIVITY AGAINST RSV

CROSS-REFERENCE TO RELATED APPLICATIONS

This application is a national phase entry of International Application No. PCT/EP2019/060216, filed on Apr. 19, 2019, which claims priority to EP Patent Application No. 18168671.8, filed on Apr. 23, 2018, each of which is incorporated herein in its entirety.

FIELD OF THE INVENTION

The invention concerns compounds having antiviral activity, in particular having an inhibitory activity on the replication of the respiratory syncytial virus (RSV). The invention further concerns pharmaceutical compositions comprising these compounds and the compounds for use in the treatment of respiratory syncytial virus infection.

BACKGROUND

Human RSV or Respiratory Syncytial Virus is a large RNA virus, member of the family of Pneumoviridae, genus Orthopneumovirus together with bovine RSV virus. Human RSV is responsible for a spectrum of respiratory tract diseases in people of all ages throughout the world. It is the major cause of lower respiratory tract illness during infancy and childhood. Over half of all infants encounter RSV in their first year of life, and almost all within their first two years. The infection in young children can cause lung damage that persists for years and may contribute to chronic lung disease in later life (chronic wheezing, asthma). Older children and adults often suffer from a (bad) common cold upon RSV infection. In old age, susceptibility again increases, and RSV has been implicated in a number of outbreaks of pneumonia in the aged resulting in significant mortality.

Infection with a virus from a given subgroup does not protect against a subsequent infection with an RSV isolate from the same subgroup in the following winter season. Re-infection with RSV is thus common, despite the existence of only two subtypes, A and B.

Today only two drugs have been approved for use against RSV infection. A first one is ribavirin, a nucleoside analogue that provides an aerosol treatment for serious RSV infection in hospitalized children. The aerosol route of administration, the toxicity (risk of teratogenicity), the cost and the highly variable efficacy limit its use. Synagis® (palivizumab a monoclonal antibody, is used for passive immunoprophylaxis. Although the benefit of Synagis® has been demonstrated, the treatment is expensive, requires parenteral administration and is restricted to children at risk for developing severe pathology.

Clearly there is a need for an efficacious non-toxic and easy to administer drug against RSV replication. It would be particularly preferred to provide drugs against RSV replication that could be administered perorally.

Compounds that exhibit anti-RSV activity are disclosed in WO-2016/174079 and WO-2011/163518.

DETAILED DESCRIPTION OF THE INVENTION

The present invention relates to compounds of formula (I)

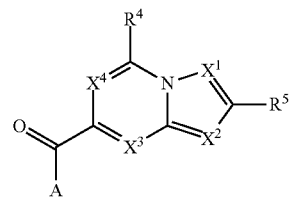

including any stereochemically isomeric form thereof, wherein
A is

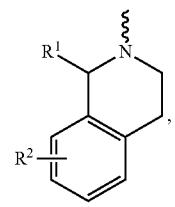

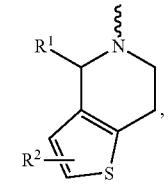

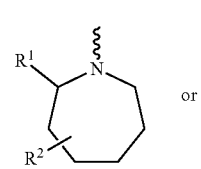

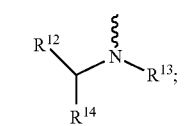

$R^5$ is

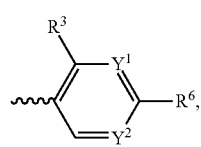

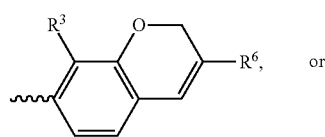

(b-3)

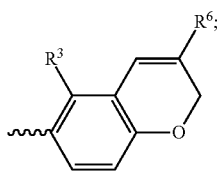

X$^1$, X$^2$, X$^3$ and X$^4$ are selected from X$^1$ is CH, X$^2$ is CH, X$^3$ is CH and X$^4$ is CH;
or X$^1$ is N, X$^2$ is CH, X$^3$ is CH and X$^4$ is CH,
or X$^1$ is CH, X$^2$ is N, X$^3$ is CH and X$^4$ is CH,
or X$^1$ is N, X$^2$ is CH, X$^3$ is CH and X$^4$ is N,
or X$^1$ is N, X$^2$ is N, X$^3$ is CH and X$^4$ is CH, and
or X$^1$ is CH, X$^2$ is N, X$^3$ is N and X$^4$ is CH,
wherein each CH is optionally substituted with halo, C$_{1-4}$alkyl or C$_{1-4}$alkyloxy;
Y$^1$ and Y$^2$ are each independently selected from CH, CF and N;
R$^1$ is CH$_3$ or CH$_2$CH$_3$;
R$^2$ is hydrogen, halo or C$_{1-4}$alkyl;
R$^{12}$ is C$_{1-2}$alkyl;
R$^{13}$ and R$^{14}$ are each independently selected from C$_{1-6}$alkyl;
R$^3$ is halo;
R$^4$ is C$_{1-6}$alkyl; C$_{3-6}$cycloalkyl; di(C$_{1-4}$alkyl)amino, pyrrolidinyl, Heteroaryl$^1$; C$_{1-4}$alkyl substituted with Heteroaryl$^1$; phenyl; phenyl substituted with 1, 2 or 3 substituents each individually selected from halo, hydroxy, cyano, C$_{1-4}$alkyl, polyhaloC$_{1-4}$alkyl, and C$_{1-4}$alkyloxy;
R$^6$ is C$_{2-6}$alkenyl substituted with one or two substituents selected from C$_{1-6}$alkyl, —(CO)—OR$^7$ or —(CO)—NR$^8$R$^9$; or
—NR$^9$—(CO)-Heterocycle wherein said Heterocycle is substituted with one or two substituents each independently selected from halo, hydroxy of C$_{1-4}$alkyloxy; or C$_{3-6}$cycloalkyl or Heterocycle, wherein said C$_{3-6}$cycloalkyl and Heterocycle is substituted with one or two substituents each independently selected from
C$_{1-6}$alkyl;
C$_{1-6}$alkyl substituted with one, two or three substituents each independently selected from halo, hydroxy, hydroxycarbonyl, aminocarbonyl, C$_{3-6}$cycloalkyl, C$_{3-6}$cycloalkyl substituted with one or two substituents each independently selected from C$_{1-4}$alkyl, halo, hydroxycarbonyl, and C$_{1-4}$alkyl substituted with hydroxycarbonyl;
C$_{3-6}$alkenyl;
C$_{3-6}$alkenyl substituted with one or two substituents selected from C$_{1-6}$alkyl, hydroxy, —(CO)—OR$^7$ or —(CO)—NR$^8$R$^9$;
hydroxy;
cyano;
—(CO)—O—R$^7$;
—(CO)—NR$^{10}$R$^{11}$;
—(CO)—NR$^9$—SO$_2$—R$^8$;
—(CO)—NR$^9$—(CO)—SO$_2$—R$^8$;
—O—(CO)—NR$^{10}$R$^{11}$;
—NR$^8$R$^9$;
—NR$^9$—(CO)—C$_{1-4}$alkyl;
—NR$^9$—(CO)—C$_{3-6}$cycloalkyl;
—NR$^9$—(CO)—O—R$^8$;
—NR$^9$—(CO)—NR$^9$—R$^8$;
—NR$^9$—SO$_2$—R$^8$;
—SO$_2$—R$^8$;
—SO$_2$—NR$^{10}$R$^{11}$; or
—SO$_2$—NR$^9$—(CO)—R$^8$.
Heteroaryl$^2$;

wherein
R$^7$ is hydrogen, or C$_{1-4}$alkyl;
R$^8$ is C$_{1-4}$alkyl, polyhaloC$_{1-4}$alkyl, or C$_{3-6}$cycloalkyl;
each R$^9$ is independently selected from hydrogen or C$_{1-4}$alkyl;
R$^{10}$ and R$^{11}$ are each independently selected from hydrogen; CN; C$_{1-4}$alkyl; C$_{3-6}$alkenyl; polyhaloC$_{1-4}$alkyl; C$_{3-6}$cycloalkyl; C$_{3-6}$cycloalkyl substituted with C$_{1-4}$alkyl; or C$_{1-4}$alkyl substituted with hydroxy or cyano;
Heterocycle is azetidinyl, pyrrolodinyl, piperidinyl, or homopiperidinyl;
Heteroaryl$^1$ is thienyl, pyridinyl or pyrimidinyl, wherein each Heteroaryl$^1$ is optionally substituted with one or two substituents each independently selected from C$_{1-4}$alkyl, halo, amino, and aminocarbonyl;
Heteroaryl$^2$ is pyrrolyl, pyrazolyl or thiazolyl; wherein each Heteroaryl$^2$ is optionally substituted with one or two substituents each independently selected from C$_{1-4}$alkyl, halo, —(CO)—OR$^7$ or —(CO)—NR$^8$R$^9$;
or a pharmaceutically acceptable acid addition salt thereof.
As used in the foregoing definitions:
halo is generic to fluoro, chloro, bromo and iodo;
C$_{1-4}$alkyl defines straight and branched chain saturated hydrocarbon radicals having from 1 to 4 carbon atoms such as, for example, methyl, ethyl, propyl, butyl, 1-methylethyl, 2-methyl-propyl and the like;
C$_{1-6}$alkyl is meant to include C$_{1-4}$alkyl and the higher homologues thereof having 5 or 6 carbon atoms, such as, for example, 2 methylbutyl, pentyl, hexyl and the like;
C$_{2-6}$alkenyl defines bivalent straight or branched chain hydrocarbon radicals containing from 2 to 6 carbon atoms such as, for example, 1,2-ethanediyl, 1,3-propanediyl, 1,4-butanediyl, 1,5-pentanediyl, 1,6-hexanediyl, and the branched isomers thereof;
C$_{3-6}$alkenyl defines straight and branched chain hydrocarbon radicals containing one double bond and having from 3 to 6 carbon atoms such as, for example, 2-propenyl, 3-butenyl, 2-butenyl, 2-pentenyl, 3-pentenyl, 3-methyl-2-butenyl, 3-hexenyl, 2-hexenyl and the like;
C$_{3-6}$cycloalkyl is generic to cyclopropyl, cyclobutyl, cyclopentyl, and cyclohexyl;
polyhaloC$_{1-4}$alkyl is defined as polyhalosubstituted C$_{1-4}$alkyl, in particular C$_{1-4}$alkyl (as hereinabove defined) substituted with 2 to 6 halogen atoms such as difluoromethyl, trifluoromethyl, trifluoroethyl, and the like;
—(CO)— or (CO) means carbonyl.
The term "compounds of the invention" as used herein, is meant to include the compounds of formula (I), and the salts and solvates thereof.
As used herein, any chemical formula with bonds shown only as solid lines and not as solid wedged or hashed wedged bonds, or otherwise indicated as having a particular configuration (e.g. R, S) around one or more atoms, contemplates each possible stereoisomer, or mixture of two or more stereoisomers.
Hereinbefore and hereinafter, the terms "compound of formula (I)" and "intermediates of synthesis of formula (I)" are meant to include the stereoisomers thereof and the tautomeric forms thereof.
The terms "stereoisomers", "stereoisomeric forms" or "stereochemically isomeric forms" hereinbefore or hereinafter are used interchangeably.

The invention includes all stereoisomers of the compounds of the invention either as a pure stereoisomer or as a mixture of two or more stereoisomers. Enantiomers are stereoisomers that are non-superimposable mirror images of each other. A 1:1 mixture of a pair of enantiomers is a racemate or racemic mixture. Diastereomers (or diastereoisomers) are stereoisomers that are not enantiomers, i.e. they are not related as mirror images. If a compound contains a double bond, the substituents may be in the E or the Z configuration. Substituents on bivalent cyclic (partially) saturated radicals may have either the cis- or trans-configuration; for example if a compound contains a disubstituted cycloalkyl group, the substituents may be in the cis or trans configuration.

The term "stereoisomers" also includes any rotamers, also called conformational isomers, the compounds of formula (I) may form.

Therefore, the invention includes enantiomers, diastereomers, racemates, E isomers, Z isomers, cis isomers, trans isomers, rotamers, and mixtures thereof, whenever chemically possible.

The meaning of all those terms, i.e. enantiomers, diastereomers, racemates, E isomers, Z isomers, cis isomers, trans isomers and mixtures thereof are known to the skilled person.

The absolute configuration is specified according to the Cahn-Ingold-Prelog system. The configuration at an asymmetric atom is specified by either R or S. Resolved stereoisomers whose absolute configuration is not known can be designated by (+) or (−) depending on the direction in which they rotate plane polarized light. For instance, resolved enantiomers whose absolute configuration is not known can be designated by (+) or (−) depending on the direction in which they rotate plane polarized light.

When a specific stereoisomer is identified, this means that said stereoisomer is substantially free, i.e. associated with less than 50%, preferably less than 20%, more preferably less than 10%, even more preferably less than 5%, in particular less than 2% and most preferably less than 1%, of the other stereoisomers. Thus, when a compound of formula (I) is for instance specified as (R), this means that the compound is substantially free of the (S) isomer; when a compound of formula (I) is for instance specified as E, this means that the compound is substantially free of the Z isomer; when a compound of formula (I) is for instance specified as cis, this means that the compound is substantially free of the trans isomer.

Some of the compounds according to formula (I) may also exist in their tautomeric form. Such forms in so far as they may exist, although not explicitly indicated in the above formula (I) are intended to be included within the scope of the present invention.

It follows that a single compound may exist in both stereoisomeric and tautomeric form.

Atropisomers (or atropoisomers) are stereoisomers which have a particular spatial configuration, resulting from a restricted rotation about a single bond, due to large steric hindrance. All atropisomeric forms of the compounds of Formula (I) are intended to be included within the scope of the present invention.

The pharmaceutically acceptable acid addition salts as mentioned hereinabove are meant to comprise the therapeutically active non-toxic acid addition salt forms that the compounds of formula (I) are able to form. These pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids.

Conversely said salt forms can be converted by treatment with an appropriate base into the free base form.

The compounds of formula (I) may exist in both unsolvated and solvated forms. The term 'solvate' is used herein to describe a molecular association comprising a compound of the invention and one or more pharmaceutically acceptable solvent molecules, e.g. water or ethanol. The term 'hydrate' is used when said solvent is water.

For the avoidance of doubt, compounds of formula (I) may contain the stated atoms in any of their natural or non-natural isotopic forms. In this respect, embodiments of the invention that may be mentioned include those in which (a) the compound of formula (I) is not isotopically enriched or labelled with respect to any atoms of the compound; and (b) the compound of formula (I) is isotopically enriched or labelled with respect to one or more atoms of the compound. Compounds of formula (I) that are isotopically enriched or labelled (with respect to one or more atoms of the compound) with one or more stable isotopes include, for example, compounds of formula (I) that are isotopically enriched or labelled with one or more atoms such as deuterium, $^{13}C$, $^{14}C$, $^{14}N$, $^{15}O$ or the like.

A first group of compounds are compounds of formula (I) wherein $X^1$ is CH, $X^2$ is CH, $X^3$ is CH and $X^4$ is CH.

A second group of compounds are compounds of formula (I) wherein $X^1$ is N, $X^2$ is CH, $X^3$ is CH and $X^4$ is CH.

A third group of compounds are compounds of formula (I) wherein $X^1$ is CH, $X^2$ is N, $X^3$ is CH and $X^4$ is CH.

A fourth group of compounds are compounds of formula (I) wherein $X^1$ is N, $X^2$ is CH, $X^3$ is CH and $X^4$ is N.

A fifth group of compounds are compounds of formula (I) wherein $X^1$ is N, $X^2$ is N, $X^3$ is CH and $X^4$ is CH.

A sixth group of compounds are compounds of formula (I) wherein $X^1$ is CH, $X^2$ is N, $X^3$ is N and $X^4$ is CH.

A seventh group of compound are compounds of formula (I) wherein radical A is of formula (a-1).

An eight group of compound are compounds of formula (I) wherein radical A is of formula (a-2).

A ninth group of compound are compounds of formula (I) wherein $R^4$ is $C_{3-6}$cycloalkyl.

A tenth group of compound are compounds of formula (I) wherein $R^5$ is of formula (b-1) wherein $Y^1$ and $Y^2$ are CH.

Interesting compounds of formula (I) are those compounds of formula (I) wherein one or more of the following restrictions apply:

a) A is a radical of formula (a-1); or
b) A is a radical of formula (a-2); or
c) $R^1$ is methyl; or
d) $R^2$ is hydrogen; or
e) $R^3$ is fluoro; or
f) $R^4$ is $C_{3-6}$cycloalkyl, in particular cyclopropyl; or
g) $R^4$ is $C_{1-4}$alkyl, in particular ethyl; or
h) $R^4$ is Heteroaryl$^1$ wherein Heteroaryl$^1$ is pyridinyl; or
i) $R^5$ is of formula (b-1) wherein $Y^1$ and $Y^2$ are CH and $R^3$ is halo, in particular $R^3$ is fluoro; and
j) $R^6$ is $C_{3-6}$cycloalkyl or pyrrolidinyl, wherein said $C_{3-6}$cycloalkyl or pyrrolidinyl are substituted with one or two substituents each independently selected from —(CO)—O—$R^7$ or —(CO)—$NR^{10}R^{11}$.

In general compounds of formula (I) can be prepared by reacting an intermediate of formula (II) with an alkylboronate intermediate of formula (III) in at least one reaction-inert solvent and optionally in the presence of at least one transition metal coupling reagent and/or at least one suitable ligand, the said process further optionally comprising converting a compound of formula (I) into an addition salt thereof. Suitable metal coupling reagents and/or suitable ligands for this reaction are, e.g. palladium compounds such as palladium tetra(triphenylphosphine), tris(dibenzylideneacetone dipalladium, 2,2'-bis(diphenylphosphino)-1,1'-binapthyl and the like.

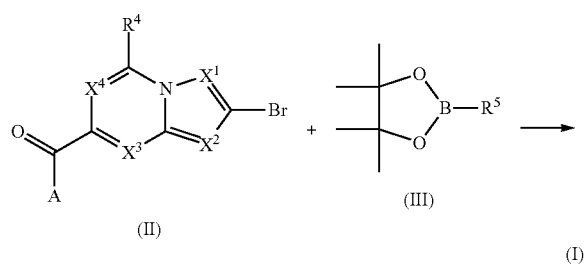

Compounds of formula (I-a), defined as compounds of formula (I) wherein $R^5$ is of formula (b-1), can also be prepared by reacting an intermediate of formula (IV) with either an intermediate of formula (V), (VI) or (VII) in a reaction-inert solvent and optionally in the presence of at least one transition metal coupling reagent and/or at least one suitable ligand, the said process further optionally comprising converting a compound of formula (I) into an addition salt thereof.

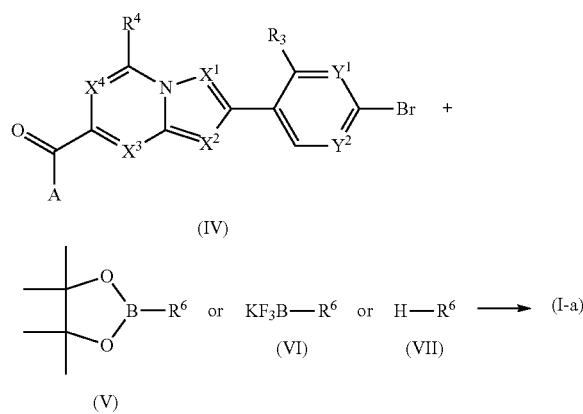

Other synthetic pathways for preparing compounds of formula (I) have been described in the experimental party as general methods of preparation and specific working examples.

The compounds of formula (I) may further be prepared by converting compounds of formula (I) into each other according to art-known group transformation reactions.

The starting materials and some of the intermediates are known compounds and are commercially available or may be prepared according to conventional reaction procedures generally known in the art.

The compounds of formula (I) as prepared in the hereinabove described processes may be synthesized in the form of racemic mixtures of enantiomers which can be separated from one another following art-known resolution procedures. Those compounds of formula (I) that are obtained in racemic form may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials.

The compounds of formula (I) show antiviral properties. Viral infections treatable using the compounds and methods of the present invention include those infections brought on by ortho- and paramyxoviruses and in particular by human and bovine respiratory syncytial virus (RSV). A number of the compounds of this invention moreover are active against mutated strains of RSV. Additionally, many of the compounds of this invention show a favorable pharmacokinetic profile and have attractive properties in terms of bioavailability, including an acceptable half-life, AUC and peak values and lacking unfavourable phenomena such as insufficient quick onset and tissue retention.

The in vitro antiviral activity against RSV of the present compounds was tested in a test as described in the experimental part of the description, and may also be demonstrated in a virus yield reduction assay. The in vivo antiviral activity against RSV of the present compounds may be demonstrated in a test model using cotton rats as described in Wyde et al. in Antiviral Research, 38, p. 31-42 (1998).

Additionally the present invention provides pharmaceutical compositions comprising at least one pharmaceutically acceptable carrier and a therapeutically effective amount of a compound of formula (I). Also provided are pharmaceutical compositions comprising a pharmaceutically acceptable carrier, a therapeutically active amount of a compound of formula (I), and another antiviral agent, in particular a RSV inhibiting compound.

In order to prepare the pharmaceutical compositions of this invention, an effective amount of the particular compound, in base or acid addition salt form, as the active ingredient is combined in intimate admixture with at least one pharmaceutically acceptable carrier, which carrier may take a wide variety of forms depending on the form of preparation desired for administration. These pharmaceutical compositions are desirably in unitary dosage form suitable, preferably, for oral administration, rectal administration, percutaneous administration or parenteral injection.

For example in preparing the compositions in oral dosage form, any of the usual liquid pharmaceutical carriers may be employed, such as for instance water, glycols, oils, alcohols and the like in the case of oral liquid preparations such as suspensions, syrups, elixirs and solutions; or solid pharmaceutical carriers such as starches, sugars, kaolin, lubricants, binders, disintegrating agents and the like in the case of powders, pills, capsules and tablets. Because of their easy administration, tablets and capsules represent the most advantageous oral dosage unit form, in which case solid pharmaceutical carriers are obviously employed. For parenteral injection compositions, the pharmaceutical carrier will mainly comprise sterile water, although other ingredients may be included in order to improve solubility of the active ingredient. Injectable solutions may be prepared for instance by using a pharmaceutical carrier comprising a saline solution, a glucose solution or a mixture of both. Injectable suspensions may also be prepared by using appropriate liquid carriers, suspending agents and the like. In compositions suitable for percutaneous administration, the pharmaceutical carrier may optionally comprise a penetration enhancing agent and/or a suitable wetting agent, optionally combined with minor proportions of suitable additives which do not cause a significant deleterious effect to the skin. Said additives may be selected in order to facilitate administration of the active ingredient to the skin and/or be helpful for preparing the desired compositions. These topical compositions may be administered in various ways, e.g., as a transdermal patch, a spot-on or an ointment. Addition salts of the compounds of formula (I), due to their increased water solubility over the corresponding base form, are obviously more suitable in the preparation of aqueous compositions.

It is especially advantageous to formulate the pharmaceutical compositions of the invention in dosage unit form for ease of administration and uniformity of dosage. "Dosage unit form" as used herein refers to physically discrete units suitable as unitary dosages, each unit containing a predetermined amount of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

For oral administration, the pharmaceutical compositions of the present invention may take the form of solid dose forms, for example, tablets (both swallowable and chewable forms), capsules or gelcaps, prepared by conventional means with pharmaceutically acceptable excipients and carriers such as binding agents (e.g. pregelatinised maize starch, polyvinylpyrrolidone, hydroxypropylmethylcellulose and the like), fillers (e.g. lactose, microcrystalline cellulose, calcium phosphate and the like), lubricants (e.g. magnesium stearate, talc, silica and the like), disintegrating agents (e.g. potato starch, sodium starch glycollate and the like), wetting agents (e.g. sodium laurylsulphate) and the like. Such tablets may also be coated by methods well known in the art.

Liquid preparations for oral administration may take the form of e.g. solutions, syrups or suspensions, or they may be formulated as a dry product for admixture with water and/or another suitable liquid carrier before use. Such liquid preparations may be prepared by conventional means, optionally with other pharmaceutically acceptable additives such as suspending agents (e.g. sorbitol syrup, methylcellulose, hydroxypropylmethylcellulose or hydrogenated edible fats), emulsifying agents (e.g. lecithin or acacia), non aqueous carriers (e.g. almond oil, oily esters or ethyl alcohol), sweeteners, flavours, masking agents and preservatives (e.g. methyl or propyl p-hydroxybenzoates or sorbic acid).

Pharmaceutically acceptable sweeteners useful in the pharmaceutical compositions of the invention comprise preferably at least one intense sweetener such as aspartame, acesulfame potassium, sodium cyclamate, alitame, a dihydrochalcone sweetener, monellin, stevioside sucralose (4,1', 6'-trichloro-4,1',6'-trideoxygalactosucrose) or, preferably, saccharin, sodium or calcium saccharin, and optionally at least one bulk sweetener such as sorbitol, mannitol, fructose, sucrose, maltose, isomalt, glucose, hydrogenated glucose syrup, xylitol, caramel or honey. Intense sweeteners are conveniently used in low concentrations. For example, in the case of sodium saccharin, the said concentration may range from about 0.04% to 0.1% (weight/volume) of the final formulation. The bulk sweetener can effectively be used in larger concentrations ranging from about 10% to about 35%, preferably from about 10% to 15% (weight/volume).

The pharmaceutically acceptable flavours which can mask the bitter tasting ingredients in the low-dosage formulations are preferably fruit flavours such as cherry, raspberry, black currant or strawberry flavour. A combination of two flavours may yield very good results. In the high-dosage formulations, stronger pharmaceutically acceptable flavours may be required such as Caramel Chocolate, Mint Cool, Fantasy and the like. Each flavour may be present in the final composition in a concentration ranging from about 0.05% to 1% (weight/volume).

Combinations of said strong flavours are advantageously used. Preferably a flavour is used that does not undergo any change or loss of taste and/or color under the circumstances of the formulation.

The compounds of formula (I) may be formulated for parenteral administration by injection, conveniently intravenous, intra-muscular or subcutaneous injection, for example by bolus injection or continuous intravenous infusion. Formulations for injection may be presented in unit dosage form, e.g. in ampoules or multi-dose containers, including an added preservative. They may take such forms as suspensions, solutions or emulsions in oily or aqueous vehicles, and may contain formulating agents such as isotonizing, suspending, stabilizing and/or dispersing agents. Alternatively, the active ingredient may be present in powder form for mixing with a suitable vehicle, e.g. sterile pyrogen free water, before use.

The compounds of formula (I) may also be formulated in rectal compositions such as suppositories or retention enemas, e.g. containing conventional suppository bases such as cocoa butter and/or other glycerides.

In general it is contemplated that an antivirally effective daily amount would be from 0.01 mg/kg to 500 mg/kg body weight, more preferably from 0.1 mg/kg to 50 mg/kg body weight. It may be appropriate to administer the required dose as two, three, four or more sub-doses at appropriate intervals throughout the day. Said sub-doses may be formulated as unit dosage forms, for example, containing 1 to 1000 mg, and in particular 5 to 200 mg of active ingredient per unit dosage form.

The exact dosage and frequency of administration depends on the particular compound of formula (I) used, the particular condition being treated, the severity of the condition being treated, the age, weight, sex, extent of disorder and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention. The effective daily amount ranges mentioned hereinabove are therefore only guidelines.

Also, the combination of another antiviral agent and a compound of formula (I) can be used as a medicine. Thus, the present invention also relates to a product containing (a) a compound of formula (I), and (b) another antiviral compound, as a combined preparation for simultaneous, separate or sequential use in antiviral treatment. The different drugs may be combined in a single preparation together with pharmaceutically acceptable carriers. For instance, the compounds of the present invention may be combined with interferon-beta or tumor necrosis factor-alpha in order to treat or prevent RSV infections. Other antiviral compounds (b) to be combined with a compound of formula (I) for use in the treatment of RSV are RSV fusion inhibitors or RSV polymerase inhibitors. Specific antiviral compounds for combination with any of the compounds of formula (I) that are useful in the treatment of RSV are the RSV inhibiting compounds selected from ribavirin, lumicitabine, presatovir, ALX-0171, MDT-637, BTA-9881, BMS-433771, YM-543403, A-60444, TMC-353121, RFI-641, CL-387626, MBX-300, 3-({5-chloro-1-[3-(methyl-sulfonyl)propyl]-1H-benzimidazol-2-yl}methyl)-1-cyclopropyl-1,3-dihydro-2H-imidazo[4,5-c]pyridin-2-one, 3-[[7-chloro-3-(2-ethylsulfonyl-ethyl)imidazo[1,2-a]pyridin-2-yl]methyl]-1-cyclopropyl-imidazo[4,5-c]pyridin-2-one, and 3-({5-chloro-1-[3-(methyl-sulfonyl)propyl]-1H-indol-2-yl}methyl)-1-(2,2,2-trifluoroethyl)-1,3-dihydro-2H-imidazo[4,5-c]pyridin-2-one.

Experimental Part

A. Abbreviations

| | |
|---|---|
| μw or MW | microwave |
| AcOH | acetic acid |
| aq. | aqueous |
| br | broad |
| cataCXium® A | di(1-adamantyl)-n-butylphosphine CAS [321921-71-5] |
| d | doublet |
| DCE | 1,2-dichloroethane |
| DCM | dichloromethane |
| DIPA | diisopropylamine |
| DIPEA | N,N-diisopropylethylamine |
| DMAP | 4-(dimethylamino)pyridine CAS [1122-58-3] |
| DME | 1,2-dimethoxyethane |
| DMF | dimethylformamide |
| DMSO | dimethyl sulfoxide |
| $Et_2O$ | diethyl ether |
| $Et_3N$ | triethylamine |
| EtOAc | ethyl acetate |
| EtOH | ethanol |
| h | hour |
| HATU | 1-[bis(dimethylamino)methylene]-1H-1,2,3-triazolo[4,5-b]pyridinium 3-oxid hexafluorophosphate CAS [148893-10-1] |
| i-PrMgCl | isopropylmagnesium chloride |
| KOAc | potassium acetate |
| LDA | lithium diisopropylamide |
| LiHMDS | lithium bis(trimethylsilyl)amide |
| m | multiplet |
| m/z | mass-to-charge ratio |
| MeCN | acetonitrile |
| MeMgBr | methylmagnesium bromide |
| $MeNH_2$ | methylamine |
| MeOH | methanol |
| Me—THF | 2-methyltetrahydrofuran CAS [96-47-9] |
| min | minute(s) |
| MTBE | tert-butyl methyl ether |
| NMR | Nuclear Magnetic Resonance |
| o/n | overnight |
| $P(Cy)_3$ | tricyclohexylphosphine CAS [2622-14-2] |
| $Pd(OAc)_2$ | palladium (II) acetate CAS [3375-31-3] |
| $PdCl_2$ | palladium(II) chloride CAS [7647-10-1] |
| $PdCl_2(dppf)$ | [1,1'-bis(diphenylphosphino)ferrocene]dichloropalladium(II) CAS [72287-26-4] |
| $PdCl_2(dppf)$•DCM | [1,1'-bis(diphenylphosphino)ferrocene]dichloropalladium(II), complex with dichloromethane CAS [95464-05-4] |
| $PdCl_2(dtbpf)$ | [1,1'-bis(di-tert-butylphosphino)ferrocene]dichloro-palladium(II) CAS [95408-45-0] |
| $(Ph)_2O$ | diphenyl ether |
| PPACA | propylphosphonic anhydride CAS [68957-94-8] |
| $PPh_3$ | triphenylphosphine |
| ppm | parts per million |
| q | quartet |
| quin | quintuplet |
| $Rh_2(OAc)_4$ | rhodium(II) acetate dimer CAS [15956-28-2] |
| rt | room temperature |
| s | singulet |
| Selectfluor® | 1-chloromethyl-4-fluoro-1,4-diazoniabicyclo[2.2.2]octane bis(tetrafluoroborate) CAS [140681-55-6] |
| sext | sextuplet |
| t | triplet |
| t-BuOK | potassium tert-butoxide |
| TFA | trifluoroacetic acid CAS [76-05-1] |
| TFAA | trifluoroacetic anhydride CAS [407-25-0] |
| THF | tetrahydrofuran |
| XantPhos | 4,5-bis(diphenylphosphino)-9,9-dimethylxanthene CAS [161265-03-8] |
| Δ | heat |

The stereochemical configuration for some compounds has been designated as R* or S* (or *R or *S) when the absolute stereochemistry is undetermined (even if the bonds are drawn stereospecifically) although the compound itself has been isolated as a single stereoisomer and is enantiomerically pure. This means that the absolute stereoconfiguration of the stereocentre indicated by * is undetermined (even if the bonds are drawn stereospecifically) although the compound is enantiomerically pure at the indicated centre.

B. Compound Synthesis

Indolizines

SYNTHESIS OF INTERMEDIATES

Synthesis of Intermediate A3

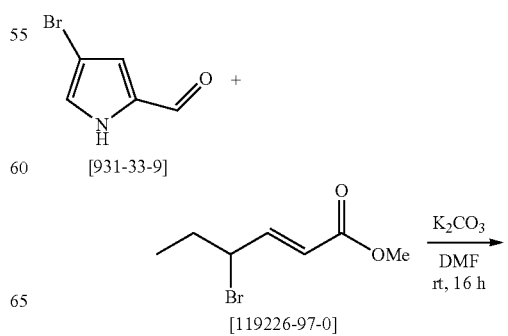

-continued

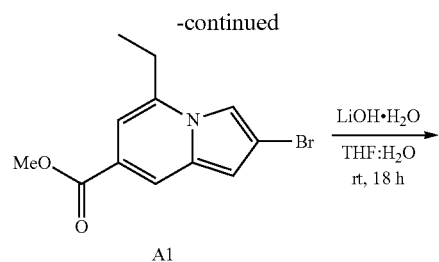

A1

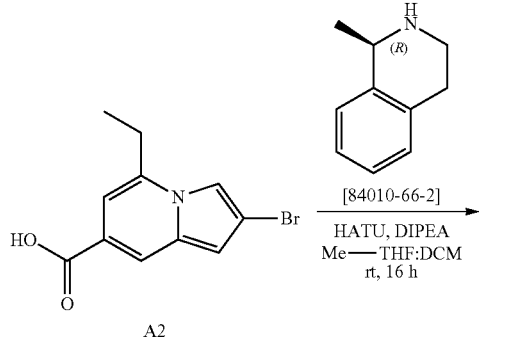

A3

Intermediate A1

Methyl 2-bromo-5-ethylindolizine-7-carboxylate

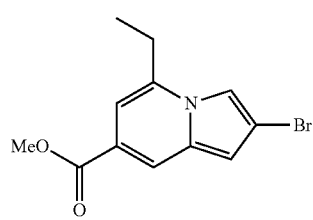

A1

A mixture of 4-bromo-1H-pyrrole-2-carbaldehyde [931-33-9] (1.41 g, 8.10 mmol), methyl-4-bromo-hex-2-enoate [119226-97-0] (2.26 g, 9.72 mmol, 89% purity) and potassium carbonate (2.46 g, 17.3 mmol) in DMF (38 mL) was stirred at rt for 16 h. The reaction mixture was poured out into water and the aqueous phase was extracted with EtOAc (twice). The combined organic extracts were washed with brine, dried over MgSO₄, filtered and the solvent was evaporated in vacuo. The crude mixture was purified by preparative LC (regular SiOH, 30 μm, 200 g Interchim®, dry loading (Celite®), mobile phase gradient: heptane/EtOAc from 100:0 to 50:50) to afford intermediate A1 (0.65 g, 28%).

Intermediate A2

2-Bromo-5-ethylindolizine-7-carboxylic Acid

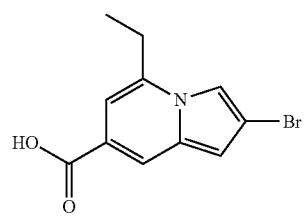

A2

A mixture of intermediate A1 (0.65 g, 2.30 mmol) and lithium hydroxide monohydrate (193 mg, 4.61 mmol) in THF (15 mL) and H₂O (5 mL) was stirred at rt for 16 h. An additional amount of lithium hydroxide monohydrate (97.0 mg, 2.30 mmol) was added and the reaction mixture was stirred at rt for a further 2 h. The reaction mixture was diluted with a 1N aqueous solution of HCl. The layers were separated and the aqueous phase was extracted with EtOAc (twice). The combined organic extracts were dried over MgSO₄, filtered and the solvent was evaporated in vacuo to afford intermediate A2 (617 mg, 95%).

Intermediate A3

(1R)-2-(2-Bromo-5-ethylindolizine-7-carbonyl)-1-methyl-1,2,3,4-tetrahydroisoquinoline

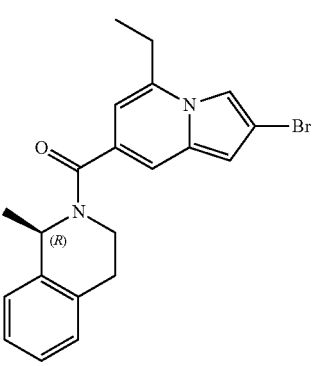

A3

To a mixture of intermediate A2 (617 mg, 2.19 mmol) and (1R)-1-methyl-1,2,3,4-tetrahydroisoquinoline [84010-66-2] (0.40 mL, 2.62 mmol) in 2-methyltetrahydrofuran (20 mL) were added HATU (1.66 g, 4.37 mmol) and DIPEA (1.51 mL, 8.76 mmol). The reaction mixture was stirred at rt for 16 h. DCM (5 mL) was added and the reaction mixture was stirred at rt for another 2 h. The precipitate was filtered off and the filtrate was evaporated to dryness. The crude mixture was purified by preparative LC (regular SiOH, 30 μm, 40 g Interchim®, liquid injection (DCM), mobile phase gradient: heptane/EtOAc from 80:20 to 40:60) to give intermediate A3 (700 mg, 81%).

Synthesis of Intermediate I1

Ethyl (1S,2S)-2-[3-fluoro-4-(tetramethyl-1,3,2-dioxaborolan-2-yl)phenyl]cyclopropane-1-carboxylate

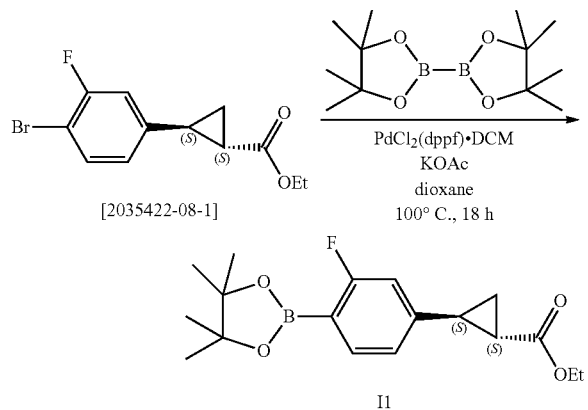

In a sealed tube bis(pinacolato)diboron (10.0 g, 39.4 mmol) and potassium acetate (6.80 g, 69.3 mmol) were added to a solution of ethyl (1S,2S)-2-(4-bromo-3-fluorophenyl)cyclopropane-1-carboxylate [2035422-08-1] (10.0 g, 34.8 mmol) in 1,4-dioxane (170 mL) under nitrogen atmosphere. The mixture was purged with nitrogen and [1,1'-bis(diphenylphosphino)ferrocene]dichloropalladium (II), complex with DCM (2.80 g, 3.42 mmol) was added. The reaction mixture was purged again with nitrogen and stirred at 100° C. for 18 h. The reaction mixture was diluted with EtOAc. The organic phase was washed with $H_2O$ and brine (twice), dried over $MgSO_4$, filtered and concentrated in vacuo. The crude mixture was purified by preparative LC (irregular SiOH, 15-40 μm, Merck 400 g, liquid injection (DCM), mobile phase gradient: heptane/EtOAc from 100:0 to 0:25) to afford intermediate I1 (9.26 g, 80%) as a colorless oil.

Synthesis of Final Compounds

Compound 1

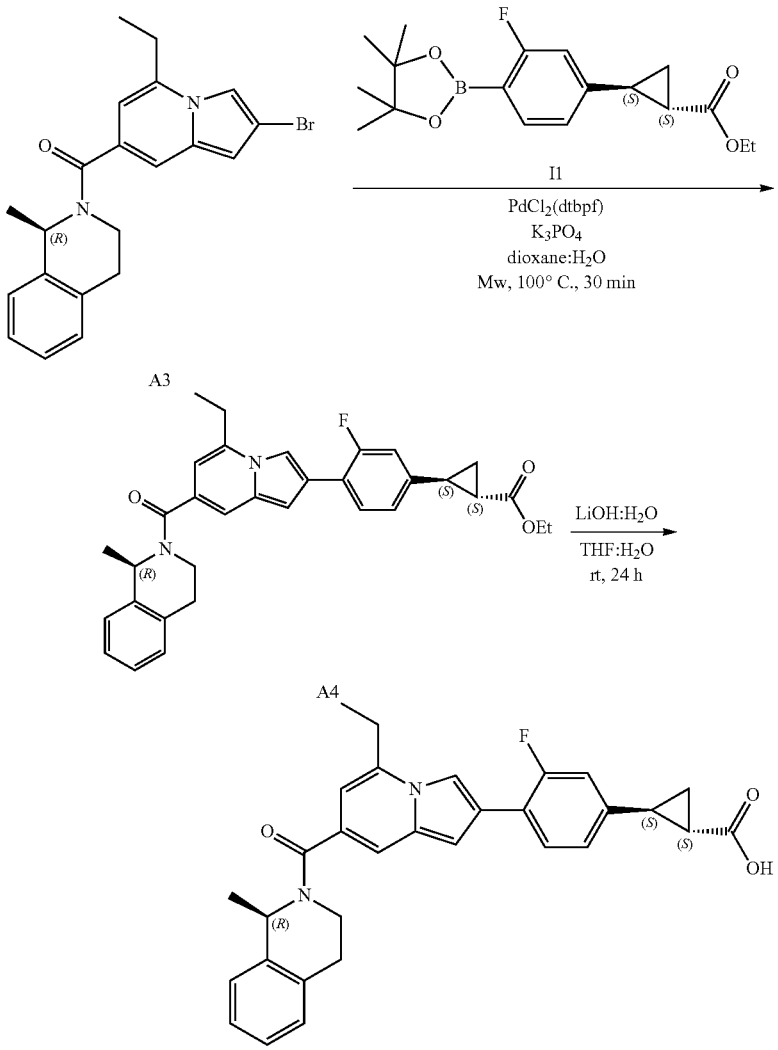

Intermediate A4

Ethyl (1S,2S)-2-(4-{5-ethyl-7-[(1R)-1-methyl-1,2,3,4-tetrahydroisoquinoline-2-carbonyl]indolizin-2-yl}-3-fluorophenyl)cyclopropane-1-carboxylate

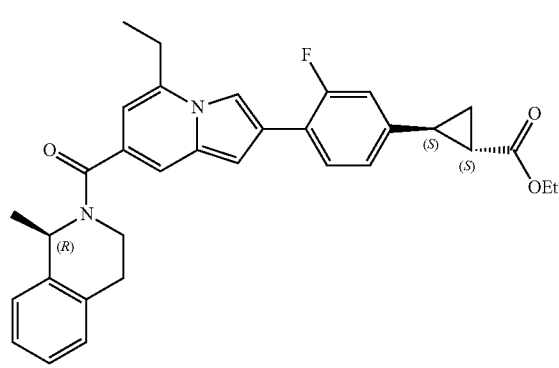

A4

To a degassed mixture of intermediate A3 (250 mg, 0.63 mmol), intermediate I1 (427 mg, 1.28 mmol) and potassium phosphate tribasic (401 mg, 1.89 mmol) in 1,4-dioxane (6.3 mL) and H₂O (1.6 mL) was added [1,1'-bis(di-tert-butylphosphino)ferrocene]dichloropalladium(II) (41.0 mg, 62.9 µmol). The reaction mixture was heated at 100° C. using a single mode microwave (Biotage® Initiator EXP 60) with a power output ranging from 0 to 400 W for 30 min. The reaction mixture was diluted with H₂O and EtOAc. The layers were separated and the aqueous phase was extracted with EtOAc (twice). The combined organic extracts were dried over MgSO₄, filtered and the solvent was evaporated in vacuo. The crude mixture was purified by preparative LC (regular SiOH, 30 µm, 40 g Interchim®, liquid injection (DCM), mobile phase gradient: heptane/EtOAc from 80:20 to 30:70) to give intermediate A4 (216 mg, 65%).

Compound 1

(1S,2S)-2-(4-{5-Ethyl-7-[(1R)-1-methyl-1,2,3,4-tetrahydroisoquinoline-2-carbonyl]indolizin-2-yl}-3-fluorophenyl)cyclopropane-1-carboxylic Acid

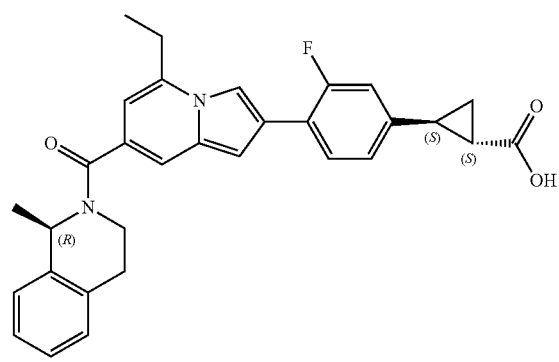

1

A mixture of intermediate A4 (216 mg, 0.41 mmol) and lithium hydroxide monohydrate (51.7 mg, 1.23 mmol) in THF (5.8 mL) and H₂O (2.9 mL) was stirred at rt for 24 h. The reaction mixture was diluted with a 1N aqueous solution of HCl and H₂O. The precipitate was filtered off and dried to give compound 1 (124 mg, 61%).

Compound 2

(1S,2S)-2-(4-{5-Ethyl-7-[(1R)-1-methyl-1,2,3,4-tetrahydroisoquinoline-2-carbonyl]-7,8-dihydroindolizin-2-yl}-3-fluorophenyl)cyclopropane-1-carboxamide

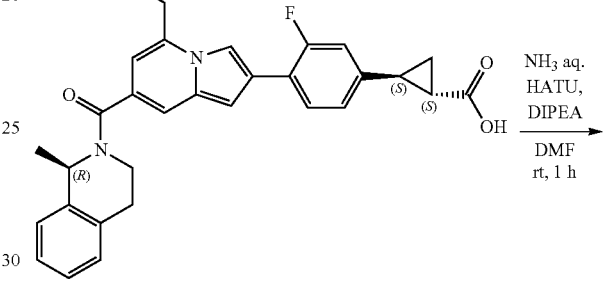

1

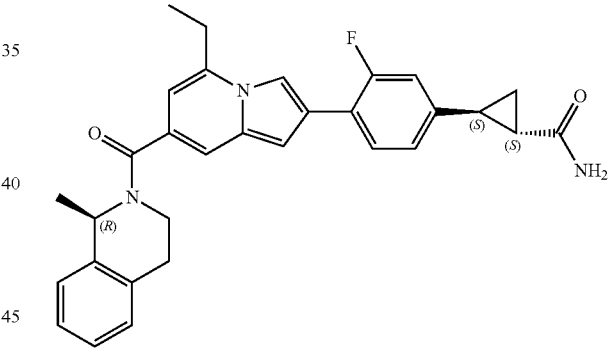

2

A mixture of compound 1 (112 mg, 0.23 mmol), HATU (111 mg, 0.29 mmol) and DIPEA (116 µL, 0.68 mmol) in DMF (1.3 mL) was stirred at rt for 1 h. Ammonia (28% in H₂O, 152 µL, 2.26 mmol) was added and the reaction mixture was stirred at rt for 1 h. The reaction mixture was diluted with H₂O and EtOAc. The layers were separated and the aqueous phase was extracted with EtOAc. The combined organic extracts were washed with brine, dried over MgSO₄, filtered and the solvent was evaporated in vacuo. The residue was taken up in MeOH. The solid was filtered off (100 mg) and dissolved in DCM. The organic phase was washed with a 1% aqueous solution of NaHCO₃ (twice), dried over MgSO₄, filtered and the solvent was evaporated in vacuo. The residue was taken up in MeOH. The solid was filtered off and dried under high vacuum at 60° C. for 5 h to give compound 2 (34 mg, 30%).

Compound 3
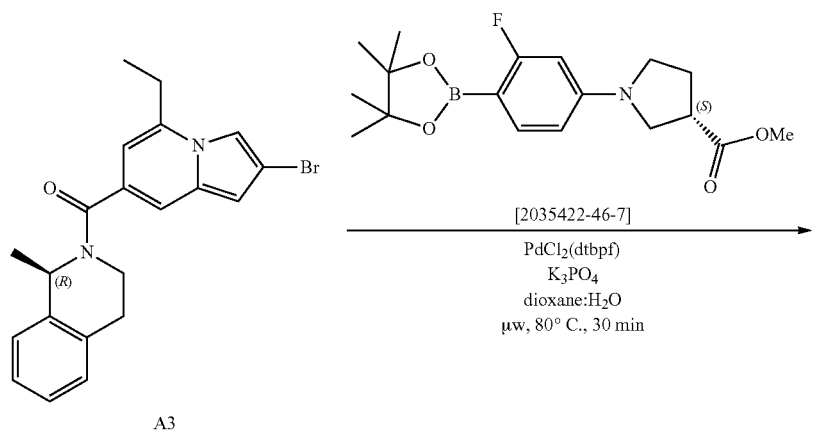
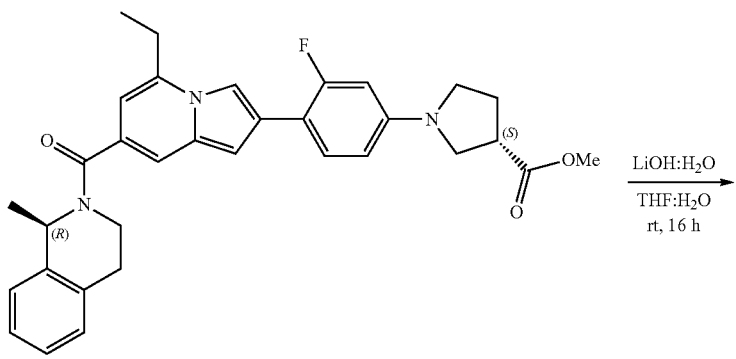
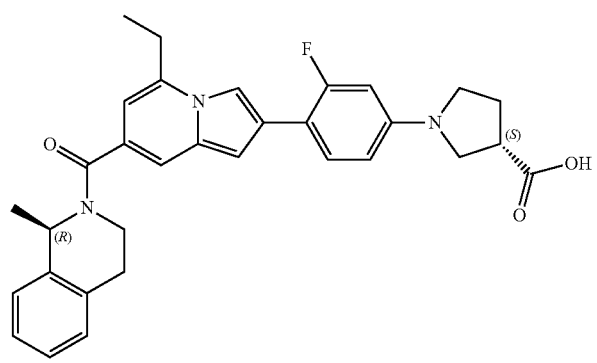
3

Intermediate A5

Methyl (3S)-1-(4-{5-ethyl-7-[(1R)-1-methyl-1,2,3,4-tetrahydroisoquinoline-2-carbonyl]indolizin-2-yl}-3-fluorophenyl)pyrrolidine-3-carboxylate

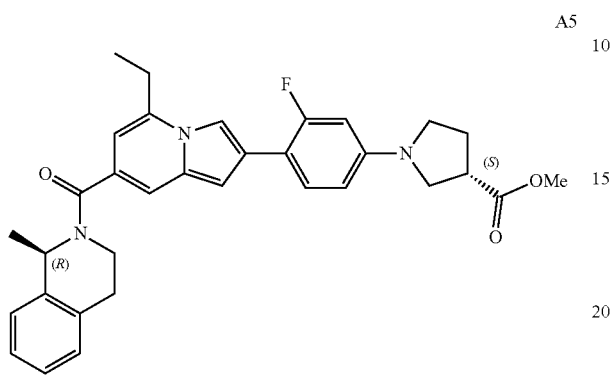

To a degassed mixture of intermediate A3 (170 mg, 0.43 mmol), methyl (3S)-1-[3-fluoro-4-(tetramethyl-1,3,2-dioxaborolan-2-yl)phenyl]pyrrolidine-3-carboxylate [2035422-46-7] (164 mg, 0.47 mmol) and potassium phosphate tribasic (272 mg, 1.28 mmol) in 1,4-dioxane (4 mL) and $H_2O$ (1 mL) was added [1,1'-bis(di-tert-butylphosphino)ferrocene] dichloropalladium(II) (27.9 mg, 42.8 µmol). The reaction mixture was heated at 80° C. using a single mode microwave (Biotage® Initiator EXP 60) with a power output ranging from 0 to 400 W for 30 min. The reaction mixture was diluted with $H_2O$ and EtOAc. The layers were separated and the aqueous phase was extracted with EtOAc (twice). The combined organic extracts were dried over $MgSO_4$, filtered and the solvent was evaporated in vacuo. The crude mixture was purified by preparative LC (regular SiOH, 30 µm, 40 g Interchim®, liquid injection (DCM), mobile phase gradient: heptane/EtOAc from 80:20 to 30:70) to afford intermediate A5 (100 mg, 43%).

Compound 3

(3S)-1-(4-{5-Ethyl-7-[(1R)-1-methyl-1,2,3,4-tetrahydroisoquinoline-2-carbonyl]indolizin-2-yl}-3-fluorophenyl)pyrrolidine-3-carboxylic Acid

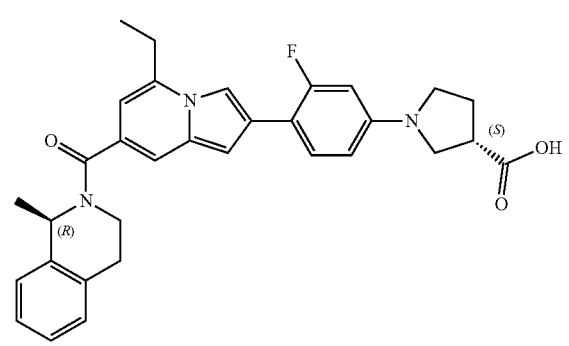

A mixture of intermediate A5 (100 mg, 185 µmol) and lithium hydroxide monohydrate (23.3 mg, 0.55 mmol) in THF (2.6 mL) and $H_2O$ (1.3 mL) was stirred at rt for 16 h. The reaction mixture was diluted with a 1N aqueous solution of HCl and $H_2O$. The mixture was extracted with EtOAc (twice). The combined organic extracts were dried over $MgSO_4$, filtered and the solvent was evaporated in vacuo. The residue was diluted with MeCN and EtOAc, and evaporated to dryness to give compound 3 (100 mg, quant.) as an orange solid.

Pyrazolo[1,5-a]pyridines

Synthesis of Intermediates

Synthesis of Intermediate I3

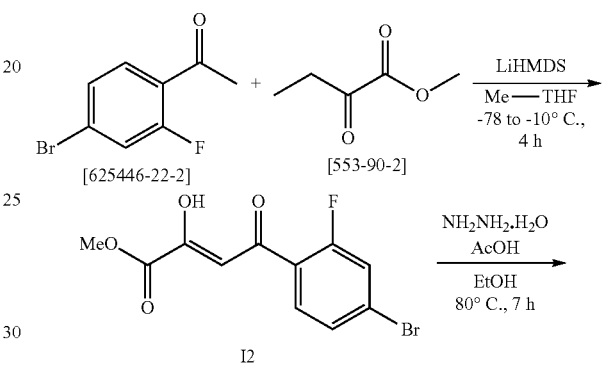

Intermediate I2

Methyl-4-(4-bromo-2-fluorophenyl)-2-hydroxy-4-oxobut-2-enoate

Lithium bis(trimethylsilyl)amide (1.5 M in THF, 50 mL, 75.0 mmol) was added to a mixture of 4-bromo-2-fluoroacetophenone [625446-22-2] (15.0 g, 69.1 mmol) in 2-methyltetrahydrofuran (150 mL) at −78° C. The reaction mixture was stirred at this temperature for 15 min and a solution of dimethyl oxalate [553-90-2] (8.33 g, 70.6 mmol) in 2-methyltetrahydrofuran (100 mL) was added. The reaction mixture was stirred at −10° C. for 4 h. A 3N aqueous solution of HCl was added and the aqueous phase was extracted with EtOAc (twice). The combined organic extracts were dried over MgSO$_4$, filtered and the solvent was evaporated in vacuo to afford intermediate I2 (21.9 g, quant.) as a yellow solid.

Intermediate I3

Methyl 3-(4-bromo-2-fluorophenyl)-1H-pyrazole-5-carboxylate

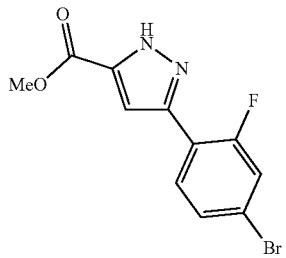

A mixture of intermediate I2 (21.9 g, 68.6 mmol), hydrazine monohydrate (80% in H$_2$O, 4.2 mL, 70.0 mmol) and acetic acid (0.9 mL, 15.6 mmol) in ethanol (200 mL) was stirred at 80° C. for 7 h. The reaction mixture was cooled down and a precipitate was formed. The precipitate was filtered off, washed with EtOH and dried under vacuum at 50° C. for 4 h to afford intermediate I3 (13.2 g, 64%) as a white solid.

Synthesis of Intermediates I4 and I5

I4: Ethyl cis-2-(trifluoro-λ$^4$-boranyl)cyclopropane-1-carboxylate potassium

I5: Ethyl trans-2-(trifluoro-λ$^4$-boranyl)cyclopropane-1-carboxylate Potassium

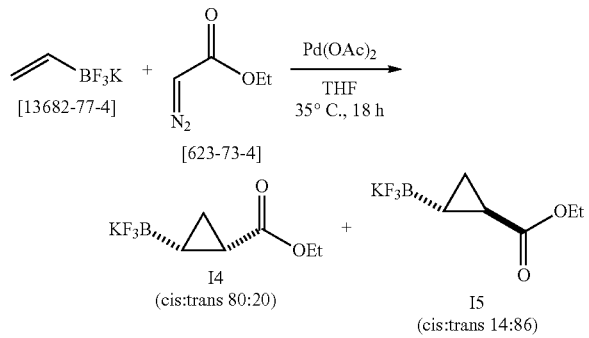

Potassium vinyltrifluoroborate [13682-77-4] (2.00 g, 15.0 mmol) was solubilized in THF (20.5 mL). Palladium acetate (33.5 mg, 0.15 mmol) was added and the reaction mixture was stirred at 35° C. Ethyl diazoacetate (85 wt. % in DCM, 2.00 mL, 16.4 mmol) in THF (2 mL) was added with a syringe pump over 4 h and the reaction mixture was stirred at 35° C. for 18 h. The reaction mixture was diluted with heptane at rt and the mixture was stirred for 30 min. The suspension was filtered off and crystallized from acetone (20 mL) at −18° C. The solid was filtered off to afford intermediate I4 (cis:trans 80:20, 520 mg, 16%) as a grey solid. The filtrate was washed with activated charcoal, filtered and concentrated to dryness. The residue was diluted with EtOH (20 mL) and heated at 50° C. Filtration of the gummy suspension delivered intermediate I5 (cis:trans 14:86, 1.83 g, 56%) as a white solid.

Synthesis of Intermediate I7

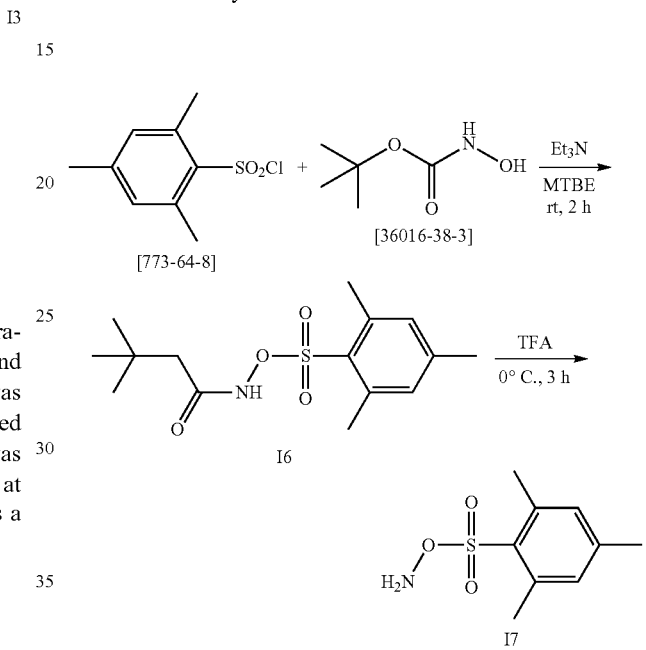

Intermediate I6 tert-Butyl N-[(2,4,6-trimethylbenzenesulfonyl)oxy]carbamate

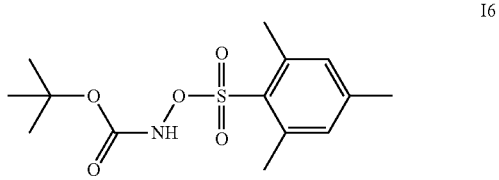 [SMILES: Cc1cc(C)c(S(=O)(=O)ONC(=O)OC(C)(C)C)c(C)c1]

To a mixture of 2-mesitylenesulfonyl chloride [773-64-8] (5.47 g, 25.0 mmol) and tert-butyl N-hydroxycarbamate [36016-38-3] (3.67 g, 27.5 mmol) in MTBE (51 mL) at 0° C. was added Et$_3$N (3.82 mL, 27.5 mmol) dropwise. The reaction mixture was stirred at rt for 2 h. The suspension was filtered and the solid was washed with MTBE. The filtrate was dried over MgSO$_4$, filtered and concentrated in vacuo to afford intermediate I6 (8.75 g, quant., 90% purity) as a yellow oil.

Intermediate I7

Amino 2,4,6-trimethylbenzene-1-sulfonate

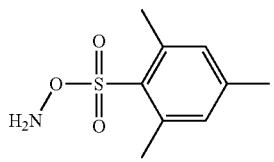

I7

A solution of intermediate I6 (8.75 g, 25.0 mmol, 90% purity) in TFA (10 mL) was stirred at 0° C. for 3 h. The reaction mixture was poured out into iced water. The precipitate was filtered off, washed with $H_2O$ and dried under vacuum to give intermediate I7 (1 g, 19%) as a white solid.

Synthesis of Intermediate I8

Ethyl 3-(4-bromo-3-fluorophenyl)prop-2-ynoate

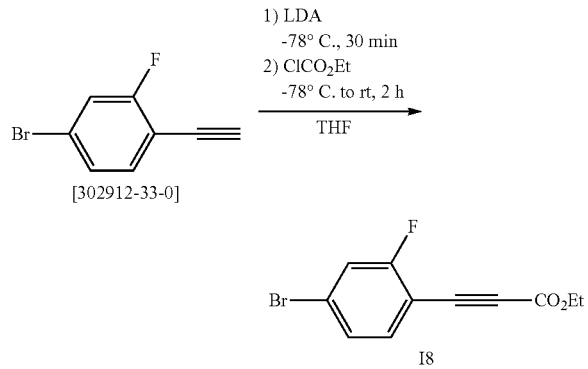

n-Butyllithium (1.6 M in hexane, 1.5 mL, 2.40 mmol) was added to a solution of DIPA (0.4 mL, 2.85 mmol) in THF (15 mL) at −78° C. The reaction mixture was stirred at for 30 min and a solution of 4-bromo-2-fluoroacetylene [302912-33-0] (0.47 g, 2.35 mmol) in THF (5 mL) was added. The reaction mixture was stirred at −78° C. for 30 min. Ethyl chloroformate (0.5 mL, 5.23 mmol) was added and the reaction mixture was stirred at −78° C. for 30 min and at rt for 2 h. The reaction mixture was quenched by the addition of a 10% aqueous solution of $NH_4Cl$ and diluted with EtOAc. The layers were separated and the aqueous phase was extracted with EtOAc. The combined organic extracts were washed with brine, dried over $MgSO_4$, filtered and evaporated in vacuo. The crude mixture was purified by preparative LC (irregular SiOH, 15-40 μm, 40 g GraceResolv™, liquid injection (DCM), mobile phase gradient: heptane/EtOAc from 100:0 to 85:15) to give intermediate I8 (505 mg, 79%).

Synthesis of Pyrazolo[1,5-a]pyridine Intermediates

Synthesis of Intermediate B3

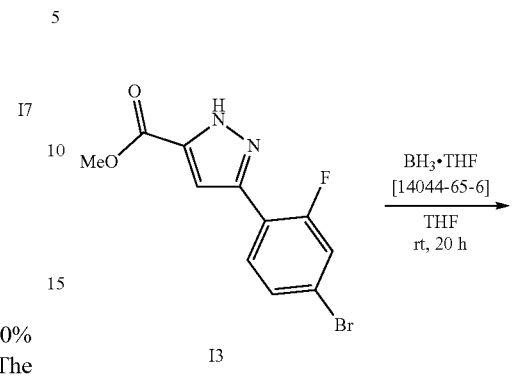

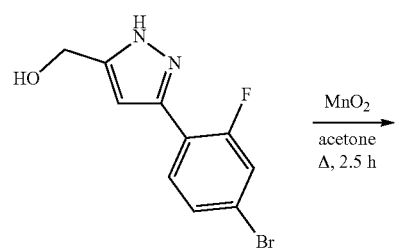

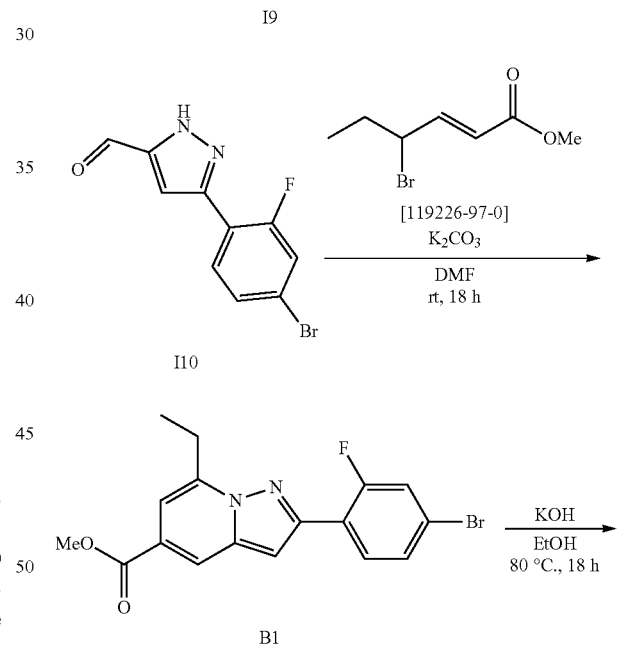

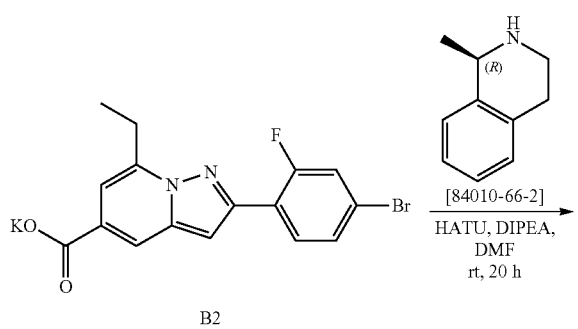

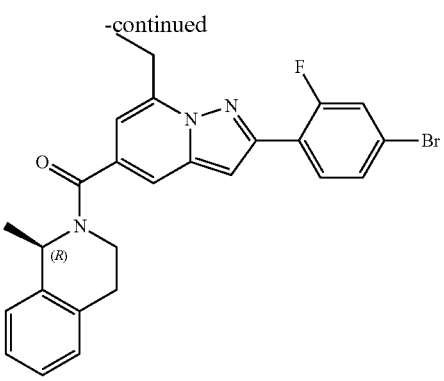

B3

Intermediate I9

[3-(4-Bromo-2-fluorophenyl)-1H-pyrazol-5-yl]
methanol

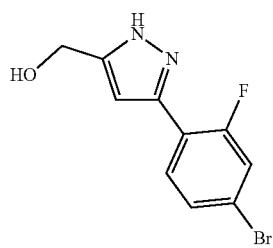

I9

Boran tetrahydrofuran complex (1.0 M in THF, 70 mL, 70.0 mmol) was added slowly to a solution of intermediate I3 (7.07 g, 23.6 mmol) in THF (200 mL). The reaction mixture was stirred at rt for 20 h. The reaction mixture was quenched by the careful addition of MeOH. The solution was diluted with EtOAc and brine. The layers were separated and the aqueous phase was extracted with EtOAc. The combined organic extracts were dried over $MgSO_4$, filtered and evaporated in vacuo. The residue was diluted with DCM. The precipitate was filtered off, washed with DCM and dried to afford intermediate I9 (3.24 g, 50%) as a white solid.

Intermediate I10

3-(4-Bromo-2-fluorophenyl)-1H-pyrazole-5-carbaldehyde

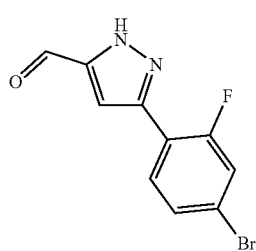

I10

A mixture of intermediate I9 (6.41 g, 23.6 mmol) and manganese dioxide (20.0 g; 230 mmol) in acetone (300 mL) was stirred under reflux for 2.5 h. The reaction mixture was filtered over a pad of Celite® and the filtrate was evaporated in vacuo to afford intermediate I10 (1.77 g, 28%) as a white solid.

Intermediate B1

Methyl 2-(4-bromo-2-fluorophenyl)-7-ethylpyrazolo
[1,5-a]pyridine-5-carboxylate

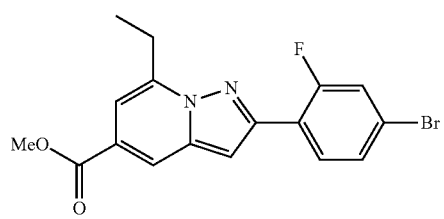

B1

A mixture of intermediate I10 (1.77 g, 6.58 mmol), methyl-4-bromohex-2-enoate [119226-97-0](1.60 g, 7.34 mmol) and potassium carbonate (1.90 g, 13.8 mmol) in DMF (50 mL) was stirred at rt for 18 h. The reaction mixture was diluted with EtOAc and $H_2O$. The layers were separated and the aqueous phase was extracted with EtOAc. The combined organic extracts were washed with brine, dried over $MgSO_4$, filtered and evaporated in vacuo. The residue was diluted with MeOH and triturated in MeOH. The solid was filtered off and washed with MeOH to afford intermediate B1 (1.4 g, 56%) as a white solid.

Intermediate B2

Potassium 2-(4-bromo-2-fluorophenyl)-7-ethylpyrazolo[1,5-a]pyridine-5-carboxylate

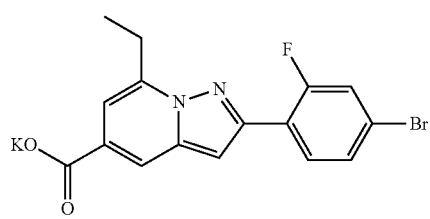

B2

Potassium hydroxide (730 mg, 11.1 mmol, 85% purity) was added to a solution of intermediate B1 (1.40 g, 3.71 mmol) in EtOH (35 mL). The reaction mixture was stirred at 80° C. for 18 h. The reaction mixture was cooled down and a precipitate was observed. The precipitate was filtered off to afford intermediate B2 (975 mg, 65%) as a white solid.

Intermediate B3

(1R)-2-[2-(4-Bromo-2-fluorophenyl)-7-ethylpyrazolo[1,5-a]pyridine-5-carbonyl]-1-methyl-1,2,3,4-tetrahydroisoquinoline

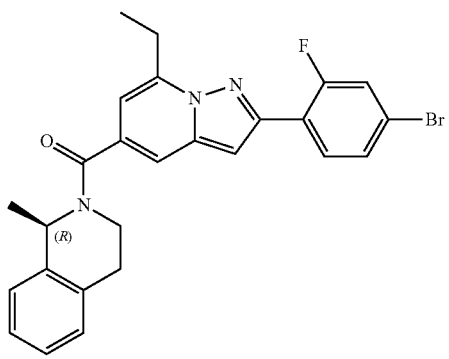

B3

A mixture of intermediate B2 (500 mg, 1.25 mmol), (1R)-1-methyl-1,2,3,4-tetrahydroisoquinoline [84010-66-2] (220 mg, 1.5 mmol), HATU (640 mg, 1.68 mmol) and DIPEA (640 μL, 3.71 mmol) in DMF (25 mL) was stirred at rt for 20 h. The reaction mixture was diluted with EtOAc and brine. The layers were separated and the aqueous phase was extracted with EtOAc. The combined organic extracts were washed with brine, dried over MgSO₄, filtered and evaporated in vacuo. The crude mixture was purified by preparative LC (irregular SiOH, 15-40 μm, 80 g Grace®, liquid injection (DCM), mobile phase gradient: heptane/EtOAc from 90:10 to 0:100) to give intermediate B3 (622 mg, quant.) as a white foam.

Synthesis of Intermediate B6

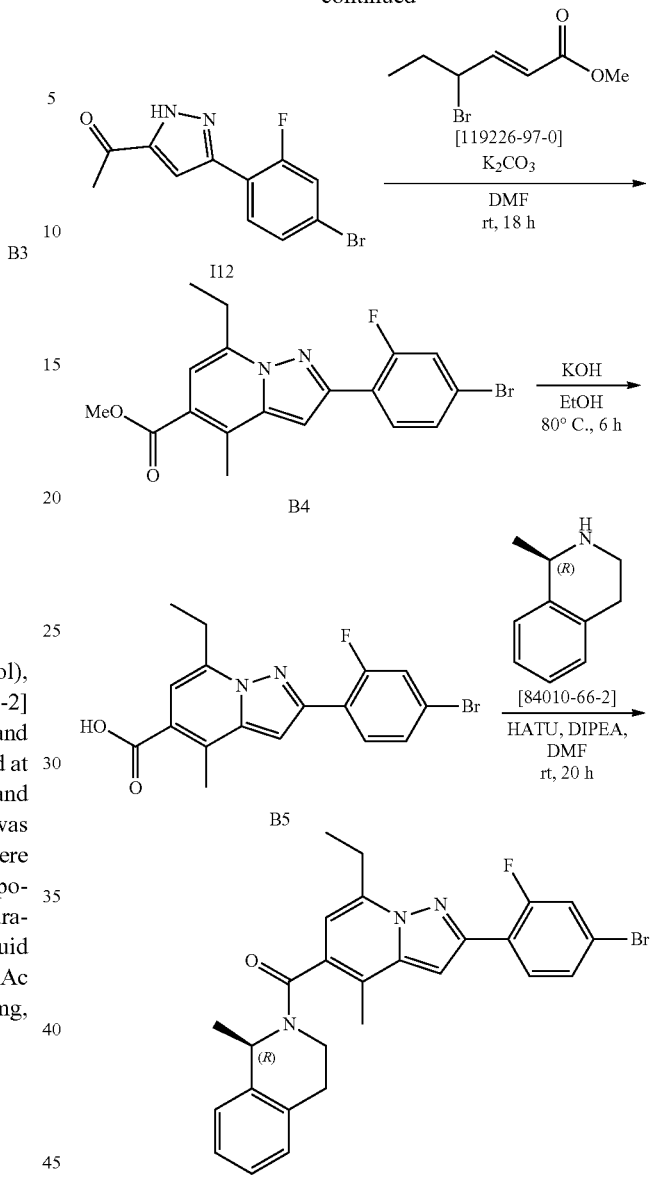

Intermediate I11

3-(4-Bromo-2-fluorophenyl)-N-methoxy-N-methyl-1H-pyrazole-5-carboxamide

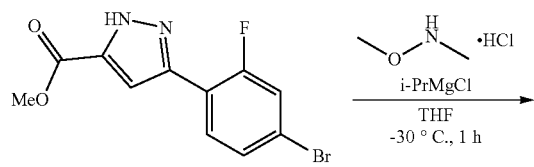

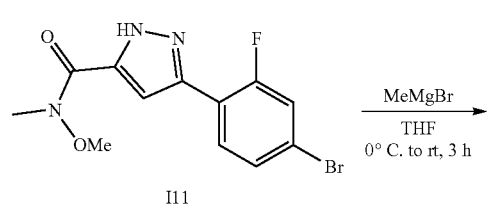

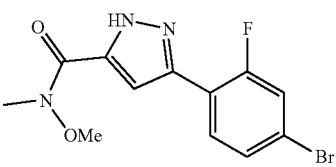

Under nitrogen atmosphere a mixture of intermediate I3 (500 mg, 1.67 mmol) and N,O-dimethylhydroxylamine hydrochloride (489 mg, 5.02 mmol) in THF (2 mL) was stirred at −30° C. Isopropylmagnesium chloride (2.0 M in THF, 5.0 mL, 10.0 mmol) was added and the reaction mixture was stirred at −30° C. for 1 h. The reaction was quenched by the addition of a 1N aqueous solution of HCl and diluted with EtOAc. The layers were separated and the aqueous phase was extracted with EtOAc. The combined organic extracts were washed with brine, dried over MgSO₄, filtered and evaporated in vacuo to afford intermediate I11 (538 mg, 98%) as a white solid.

Intermediate I12

1-[3-(4-Bromo-2-fluorophenyl)-1H-pyrazol-5-yl]ethan-1-one

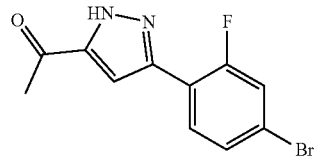

Under nitrogen atmosphere methylmagnesium bromide (3.0 M in Et₂O, 1.1 mL, 3.30 mmol) was added to a solution of intermediate I11 (538 mg, 1.64 mmol) in THF (2 mL) at 0° C. The reaction mixture was stirred at rt for 3 h. The reaction was quenched by the addition of an aqueous solution of NH₄Cl and diluted with EtOAc. The layers were separated and the aqueous phase was extracted with EtOAc. The combined organic extracts were washed with brine, dried over MgSO₄, filtered and evaporated in vacuo to afford intermediate I12 (447 mg, 96%) as a white solid.

Intermediate B4

Methyl 2-(4-bromo-2-fluorophenyl)-7-ethyl-4-methylpyrazolo[1,5-a]pyridine-5-carboxylate

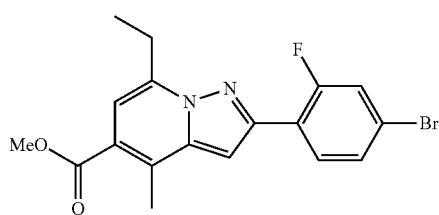

A mixture of intermediate I12 (380 mg, 1.34 mmol), methyl-4-bromohex-2-enoate [119226-97-0] (365 mg, 1.50 mmol, 85% purity) and potassium carbonate (388 mg, 2.81 mmol) in DMF (10 mL) was stirred at rt for 18 h. The reaction mixture was diluted with EtOAc and H₂O. The layers were separated and the aqueous phase was extracted with EtOAc. The combined organic extracts were washed with brine, dried over MgSO₄, filtered and evaporated in vacuo. The crude mixture was purified by preparative LC (irregular SiOH, 15-40 μm, 40 g Grace®, liquid injection (DCM), mobile phase gradient: heptane/EtOAc from 100:0 to 60:40) to afford intermediate B4 (182 mg, 35%) as a white solid.

Intermediate B5

2-(4-Bromo-2-fluorophenyl)-7-ethyl-4-methylpyrazolo[1,5-a]pyridine-5-carboxylic Acid

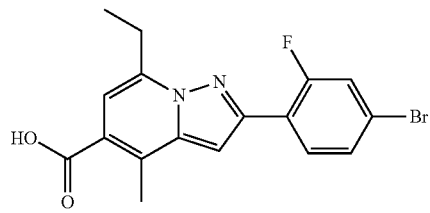

Potassium hydroxide (100 mg, 1.52 mmol, 85% purity) was added to a solution of intermediate B4 (200 mg, 0.51 mmol) in EtOH (5 mL). The reaction mixture was stirred at 80° C. for 6 h. The reaction mixture was diluted with EtOAc and a 10% aqueous solution of KHSO₄ was added. The layers were separated and the aqueous phase was extracted with EtOAc. The combined organic extracts were washed with brine, dried over MgSO₄, filtered and evaporated in vacuo to afford intermediate B5 (180 mg, 93%).

Intermediate B6

(1R)-2-[2-(4-Bromo-2-fluorophenyl)-7-ethyl-4-methylpyrazolo[1,5-a]pyridine-5-carbonyl]-1-methyl-1,2,3,4-tetrahydroisoquinoline

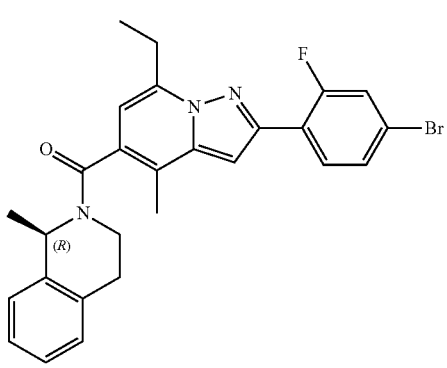

A mixture of intermediate B5 (180 mg, 0.48 mmol), (1R)-1-methyl-1,2,3,4-tetrahydroisoquinoline [84010-66-2] (83.4 mg, 0.57 mmol), HATU (246 mg, 0.65 mmol) and DIPEA (246 μL, 1.43 mmol) in DMF (8 mL) was stirred at rt for 20 h. The reaction mixture was diluted with EtOAc and brine. The layers were separated and the aqueous phase was extracted with EtOAc. The combined organic extracts were dried over MgSO₄, filtered and evaporated in vacuo. The crude mixture was purified by preparative LC (irregular SiOH, 15-40 μm, 40 g Grace®, liquid injection (DCM), mobile phase gradient: heptane/EtOAc from 90:10 to 0:100) to afford intermediate B6 (232 mg, 96%) as a white foam.

Synthesis of Intermediate B10

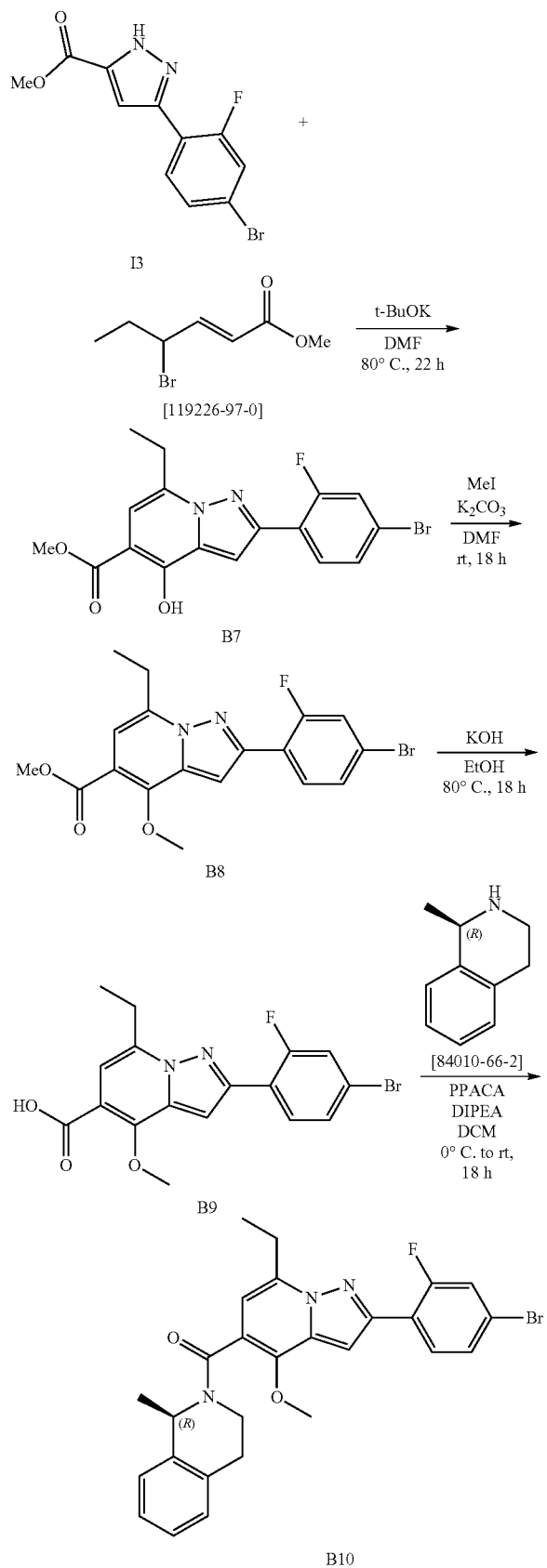

Intermediate B7

Methyl 2-(4-bromo-2-fluorophenyl)-7-ethyl-4-hydroxypyrazolo[1,5-a]pyridine-5-carboxylate

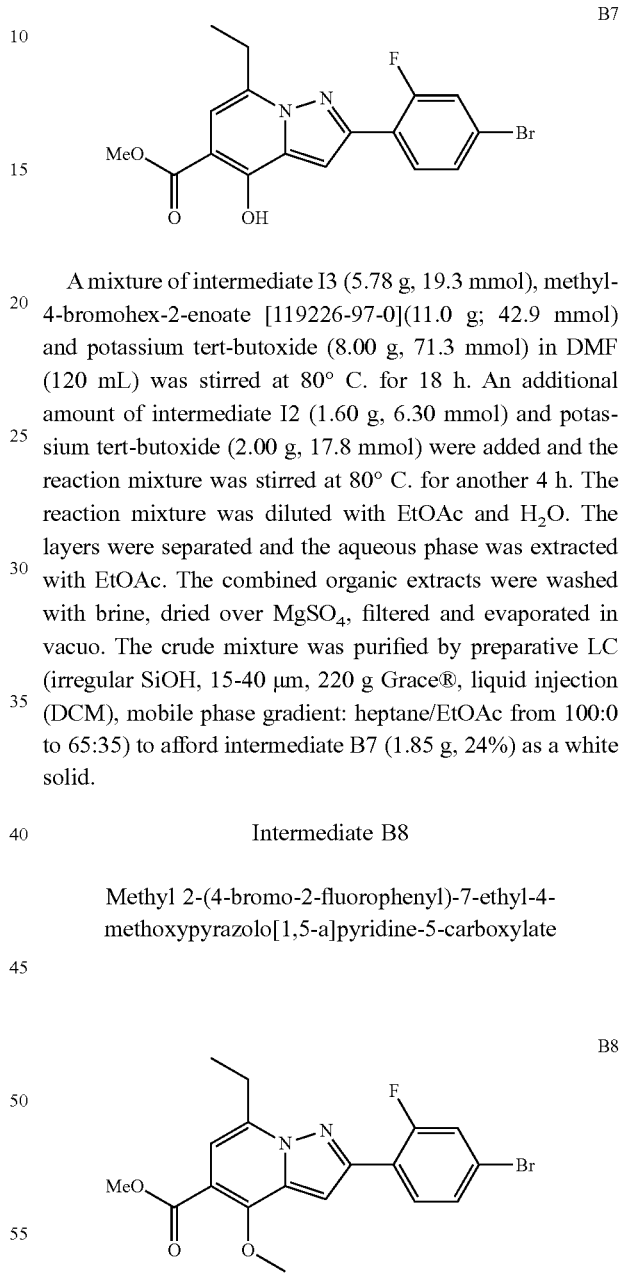

A mixture of intermediate I3 (5.78 g, 19.3 mmol), methyl-4-bromohex-2-enoate [119226-97-0](11.0 g; 42.9 mmol) and potassium tert-butoxide (8.00 g, 71.3 mmol) in DMF (120 mL) was stirred at 80° C. for 18 h. An additional amount of intermediate I2 (1.60 g, 6.30 mmol) and potassium tert-butoxide (2.00 g, 17.8 mmol) were added and the reaction mixture was stirred at 80° C. for another 4 h. The reaction mixture was diluted with EtOAc and H$_2$O. The layers were separated and the aqueous phase was extracted with EtOAc. The combined organic extracts were washed with brine, dried over MgSO$_4$, filtered and evaporated in vacuo. The crude mixture was purified by preparative LC (irregular SiOH, 15-40 μm, 220 g Grace®, liquid injection (DCM), mobile phase gradient: heptane/EtOAc from 100:0 to 65:35) to afford intermediate B7 (1.85 g, 24%) as a white solid.

Intermediate B8

Methyl 2-(4-bromo-2-fluorophenyl)-7-ethyl-4-methoxypyrazolo[1,5-a]pyridine-5-carboxylate A mixture of intermediate B7 (100 mg, 0.25 mmol), methyl iodide (19.0 μL, 305 μmol) and potassium carbonate (70.3 mg, 0.51 mmol) in DMF (2 mL) was stirred at r for 18 h. The reaction mixture was diluted with EtOAc and H$_2$O. The layers were separated and the aqueous phase was extracted with EtOAc. The combined organic extracts were washed with brine, dried over MgSO$_4$, filtered and evaporated in vacuo. The crude mixture was purified by preparative LC (irregular SiOH, 15-40 μm, 12 g Grace®, liquid injection (DCM), mobile phase gradient: heptane/EtOAc from 100:0 to 60:40) to afford intermediate B8 (85 mg, 82%) as a white solid.

Intermediate B9

2-(4-Bromo-2-fluorophenyl)-7-ethyl-4-methoxy-pyrazolo[1,5-a]pyridine-5-carboxylic Acid

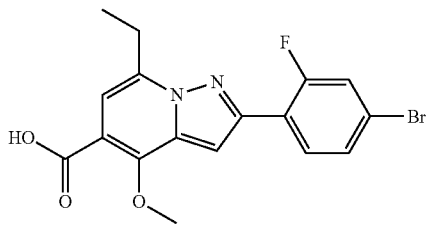

B9

Potassium hydroxide (41.1 mg, 0.62 mmol, 85% purity) was added to a solution of intermediate B8 (85.0 mg, 0.21 mmol) in EtOH (2 mL). The reaction mixture was stirred at 80° C. for 18 h. The mixture was diluted with EtOAc and a 10% aqueous solution of KHSO₄ was added. The layers were separated and the aqueous phase was extracted with EtOAc. The combined organic extracts were washed with brine, dried over MgSO₄, filtered and evaporated in vacuo to afford intermediate B9 (80 mg, 97%) as a white solid.

Intermediate B10

(1R)-2-[2-(4-Bromo-2-fluorophenyl)-7-ethyl-4-methoxypyrazolo[1,5-a]pyridine-5-carbonyl]-1-methyl-1,2,3,4-tetrahydroisoquinoline

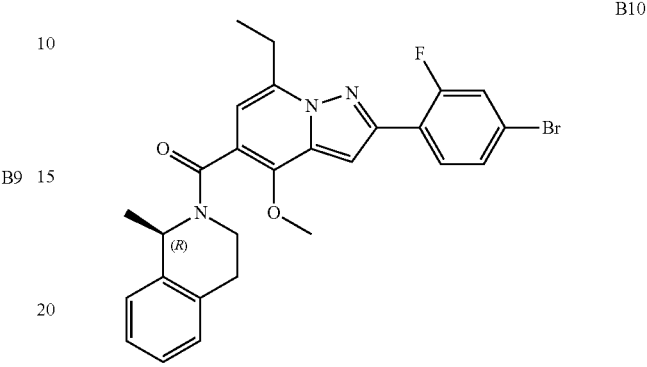

B10

A mixture of intermediate B9 (80.0 mg, 0.20 mmol), (1R)-1-methyl-1,2,3,4-tetrahydroisoquinoline [84010-66-2] (34.8 mg, 0.24 mmol) and DIPEA (174 μL, 1.01 mmol) in DCM (1 mL) was stirred at 0° C. PPACA (50 wt. % in EtOAc, 0.30 mL, 0.51 mmol) was added slowly. The reaction mixture was stirred at 0° C. for 10 min and at rt for 18 h. The reaction mixture was diluted with EtOAc and a 10% aqueous solution of KHSO₄ was added. The layers were separated and the aqueous phase was extracted with EtOAc. The combined organic extracts were washed with brine, dried over MgSO₄, filtered and evaporated in vacuo to afford intermediate B10 (83 mg, 78% as a white foam.

Synthesis of Intermediate B13

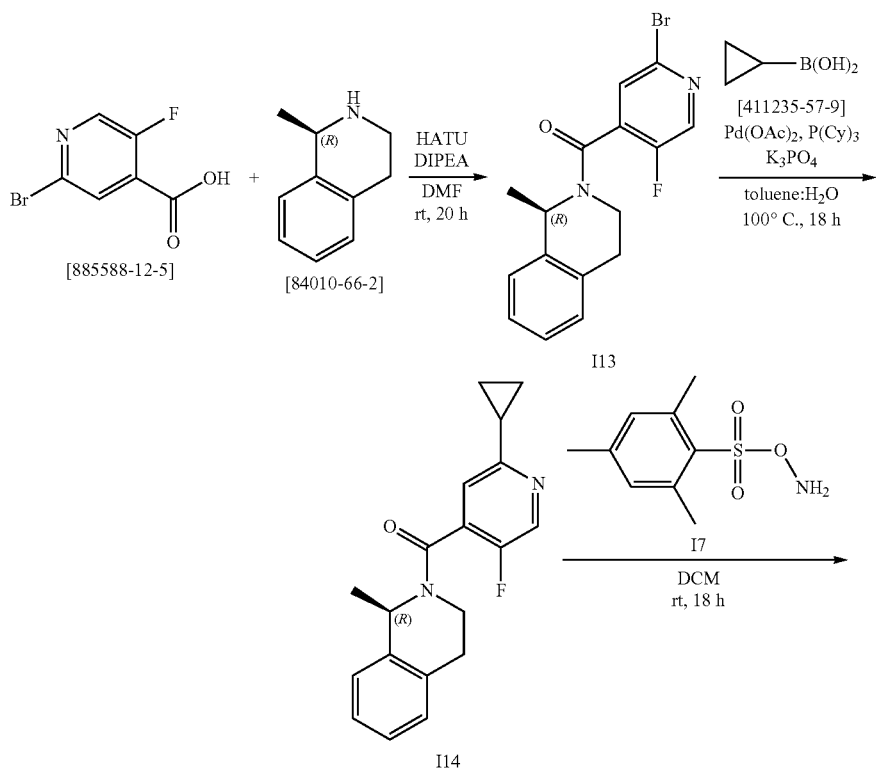

-continued

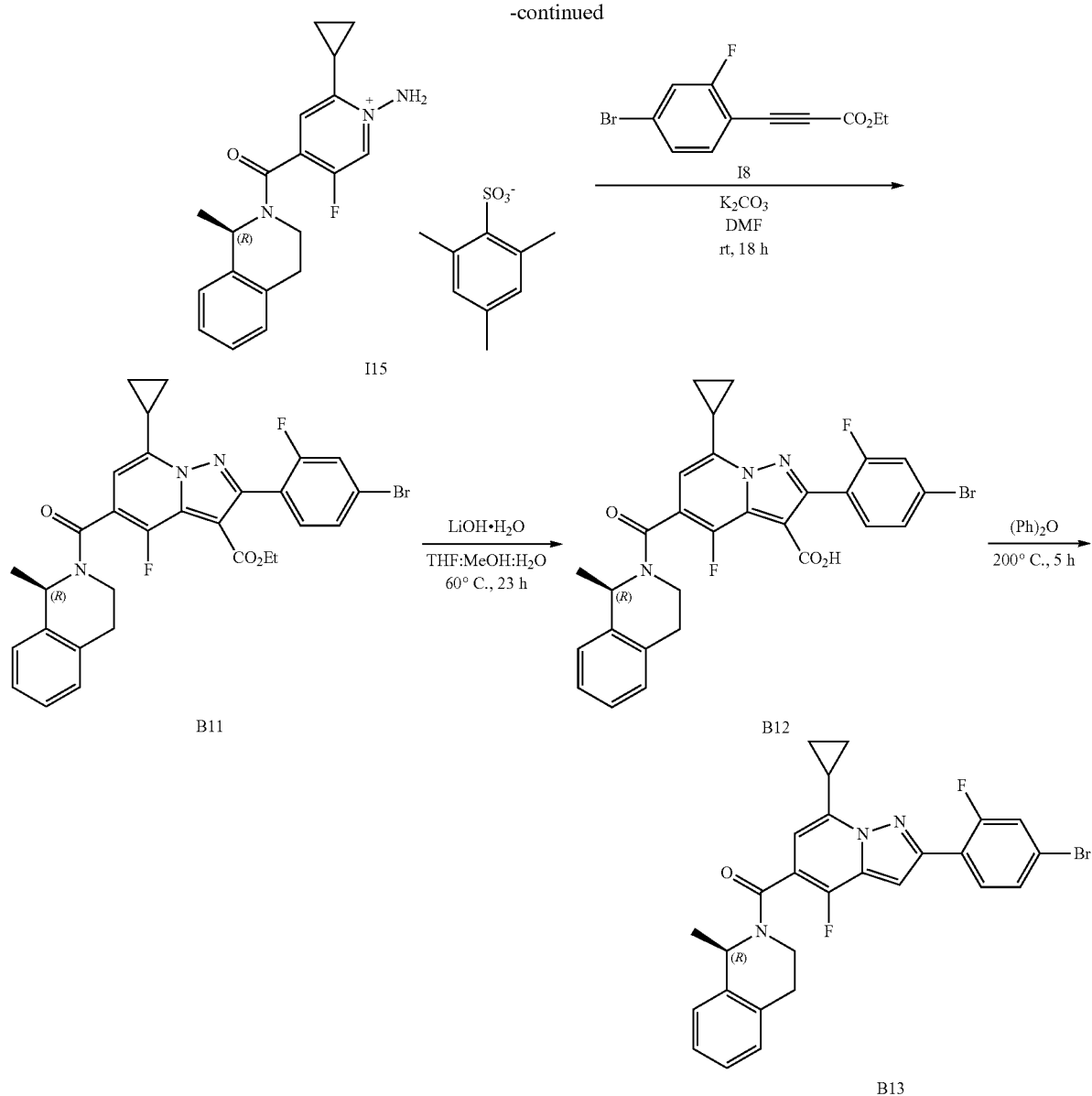

Intermediate I13

(1R)-2-(2-Bromo-5-fluoropyridine-4-carbonyl)-1-methyl-1,2,3,4-tetrahydroisoquinoline

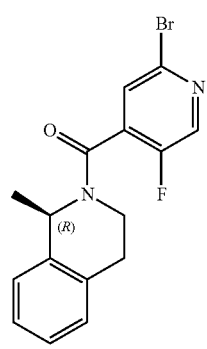

I13

A mixture of 2-bromo-5-fluoroisonicotinic acid [885588-12-5] (1.00 g, 4.55 mmol), (1R)-1-methyl-1,2,3,4-tetrahydroisoquinoline [84010-66-2] (803 mg, 5.45 mmol), HATU (2.34 g, 6.14 mmol) and DIPEA (2.34 mL, 13.5 mmol) in DMF (50 mL) was stirred at rt for 20 h. The reaction mixture was diluted with EtOAc and brine. The layers were separated and the aqueous phase was extracted with EtOAc. The combined organic extracts were dried over MgSO$_4$, filtered and evaporated in vacuo. The crude mixture was purified by preparative LC (irregular SiOH, 15-40 µm, 80 g Grace®, liquid injection (DCM), mobile phase gradient: heptane/EtOAc from 90:10 to 0:100) to afford intermediate I13 (1.62 g, quant.).

Intermediate I14

(1R)-2-(2-Cyclopropyl-5-fluoropyridine-4-carbonyl)-1-methyl-1,2,3,4-tetrahydroisoquinoline

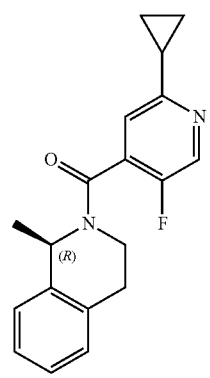

I14

To a solution of intermediate I13 (1.50 g, 4.30 mmol) in toluene (30 mL) were added cyclopropylboronic acid [411235-57-9] (738 mg, 8.59 mmol), potassium phosphate tribasic (2.28 g, 10.7 mmol), tricyclohexylphosphine (361 mg, 1.29 mmol) and H$_2$O (4.5 mL). The mixture was purged with nitrogen (3 times) and palladium acetate (145 mg, 644 µmol) was added. The reaction mixture was stirred at 100° C. for 18 h. The reaction mixture was diluted with EtOAc and H$_2$O. The layers were separated and the aqueous phase was extracted with EtOAc. The combined organic extracts were washed with brine, dried over MgSO$_4$, filtered, and evaporated in vacuo. The crude mixture was purified by preparative LC (irregular SiOH, 15-40 µm, 80 g GraceResolv™, liquid injection (DCM), mobile phase gradient: heptane/EtOAc from 100:0 to 90:10 and from 50:50 to 85:15) to afford intermediate I14 (1.15 g, 86%) as a colorless gum.

Intermediate I15

1-Amino-2-cyclopropyl-5-fluoro-4-[(1R)-1-methyl-1,2,3,4-tetrahydroisoquinoline-2-carbonyl]pyridin-1-ium 2,4,6-trimethylbenzene-1-sulfonate

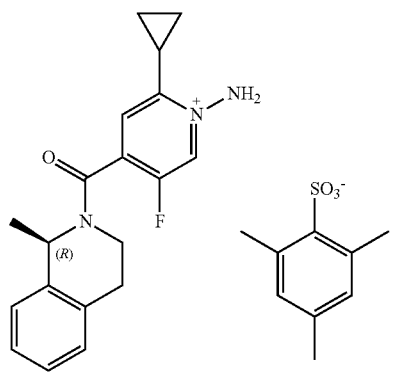

I15

A mixture of intermediate I14 (1.24 g, 4.00 mmol) and intermediate I7 (1.00 g, 4.65 mmol) in DCM (10 mL) was stirred at rt for 18 h. The reaction mixture was evaporated in vacuo to afford intermediate I15 (1.88 g, 90% as a white foam.

Intermediate B11

Ethyl 2-(4-bromo-2-fluorophenyl)-7-cyclopropyl-4-fluoro-5-[(1R)-1-methyl-1,2,3,4-tetrahydroisoquinoline-2-carbonyl]pyrazolo[1,5-a]pyridine-3-carboxylate

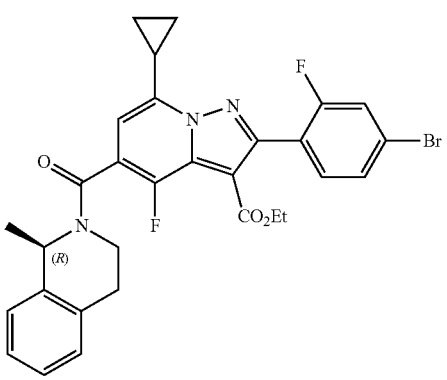

B11

A mixture of intermediate I15 (1.00 g, 1.90 mmol), intermediate I8 (550 mg, 2.03 mmol) and potassium carbonate (526 mg, 3.81 mmol) in DMF (15 mL) was stirred at rt for 18 h. The reaction mixture was diluted with EtOAc and H$_2$O. The layers were separated and the aqueous phase was extracted with EtOAc. The combined organic extracts were washed with brine, dried over MgSO$_4$, filtered and evaporated in vacuo. The crude mixture was purified by preparative LC (irregular SiOH, 15-40 µm, 80 g Grace®, liquid injection (DCM), mobile phase gradient: heptane/EtOAc from 100:0 to 50:50) to afford intermediate B11 (515 mg, 45%) as a yellow foam.

Intermediate B12

2-(4-Bromo-2-fluorophenyl)-7-cyclopropyl-4-fluoro-5-[(1R)-1-methyl-1,2,3,4-tetrahydroisoquinoline-2-carbonyl]pyrazolo[1,5-a]pyridine-3-carboxylic Acid

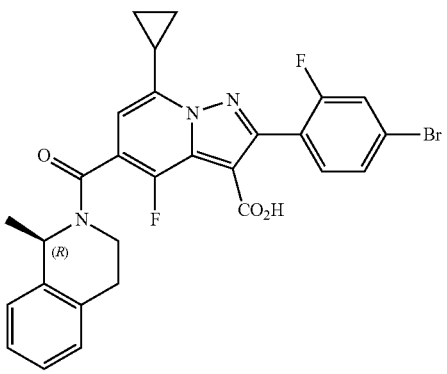

B12

Lithium hydroxide monohydrate (545 mg, 13.0 mmol) was added to a solution of intermediate B11 (515 mg, 0.87 mmol) in THF (6 mL) and H₂O (4 mL). The reaction mixture was stirred at 60° C. for 18 h. An additional amount of lithium hydroxide monohydrate (545 mg, 13.0 mmol) and MeOH (2 mL) were added and the reaction mixture was stirred at 60° C. for 5 h. A 10% aqueous solution of KHSO₄ was added until pH was 6 and the aqueous phase was extracted with EtOAc. The combined organic extracts were washed with H₂O, dried over MgSO₄, filtered and evaporated in vacuo to afford intermediate B12 (520 mg, quant.) as a pale yellow gum.

Intermediate B13

(1R)-2-[2-(4-Bromo-2-fluorophenyl)-7-cyclopropyl-4-fluoropyrazolo[1,5-a]pyridine-5-carbonyl]-1-methyl-1,2,3,4-tetrahydroisoquinoline

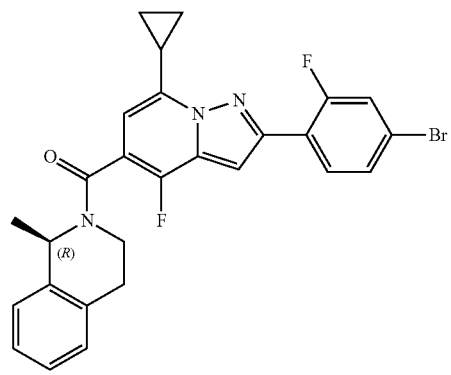

B13

A solution of intermediate B12 (520 mg, 0.87 mmol) in diphenyl ether (5 mL) was stirred at 200° C. for 5 h. The reaction mixture was purified by preparative LC (irregular SiOH, 15-40 μm, 80 g Grace®, liquid injection (DCM), mobile phase gradient: heptane/EtOAc from 100:0 to 80:20) to give intermediate B13 (129 mg, 28%) as an off-white foam.

Synthesis of the Final Compounds

Compound 4

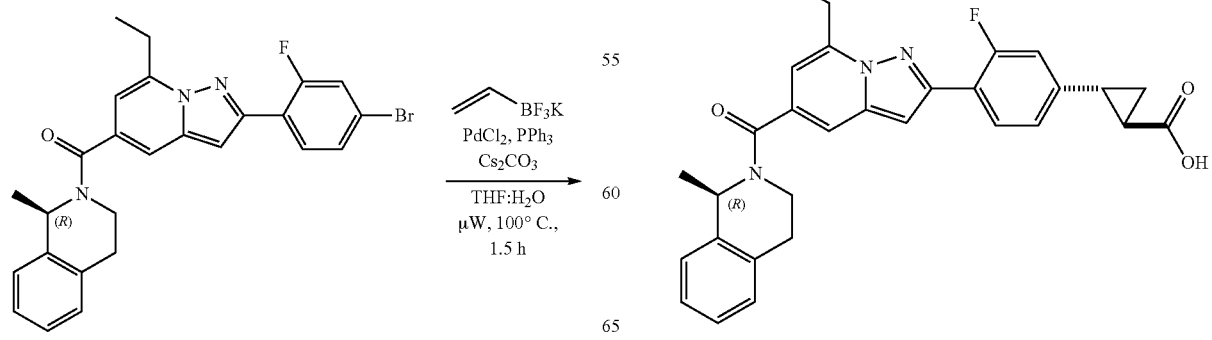

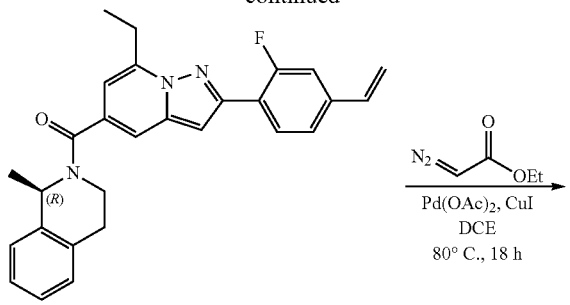

B14

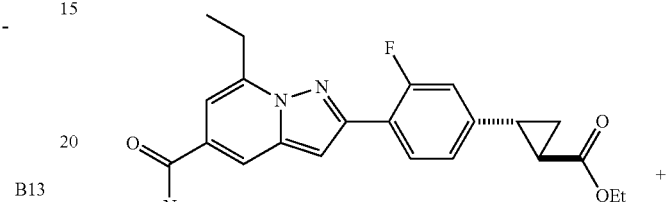

B15 (trans)

B16 (cis)

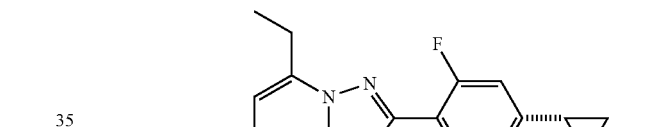

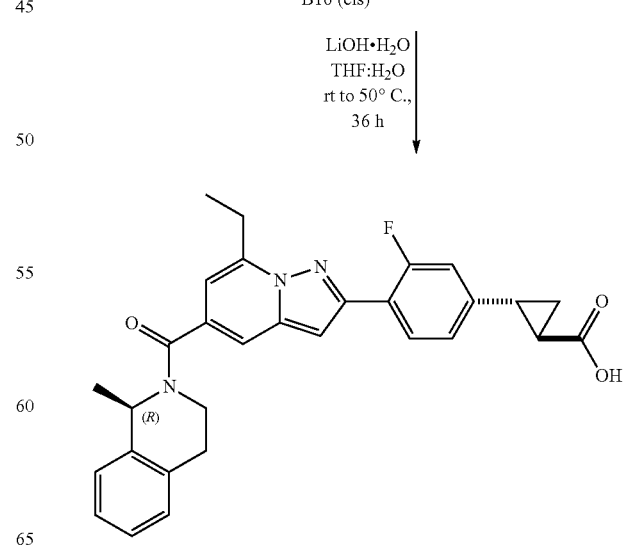

4

Intermediate B14

(1R)-2-[2-(4-Ethenyl-2-fluorophenyl)-7-ethylpyrazolo[1,5-a]pyridine-5-carbonyl]-1-methyl-1,2,3,4-tetrahydroisoquinoline

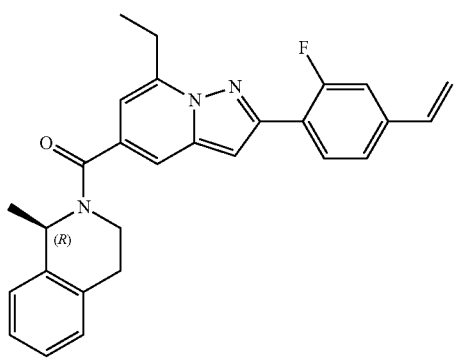

B14

Palladium chloride (7.00 mg, 39.5 µmol) was added to a degassed mixture of intermediate B3 (400 mg, 0.81 mmol), potassium vinyltrifluoroborate [13682-77-4] (325 mg, 2.43 mmol), cesium carbonate (1.20 g, 3.68 mmol) and triphenylphosphine (30.0 mg, 114 µmol) in THF and H₂O (9:1, 15 mL). The reaction mixture was heated at 100° C. using a single mode microwave (Biotage® Initiator EXP 60) with a power output ranging from 0 to 400 W for 1.5 h. The reaction mixture was diluted with EtOAc and H₂O. The layers were separated and the organic phase was washed with H₂O, dried over MgSO₄, filtered, and concentrated in vacuo. The crude mixture was purified by preparative LC (regular SiOH, 30 µm, 40 g Grace®, liquid injection (DCM), mobile phase gradient: heptane/EtOAc from 100:0 to 60:40) to afford intermediate B14 (249 mg, 70%) as a white foam.

Intermediates B15 and B16

B15: Ethyl trans-2-(4-{7-ethyl-5-[(1R)-1-methyl-1,2,3,4-tetrahydroisoquinoline-2-carbonyl]pyrazolo[1,5-a]pyridin-2-yl}-3-fluorophenyl)cyclopropane-1-carboxylate B16: Ethyl cis-2-(4-{7-ethyl-5-[(1R)-1-methyl-1,2,3,4-tetrahydroisoquinoline-2-carbonyl]pyrazolo[1,5-a]pyridin-2-yl}-3-fluorophenyl)cyclopropane-1-carboxylate

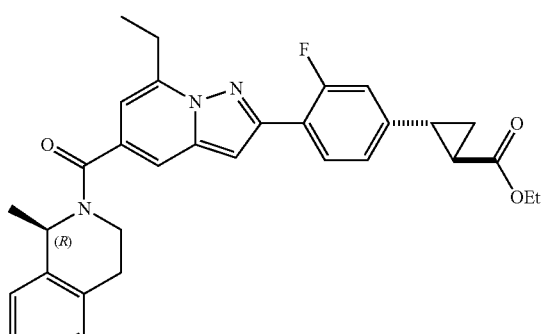

B15
(trans)

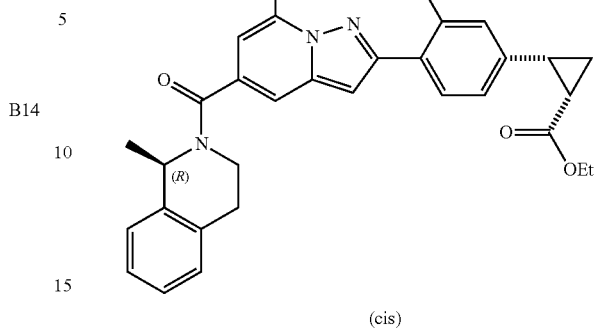

B16
(cis)

A mixture of intermediate B14 (249 mg, 567 µmol), copper iodide (43.2 mg, 227 µmol) and palladium acetate (25.4 mg, 113 µmol) in DCE (3 mL) was stirred at 80° C. Ethyl diazoacetate [623-73-4] (85% purity, 0.42 mL, 3.40 mmol) was added with a syringe pump over 2 h and the reaction mixture was stirred at 80° C. for 18 h. The reaction mixture was filtered over a pad of Celite®. The filtrate was evaporated in vacuo. The crude mixture was purified by preparative LC (irregular SiOH, 15-40 µm, 80 g GraceResolv™, liquid injection (DCM), mobile phase gradient: heptane/EtOAc from 100:0 to 50:50) to afford intermediate B15 (33 mg, 11%) as a white foam and intermediate B16 (30 mg, 10%) as a colorless gum.

Compound 4

Trans-2-(4-{7-ethyl-5-[(1R)-1-methyl-1,2,3,4-tetrahydroisoquinoline-2-carbonyl]pyrazolo[1,5-a]pyridin-2-yl}-3-fluorophenyl)cyclopropane-1-carboxylic Acid

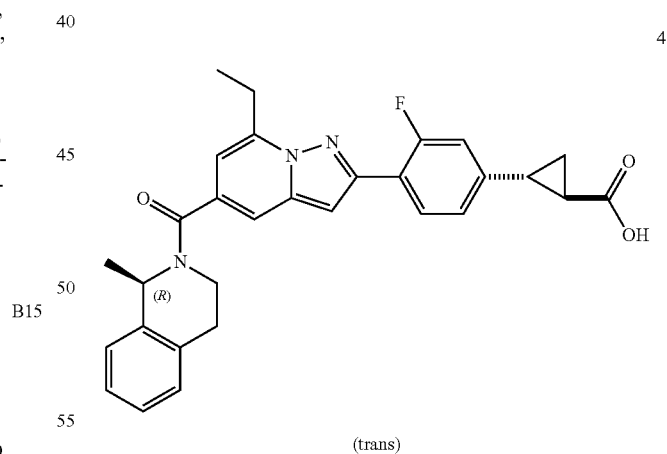

4
(trans)

Lithium hydroxide monohydrate (13.3 mg, 318 µmol) was added to a solution of intermediate B15 (33.0 mg, 62.8 µmol) in THF (1.8 mL) and H₂O (0.75 mL). The reaction mixture was stirred at rt for 18 h and at 50° C. for another 18 h. A 10% aqueous solution of KHSO₄ was added until pH 6 and the aqueous phase was extracted with EtOAc. The combined organic extracts were washed with H₂O, dried over MgSO₄, filtered and evaporated in vacuo. The residue was diluted in H₂O and MeCN (1:1) and freeze-dried to give compound 4 (23 mg, 74%) as a white solid.

Compound 5

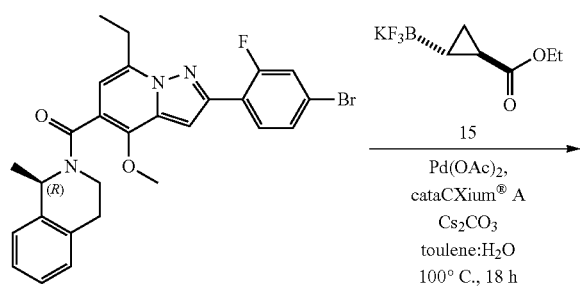

B10

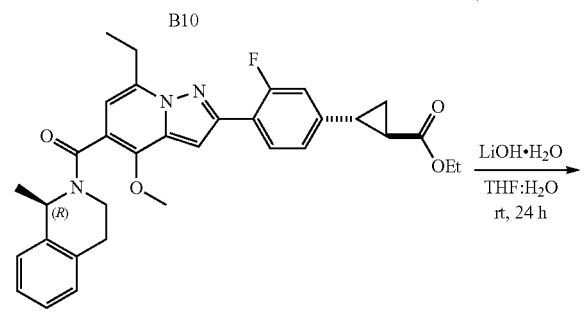

B17 (trans)

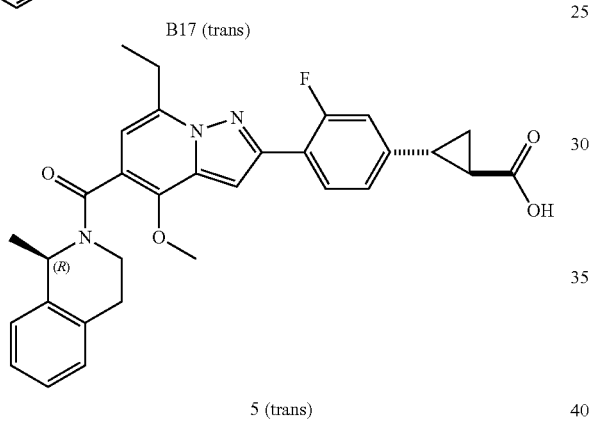

5 (trans)

Intermediate B17

Ethyl trans-2-(4-{7-ethyl-4-methoxy-5-[(1R)-1-methyl-1,2,3,4-tetrahydroisoquinoline-2-carbonyl]pyrazolo[1,5-a]pyridin-2-yl}-3-fluorophenyl)cyclopropane-1-carboxylate

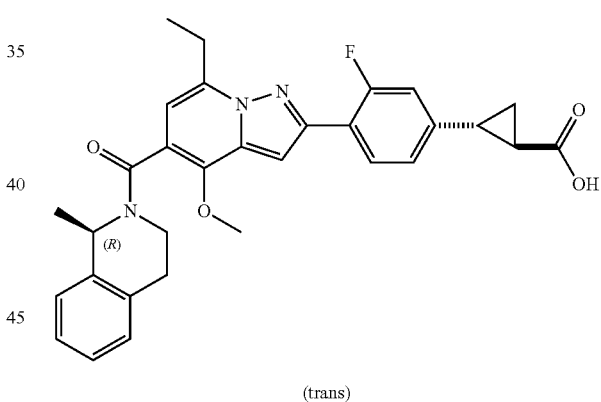

B17
(trans)

To a mixture of intermediate B10 (68.0 mg, 0.13 mmol), intermediate I5 (cis:trans 14:86, 29.5 mg, 0.13 mmol) and cesium carbonate (118 mg, 0.36 mmol) in toluene (1.5 mL) and H$_2$O (0.15 mL) was added cataCXium® A (10.8 mg, 30.2 μmol) and palladium acetate (4.92 mg, 2.19 μmol). The reaction mixture was purged with nitrogen and stirred at 100° C. for 18 h. The reaction mixture was diluted with H$_2$O and EtOAc. The layers were separated and the aqueous phase was extracted with EtOAc (twice). The combined organic extracts were dried over MgSO$_4$, filtered and evaporated in vacuo. The crude mixture was purified by preparative LC (irregular SiOH, 15-40 μm, 40 g Grace®, liquid injection (DCM), mobile phase gradient: heptane/EtOAc from 100:0 to 60:40) to afford intermediate B17 (43 mg, 60%) as a white foam.

Compound 5 trans-2-(4-{7-Ethyl-4-methoxy-5-[(1R)-1-methyl-1,2,3,4-tetrahydroisoquinoline-2-carbonyl]pyrazolo[1,5-a]pyridin-2-yl}-3-fluorophenyl)cyclopropane-1-carboxylic Acid

5

(trans)

Lithium hydroxide monohydrate (17.9 mg, 0.43 mmol) was added to a solution of intermediate B17 (43.0 mg, 77.4 μmol) in THF (2.4 mL) and H$_2$O (1 mL). The reaction mixture was stirred at rt for 24 h. A 10% aqueous solution of KHSO$_4$ was added until pH 6 and the aqueous phase was extracted with EtOAc. The combined organic extracts were washed with H$_2$O, dried over MgSO$_4$, filtered and evaporated in vacuo. The crude mixture was purified by reverse phase (spherical C18, 25 μm, 40 g YMC-ODS-25, liquid injection (MeCN), mobile phase gradient: 0.2% aq·NH$_4$HCO$_3$/MeCN from 75:25 to 35:65). The fractions containing the product were combined, concentrated and freeze-dried to give compound 5 (27 mg, 66%) as a white solid.

Compound 6

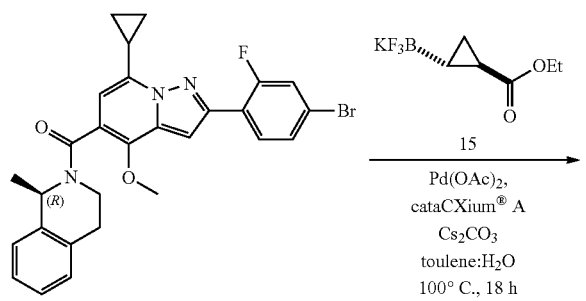

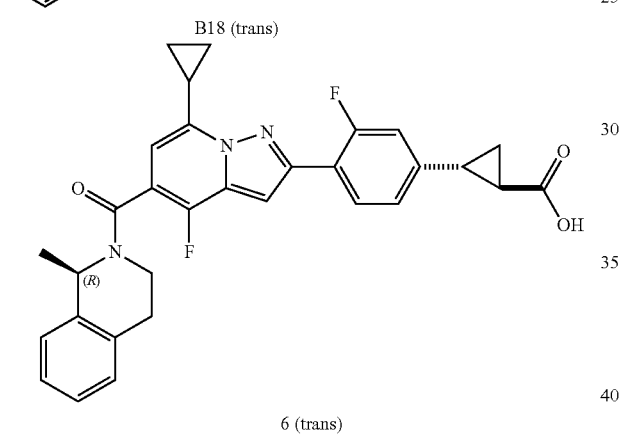

Intermediate I33

Ethyl trans-2-(4-{7-cyclopropyl-4-fluoro-5-[(1R)-1-methyl-1,2,3,4-tetrahydroisoquinoline-2-carbonyl]pyrazolo[1,5-a]pyridin-2-yl}-3-fluorophenyl)cyclopropane-1-carboxylate

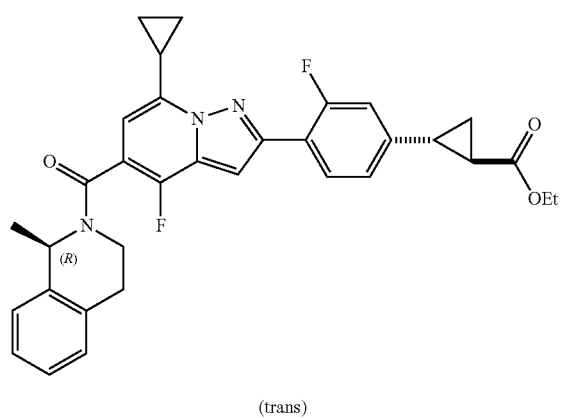

To a mixture of intermediate B13 (50.0 mg, 95.7 µmol), intermediate I5 (cis:trans 14:86, 42.1 mg, 0.19 mmol) and cesium carbonate (93.6 mg, 0.29 mmol) in toluene (1 mL) and H₂O (0.1 mL) were added cataCXium® A (8.24 mg, 23.0 µmol) and palladium acetate (3.44 mg, 15.3 µmol). The reaction mixture was purged with nitrogen and stirred at 100° C. for 18 h. The reaction mixture was diluted with H₂O and EtOAc. The layers were separated and the aqueous phase was extracted with EtOAc (twice). The combined organic extracts were dried over MgSO₄, filtered and evaporated in vacuo. The crude mixture was purified by preparative LC (irregular SiOH, 15-40 µm, 40 g Grace®, liquid injection (DCM), mobile phase gradient: heptane/EtOAc from 100:0 to 60:40) to afford intermediate B18 (36 mg, 68%) as an off-white solid.

Compound 6 trans-2-(4-{7-Cyclopropyl-4-fluoro-5-[(1R)-1-methyl-1,2,3,4-tetrahydroisoquinoline-2-carbonyl]pyrazolo[1,5-a]pyridin-2-yl}-3-fluorophenyl)cyclopropane-1-carboxylic Acid Lithium hydroxide monohydrate (15.0 mg, 0.36 mmol) was added to a solution of intermediate B18 (36.0 mg, 64.8 µmol) in THF (2 mL) and H₂O (0.9 mL). The reaction mixture was stirred at rt for 18 h. A 10% aqueous solution of KHSO₄ was added until pH 6 and the aqueous phase was extracted with EtOAc. The combined organic extracts were washed with H₂O, dried over MgSO₄, filtered and evaporated in vacuo. The residue was dissolved in MeCN and H₂O (1:1) and freeze-dried to give compound 6 (30 mg, 88%) as a white solid.

Compound 7

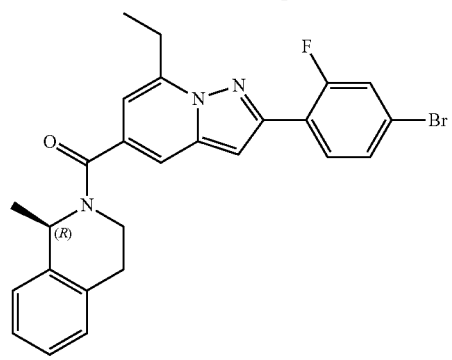
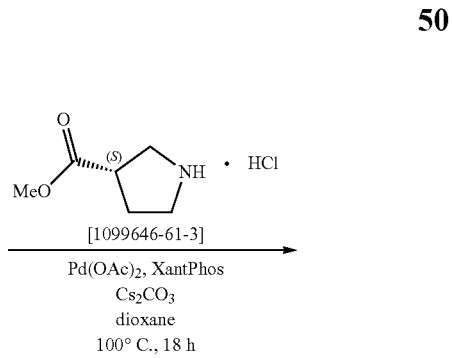

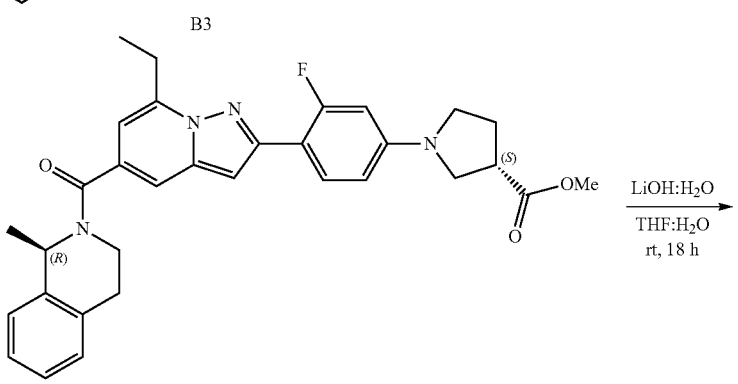

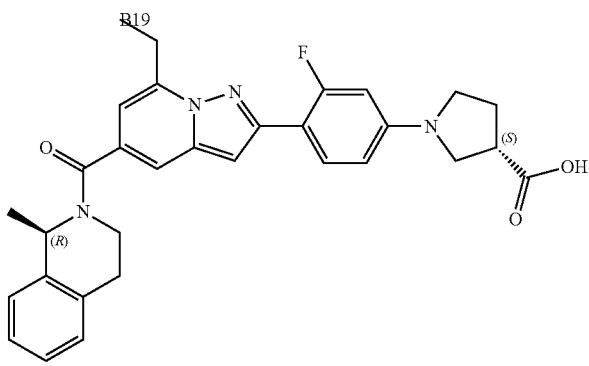

Intermediate I34

Methyl (3S)-1-(4-{7-cyclopropyl-5-[(1R)-1-methyl-1,2,3,4-tetrahydroisoquinoline-2-carbonyl]pyrazolo[1,5-a]pyridin-2-yl}-3-fluorophenyl)pyrrolidine-3-carboxylate

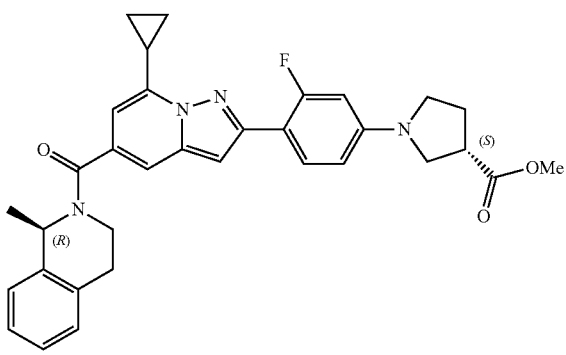

A sealed tube was charged with intermediate B3 (36.0 mg, 73.1 μmol), (S)-methyl pyrrolidine-3-carboxylate hydrochloride [1099646-61-3] (15.0 mg, 90.6 μmol), cesium carbonate (70.0 mg, 215 μmol) and XantPhos (5.00 mg, 8.64 μmol) and purged with nitrogen. 1,4-Dioxane (1.5 mL) was added and the mixture was purged again with nitrogen. Palladium acetate (2.00 mg, 8.91 μmol) was added. The reaction mixture was purged with nitrogen and stirred at 100° C. for 18 h. The reaction mixture was diluted with EtOAc and H₂O. The layers were separated and the aqueous phase was extracted with EtOAc (twice). The combined organic extracts were washed with brine, dried over MgSO₄, filtered and evaporated in vacuo. The crude mixture was purified by preparative LC (irregular SiOH, 15-40 μm, 24 g Grace®, liquid injection (DCM), mobile phase gradient: heptane/EtOAc from 90:10 to 50:50) to afford intermediate B19 (36 mg, 91%) as a white solid.

Compound 7

(3S)-1-(4-{7-Cyclopropyl-5-[(1R)-1-methyl-1,2,3,4-tetrahydroisoquinoline-2-carbonyl]pyrazolo[1,5-a]pyridin-2-yl}-3-fluorophenyl)pyrrolidine-3-carboxylic Acid

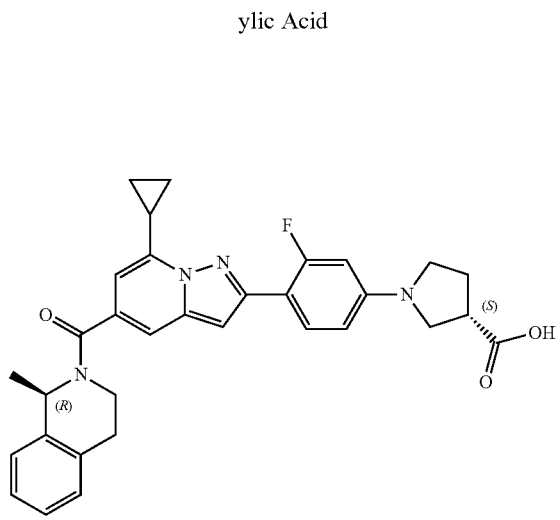

7

Lithium hydroxide monohydrate (15.0 mg, 0.36 mmol) was added to a solution of intermediate B19 (36.0 mg, 66.7 µmol) in THF (2 mL) and H₂O (1 mL). The reaction mixture was stirred at rt for 18 h. A 10% aqueous solution of KHSO₄ was added until pH was 6 and the aqueous phase was extracted with EtOAc. The combined organic extracts were washed with H₂O, dried over MgSO₄, filtered and evaporated in vacuo. The crude mixture was purified by preparative LC (spherical C18 25 µm, 40 g YMC-ODS-25, liquid injection (MeOH, H₂O), mobile phase gradient: 0.2% aq·NH₄HCO₃/MeCN from 90:10 to 50:50). The fractions containing the product were combined, concentrated and freeze-dried to give compound 7 (8 mg, 23%) as a pale pink solid.

Compound 8

(3S)-1-(4-{7-Cyclopropyl-5-[(1R)-1-methyl-1,2,3,4-tetrahydroisoquinoline-2-carbonyl]pyrazolo[1,5-a]pyridin-2-yl}-3-fluorophenyl)pyrrolidine-3-carboxamide

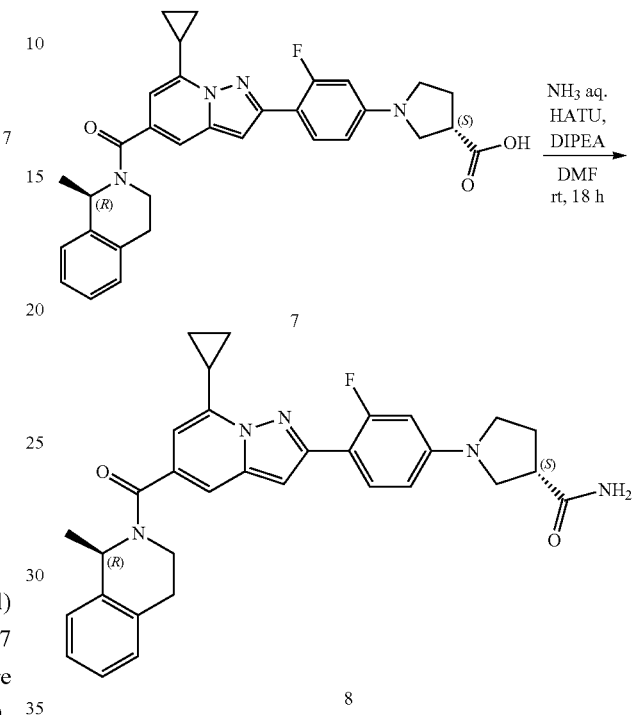

A mixture of compound 7 (100 mg, 0.19 mmol), HATU (108 mg, 0.29 mmol) and DIPEA (98 µL, 0.57 mmol) in DMF (3 mL) was stirred at rt for 1 h. Ammonia (28% in H₂O, 64 µL, 0.95 mmol) was added and the reaction mixture was stirred at rt for 18 h. The reaction mixture was diluted with H₂O and EtOAc. The layers were separated. The organic phase was washed with 1% aqueous solution of NaHCO₃, dried over MgSO₄, filtered and evaporated in vacuo. The crude mixture was purified by preparative LC (spherical C18 25 µm, 40 g YMC-ODS-25, solid loading (Celite®), mobile phase gradient: 0.2% aq·NH₄HCO₃/MeCN from 65:35 to 25:75). The fractions containing the product were combined, evaporated in vacuo and freeze-dried to give compound 8 (50 mg, 50%) as a yellow solid.

Compound 9

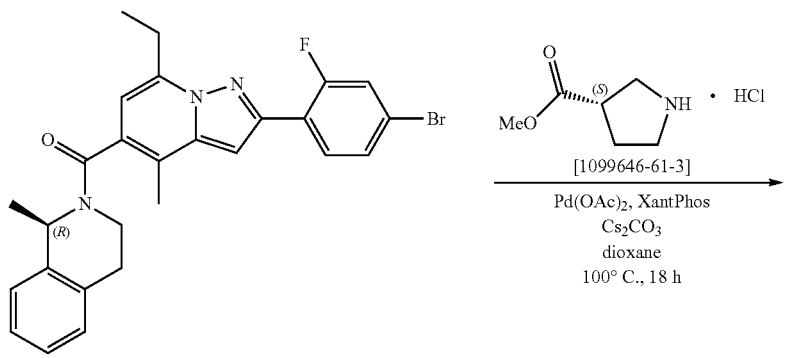

B6

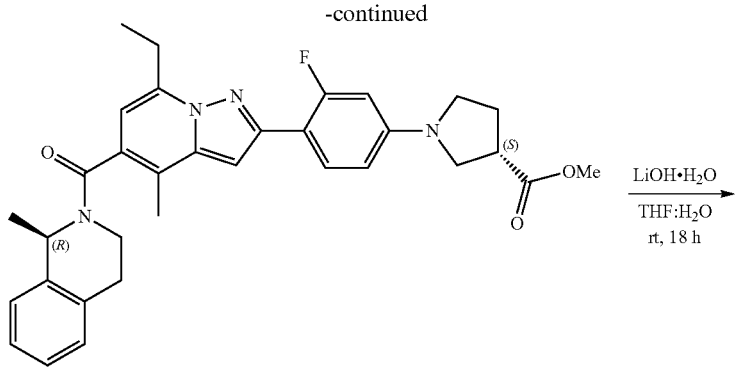

Intermediate I35

Methyl (3S)-1-(4-{7-ethyl-4-methyl-5-[(1R)-1-methyl-1,2,3,4-tetrahydroisoquinoline-2-carbonyl]pyrazolo[1,5-a]pyridin-2-yl}-3-fluorophenyl)pyrrolidine-3-carboxylate

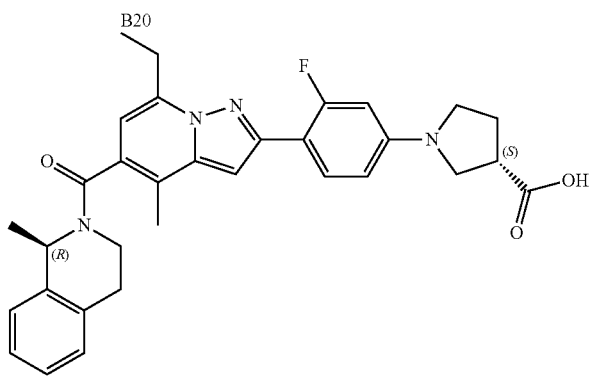

A sealed tube was charged with intermediate B6 (75.0 mg, 148 μmol), (S)-methyl pyrrolidine-3-carboxylate hydrochloride [1099646-61-3] (30.4 mg, 183 μmol), cesium carbonate (142 mg, 435 μmol) and XantPhos (10.1 mg, 17.5 μmol) and purged with nitrogen. 1,4-Dioxane (3 mL) was added and the mixture was purged again with nitrogen. Palladium acetate (4.05 mg, 18.0 μmol) was added. The reaction mixture was purged with nitrogen and stirred at 100° C. for 18 h. The reaction mixture was diluted with EtOAc and H₂O. The layers were separated and the aqueous phase was extracted with EtOAc (twice). The combined organic extracts were washed with brine, dried over MgSO₄, filtered and evaporated in vacuo. The crude mixture was purified by preparative LC (irregular SiOH, 15-40 μm, 50 g Merck, liquid injection (DCM), mobile phase gradient: heptane/EtOAc from 100:0 to 50:50) to afford intermediate B20 (59 mg, 72%) as a white solid.

Compound 9

(3S)-1-(4-{7-Ethyl-4-methyl-5-[(1R)-1-methyl-1,2,3,4-tetrahydroisoquinoline-2-carbonyl]pyrazolo[1,5-a]pyridin-2-yl}-3-fluorophenyl)pyrrolidine-3-carboxylic Acid

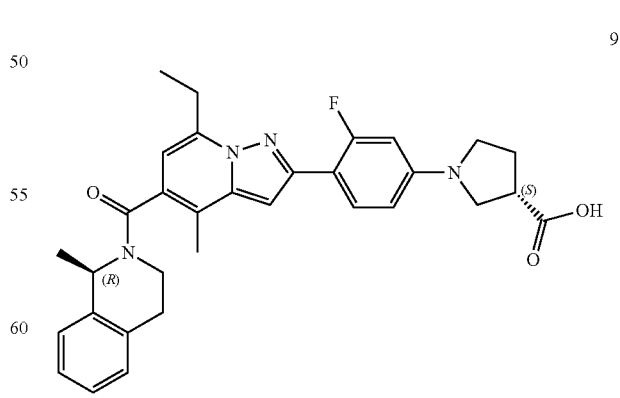

Lithium hydroxide monohydrate (24.6 mg, 0.59 mmol) was added to a solution of intermediate B20 (59.0 mg, 106 μmol) in THF (3.3 mL) and H₂O (1.4 mL). The reaction mixture was stirred at rt for 18 h. A 10% aqueous solution of KHSO₄ was added until pH 6 and the aqueous phase was extracted with EtOAc. The combined organic extracts were washed with H₂O, dried over MgSO₄, filtered and evaporated in vacuo. The crude mixture was purified by reverse phase (spherical C18, 25 μm, 40 g YMC-ODS-25, liquid injection (MeCN, MeOH, H₂O), mobile phase gradient: 0.2% aq·NH₄HCO₃/MeCN from 75:25 to 35:65). The fractions containing the product were combined, concentrated in vacuo and freeze-dried to give compound 9 (46 mg, 80%) as a white solid.

Compound 10

Intermediate B21

Methyl (3S)-1-(4-{7-cyclopropyl-4-fluoro-5-[(1R)-1-methyl-1,2,3,4-tetrahydroisoquinoline-2-carbonyl]pyrazolo[1,5-a]pyridin-2-yl}-3-fluorophenyl)pyrrolidine-3-carboxylate

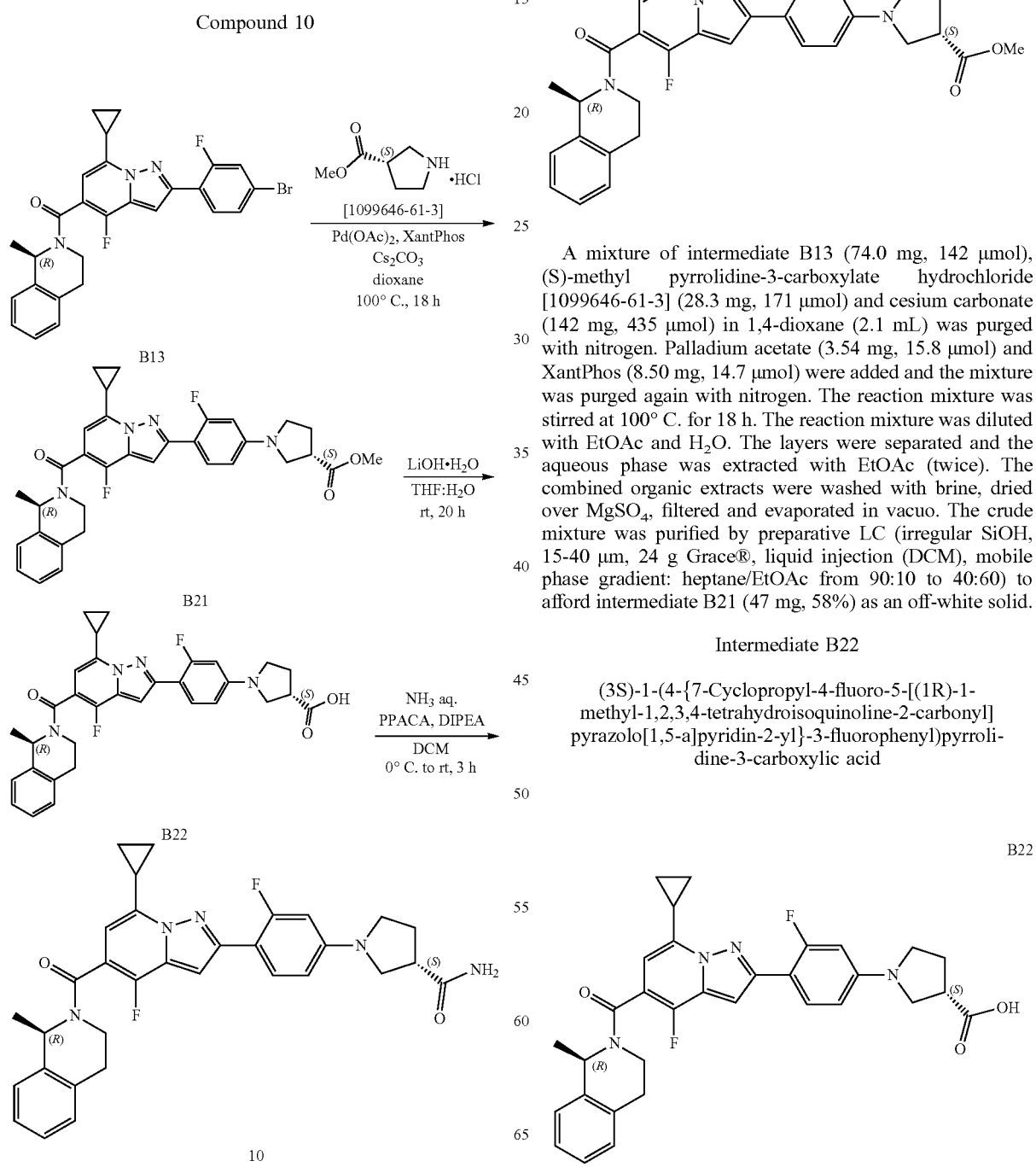

A mixture of intermediate B13 (74.0 mg, 142 μmol), (S)-methyl pyrrolidine-3-carboxylate hydrochloride [1099646-61-3] (28.3 mg, 171 μmol) and cesium carbonate (142 mg, 435 μmol) in 1,4-dioxane (2.1 mL) was purged with nitrogen. Palladium acetate (3.54 mg, 15.8 μmol) and XantPhos (8.50 mg, 14.7 μmol) were added and the mixture was purged again with nitrogen. The reaction mixture was stirred at 100° C. for 18 h. The reaction mixture was diluted with EtOAc and H₂O. The layers were separated and the aqueous phase was extracted with EtOAc (twice). The combined organic extracts were washed with brine, dried over MgSO₄, filtered and evaporated in vacuo. The crude mixture was purified by preparative LC (irregular SiOH, 15-40 μm, 24 g Grace®, liquid injection (DCM), mobile phase gradient: heptane/EtOAc from 90:10 to 40:60) to afford intermediate B21 (47 mg, 58%) as an off-white solid.

Intermediate B22

(3S)-1-(4-{7-Cyclopropyl-4-fluoro-5-[(1R)-1-methyl-1,2,3,4-tetrahydroisoquinoline-2-carbonyl]pyrazolo[1,5-a]pyridin-2-yl}-3-fluorophenyl)pyrrolidine-3-carboxylic acid Lithium hydroxide monohydrate (18.3 mg, 437 μmol) was added to a solution of intermediate B21 (45.0 mg, 78.9 μmol) in THF (0.6 mL) and H₂O (0.2 mL). The reaction mixture was stirred at rt for 20 h. A 10% aqueous solution of KHSO₄ was added until pH 6 and the aqueous phase was extracted with EtOAc. The combined organic extracts were washed with H₂O, dried over MgSO₄, filtered and evaporated in vacuo to afford intermediate B22 (43 mg, 98%) as a white solid.

Compound 10

(3S)-1-(4-{7-Cyclopropyl-4-fluoro-5-[(1R)-1-methyl-1,2,3,4-tetrahydroisoquinoline-2-carbonyl]pyrazolo[1,5-a]pyridin-2-yl}-3-fluorophenyl)pyrrolidine-3-carboxamide

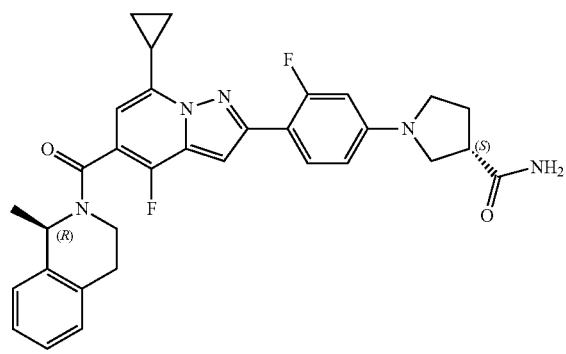

A mixture of intermediate B22 (43.0 mg, 77.3 μmol) and DIPEA (70 μL, 406 μmol) in DCM (1 mL) was stirred at 0° C. PPACA (50 wt. % in EtOAc, 0.12 mL, 202 μmol) was added slowly at 0° C. The reaction mixture was stirred at rt for 30 min. Ammonia (28% in H₂O, 25 μL, 371 μmol) was added and the mixture was stirred at rt for 3 h. The reaction mixture was diluted with H₂O and EtOAc. The layers were separated and the aqueous phase was extracted with EtOAc. The combined organic extracts were washed with a 10% aqueous solution of KHSO₄ and brine, dried over MgSO₄, filtered and evaporated in vacuo. The crude mixture was purified by reverse phase (spherical C18, 25 μm, 40 g YMC-ODS-25, liquid injection (MeCN, MeOH, H₂O), mobile phase gradient: 0.2% aq·NH₄HCO₃/MeCN from 90:10 to 25:75). The fractions containing the product were combined and diluted with EtOAc. A 10% aqueous solution of KHSO₄ was added. The layers were separated and the aqueous phase was extracted with EtOAc. The combined organic extracts were washed with brine, dried over MgSO₄, filtered and evaporated in vacuo. The residue was diluted with MeCN and H₂O (1:1) and freeze-dried to give compound 10 (17 mg, 40%) as a white solid.

Triazolopyridines

Synthesis of the Triazolopyridine Intermediates

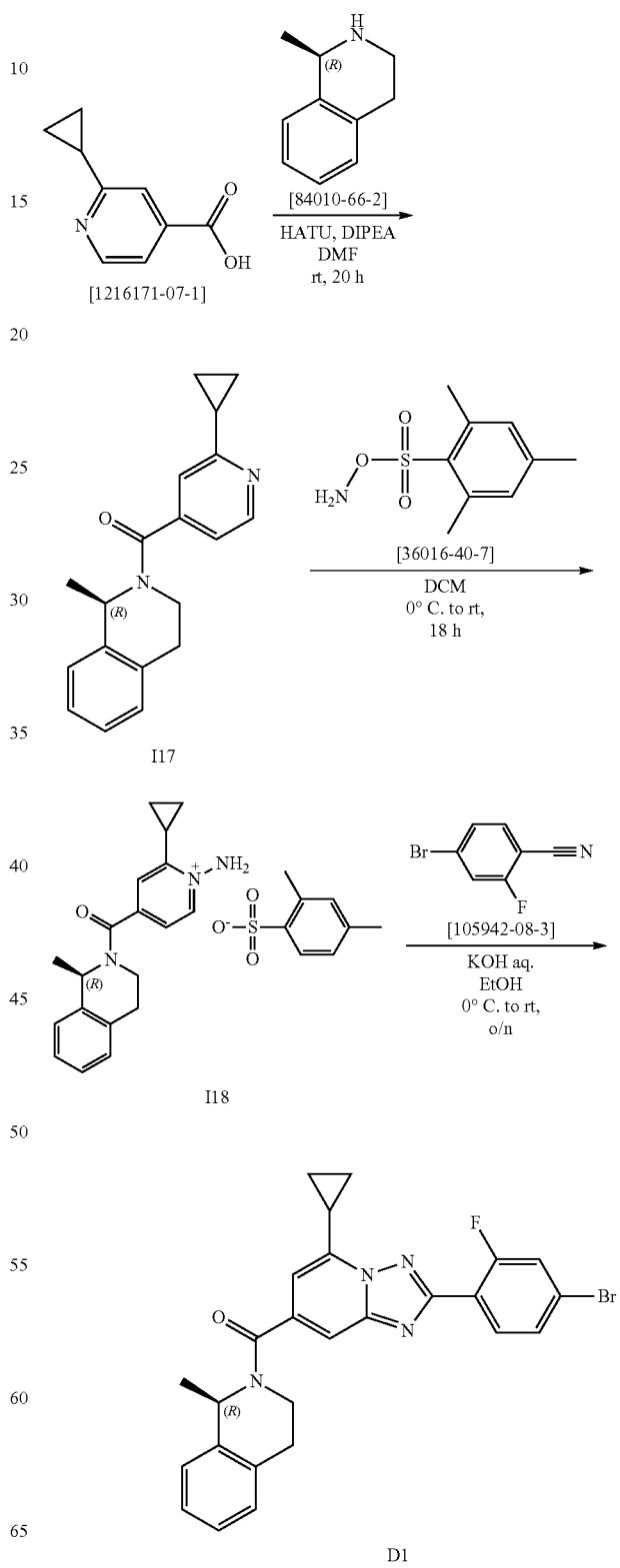

Intermediate I17

(1R)-2-(2-Cyclopropylpyridine-4-carbonyl)-1-methyl-1,2,3,4-tetrahydroisoquinoline

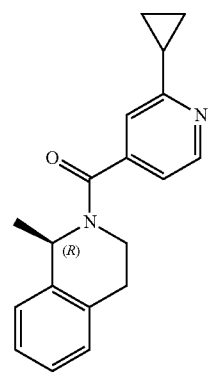

I17

A mixture of 2-cyclopropylpyridine-4-carboxylic acid [1216171-07-1] (730 mg, 4.47 mmol), (1R)-1-methyl-1,2,3,4-tetrahydroisoquinoline [84010-66-2] (790 mg, 5.37 mmol), HATU (2.21 g, 5.82 mmol) and DIPEA (2.3 mL, 13.4 mmol) in DMF (26 mL) was stirred at rt for 20 h. The reaction mixture was diluted with H$_2$O and EtOAc. The layers were separated and the aqueous phase was extracted twice with EtOAc. The combined organic extracts were washed with brine (4 times), dried over MgSO$_4$, filtered and evaporated in vacuo. The crude mixture was purified by preparative LC (irregular SiOH, 15-40 μm, 40 g GraceResolv™, liquid injection (DCM), mobile phase gradient: heptane/EtOAc from 70:30 to 20:80) to afford intermediate I17 (1.25 g, 96%) as a colorless oil.

Intermediate I18

1-Amino-2-cyclopropyl-4-[(1R)-1-methyl-1,2,3,4-tetrahydroisoquinoline-2-carbonyl]pyridin-1-ium 2,4,6-trimethylbenzene-1-sulfonate

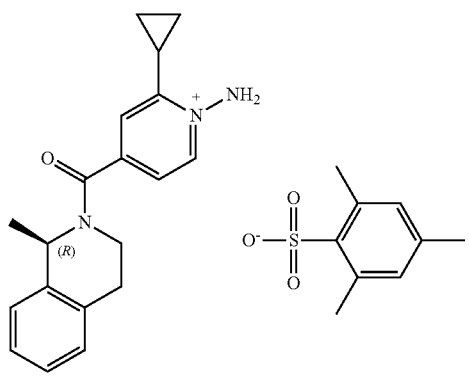

I18

To a suspension of o-(2,4,6-trimethylbenzenesulfonyl)hydroxylamine [36016-40-7] (1.46 g, 6.77 mmol) in DCM (12 mL) cooled with an ice bath was added dropwise a solution of intermediate I17 (1.80 g, 6.16 mmol) in DCM (3.6 mL). The reaction mixture was stirred at rt for 18 h. The reaction mixture was diluted with Et$_2$O until the formation of a precipitate was observed. The precipitate was filtered off and washed with Et$_2$O to give a first crop of intermediate I18 (2.5 g, 80%). The filtrate was concentrated in vacuo to afford a second crop of intermediate I18 (600 mg, 20%).

Intermediate D1

(1R)-2-[2-(4-Bromo-2-fluorophenyl)-5-cyclopropyl-[1,2,4]triazolo[1,5-a]pyridine-7-carbonyl]-1-methyl-1,2,3,4-tetrahydroisoquinoline

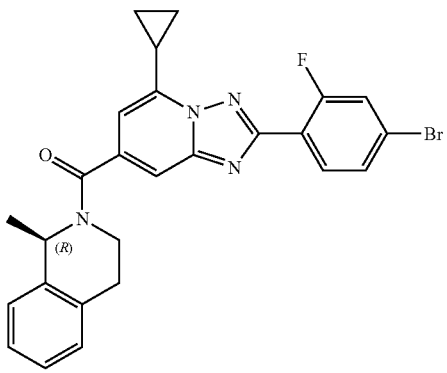

D1

A mixture of intermediate I18 (500 mg, 985 μmol) and 4-bromo-2-fluorobenzonitrile [105942-08-3] (217 mg, 1.08 mmol) in EtOH (10 mL) was cooled to 0° C. Potassium hydroxide (2.0 M in H$_2$O, 542 μL, 1.08 mmol) was added dropwise and the reaction mixture was stirred at rt overnight. Solvent was evaporated in vacuo. The residue was diluted with H$_2$O and DCM. The layers were separated and the aqueous phase was extracted with DCM (3 times). The combined organic extracts were dried over MgSO$_4$, filtered and concentrated in vacuo. The crude mixture was purified by preparative LC (regular SiOH, 30 μm, 40 g GraceResolv™, liquid injection (DCM), mobile phase gradient: heptane/EtOAc from 80:20 to 50:50) to give intermediate D1 (87 mg, 17% as a white foam.

Synthesis of Final Compounds
Compounds 16 and 17
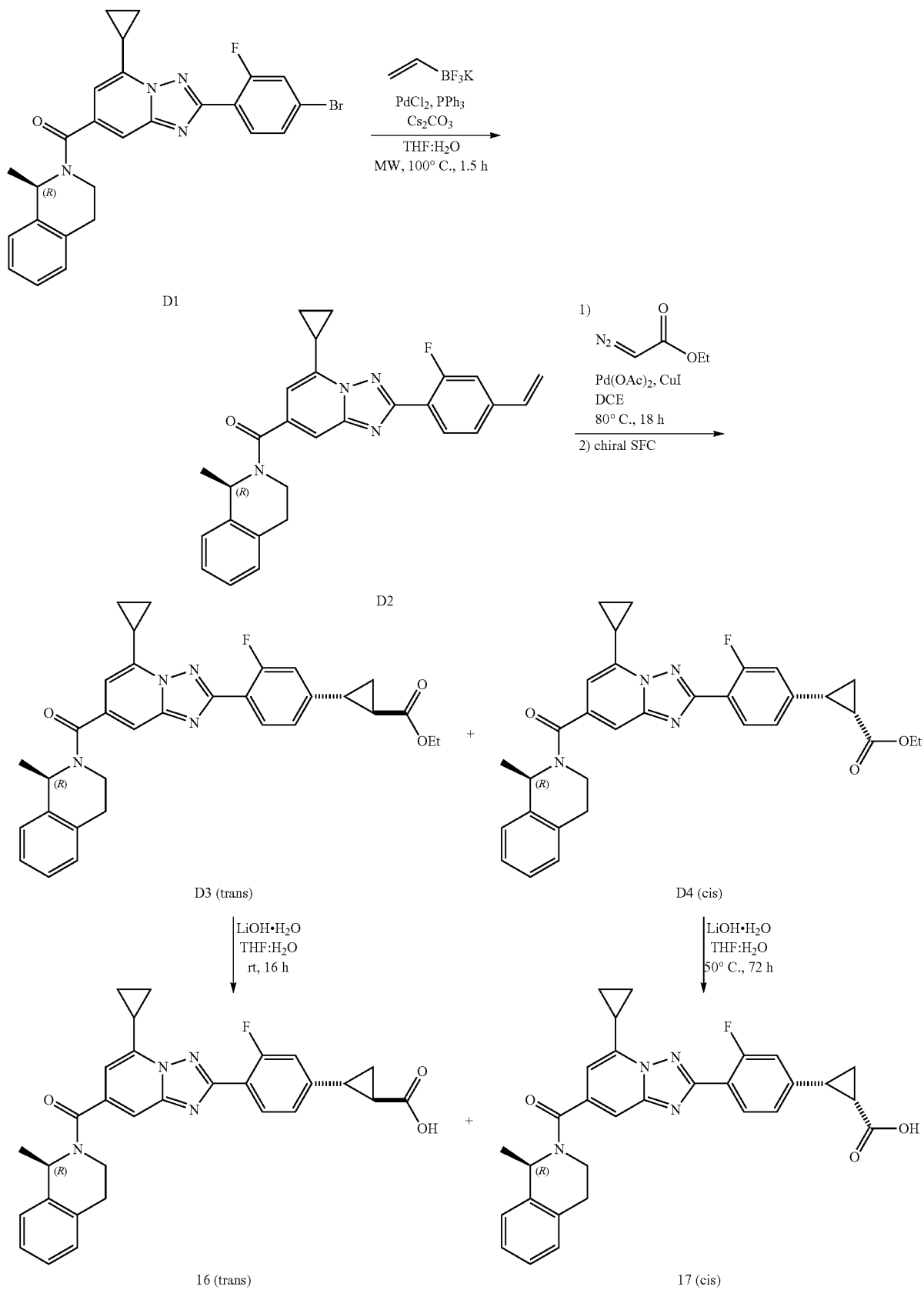
16 (trans)        17 (cis)

Intermediate D2

(1R)-2-[5-Cyclopropyl-2-(4-ethenyl-2-fluorophenyl)-[1,2,4]triazolo[1,5-a]pyridine-7-carbonyl]-1-methyl-1,2,3,4-tetrahydroisoquinoline

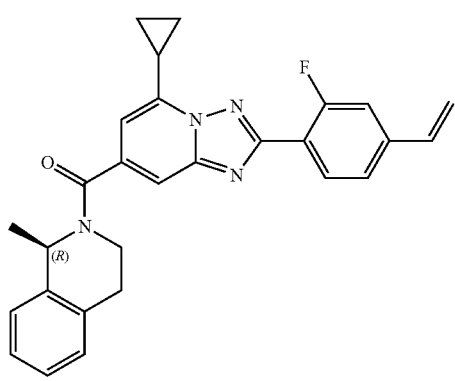

D2

Palladium chloride (1.82 mg, 10.3 μmol) was added to a degassed mixture of intermediate D1 (116 mg, 0.23 mmol), potassium vinyltrifluoroborate [13682-77-4] (92.2 mg, 0.69 mmol), cesium carbonate (325 mg, 1.00 mmol) and triphenylphosphine (8.05 mg, 30.7 μmol) in THF and H₂O (9:1, 3.5 mL). The reaction mixture was heated at 100° C. using a single mode microwave (Biotage® Initiator EXP 60) with a power output ranging from 0 to 400 W for 1.5 h. The reaction mixture was diluted with EtOAc and H₂O. The layers were separated and the organic phase was washed with H₂O, dried over MgSO₄, filtered and concentrated in vacuo. The crude mixture was purified by preparative LC (regular SiOH, 30 μm, 12 g GraceResolv™, liquid injection (DCM), mobile phase gradient: heptane/EtOAc from 90:10 to 40:60) to afford intermediate D2 (83 mg, 80%) as a yellow solid.

Intermediate D3 and D4

D3: Ethyl trans-2-(4-{5-cyclopropyl-7-[(1R)-1-methyl-1,2,3,4-tetrahydroisoquinoline-2-carbonyl]-[1,2,4]triazolo[1,5-a]pyridin-2-yl}-3-fluorophenyl)cyclopropane-1-carboxylate D4: Ethyl cis-2-(4-{5-cyclopropyl-7-[(1R)-1-methyl-1,2,3,4-tetrahydroisoquinoline-2-carbonyl]-[1,2,4]triazolo[1,5-a]pyridin-2-yl}-3-fluorophenyl)cyclopropane-1-carboxylate

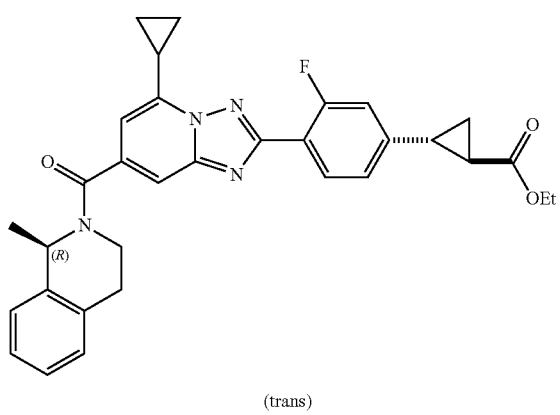

D3 (trans)

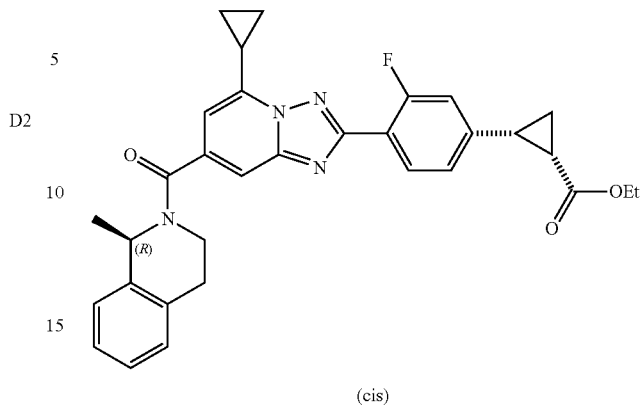

D4 (cis)

A mixture of intermediate D2 (225 mg, 497 μmol), copper (I) iodide (9.47 mg, 49.7 μmol), palladium acetate (11.2 mg, 49.7 μmol) in DCE (4.0 mL) was stirred at 80° C. and ethyl diazoacetate (0.37 mL, 2.98 mmol, 85% purity) in DCE (1.6 mL) was added with a syringe pump over 4 h. The reaction mixture was stirred at 80° C. for 18 h. The reaction mixture was filtered over a pad of Celite® and the filtrate was concentrated in vacuo. The crude mixture (140 mg) was combined with another fraction (81 mg) and purified by preparative LC (irregular SiOH, 15-40 μm, 220 g GraceResolv™, liquid injection (DCM), mobile phase gradient: heptane/EtOAc from 70:30 to 40:60) to afford intermediate D3 (65 mg, 18%) and intermediate D4 (45 mg, 12%) as colorless oils.

Compound 16 trans-2-(4-{5-Cyclopropyl-7-[(1R)-1-methyl-1,2,3,4-tetrahydroisoquinoline-2-carbonyl]-[1,2,4]triazolo[1,5-a]pyridin-2-yl}-3-fluorophenyl)cyclopropane-1-carboxylic Acid

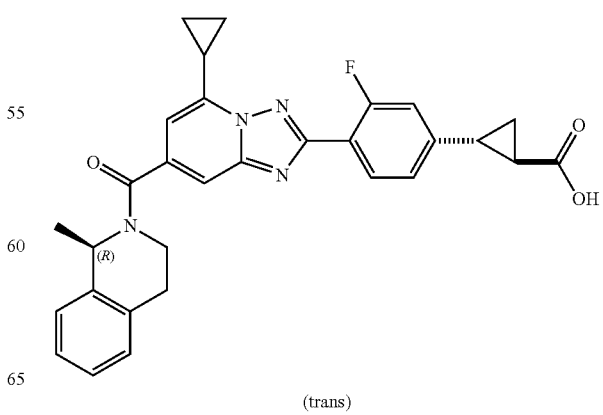

16 (trans)

Lithium hydroxide monohydrate (15.2 mg, 0.36 mmol) was added to a solution of intermediate D3 (65.0 mg, 0.12 mmol) in THF (1.1 mL) and H$_2$O (0.3 mL). The reaction mixture was stirred at rt for 16 h. A 10% aqueous solution of KHSO$_4$ was added until pH 6 and the aqueous phase was extracted with EtOAc. The combined organic extracts were washed with H$_2$O, dried over MgSO$_4$, filtered and concentrated in vacuo. The crude mixture was purified by preparative LC (irregular SiOH, 15-40 µm, 12 g GraceResolv™, liquid injection (DCM), mobile phase gradient: heptane/EtOAc/AcOH from 80:19.5:0.5 to 40:58.5:1.5) to give compound 16 (42 mg, 68%).

Compound 17 cis-2-(4-{5-Cyclopropyl-7-[(1R)-1-methyl-1,2,3,4-tetrahydroisoquinoline-2-carbonyl]-[1,2,4]triazolo[1,5-a]pyridin-2-yl}-3-fluorophenyl)cyclopropane-1-carboxylic Acid

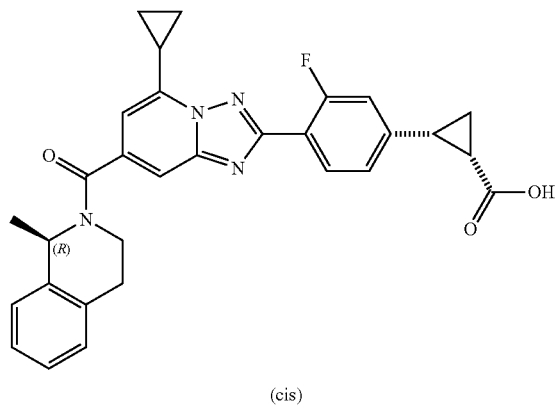

Lithium hydroxide monohydrate (11.0 mg, 0.25 mmol) was added to a solution of intermediate D4 (45.0 mg, 83.5 µmol) in THF (1 mL) and H$_2$O (0.3 mL). The reaction mixture was stirred at rt for 16 h. An additional amount of lithium hydroxide monohydrate (11.0 mg, 0.25 mmol) was added and the reaction mixture was stirred at 50° C. for 72 h. A 10% aqueous solution of KHSO$_4$ was added until pH 6 and the aqueous phase was extracted with EtOAc. The combined organic extracts were washed with H$_2$O, dried over MgSO$_4$, filtered and concentrated in vacuo. The crude mixture was purified by preparative LC (irregular SiOH, 15-40 µm, 12 g GraceResolv™, liquid injection (DCM), mobile phase gradient: heptane/EtOAc/AcOH from 80:19.5:0.5 to 40:58.5:1.5) to give compound 17 (33 mg, 77%).

Compound 18 trans-2-(4-{5-Cyclopropyl-7-[(1R)-1-methyl-1,2,3,4-tetrahydroisoquinoline-2-carbonyl]-[1,2,4]triazolo[1,5-a]pyridin-2-yl}-3-fluorophenyl)cyclopropane-1-carboxamide

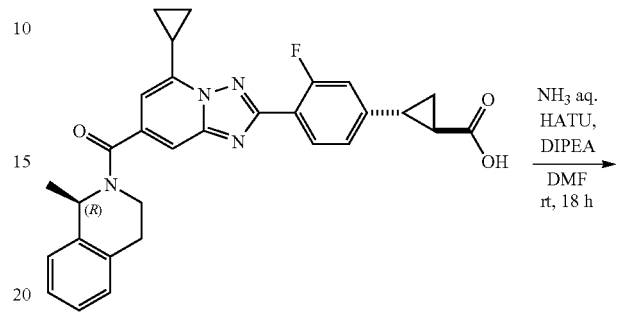

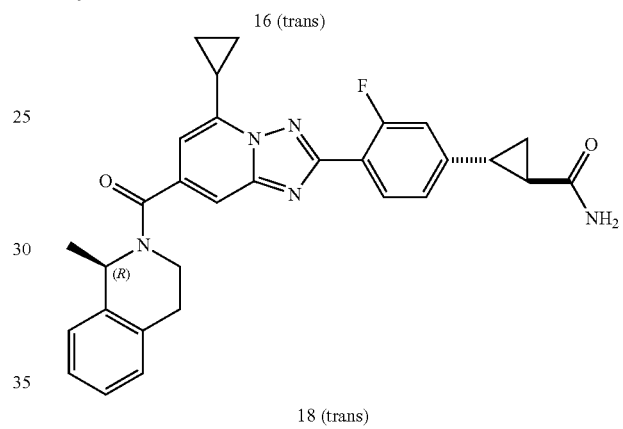

A mixture of compound 16 (18.0 mg, 35.3 µmol), HATU (20.1 mg, 52.9 µmol) and DIPEA (18 µL, 106 µmol) in DMF (1 mL) was stirred at rt for 1 h. Ammonia (28% in H$_2$O, 12 µL, 176 µmol) was added and the reaction mixture was stirred at rt for 18 h. The reaction mixture was diluted with H$_2$O and EtOAc. The layers were separated and the organic phase was washed with 1% aqueous solution of NaHCO$_3$ (twice), dried over MgSO$_4$, filtered and evaporated in vacuo. The crude mixture was purified by preparative LC (regular SiOH, 30 µm, 12 g GraceResolv™, liquid injection (DCM), mobile phase gradient: DCM/i-PrOH from 100:0 to 80:20). The residue was freeze-dried (MeCN/H$_2$O) to give compound 18 (11 mg, 61%) as a white solid.

Compound 19

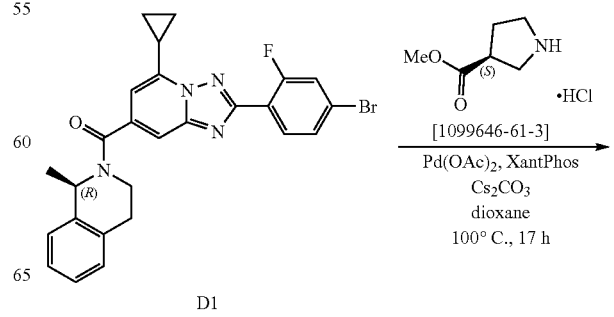

-continued

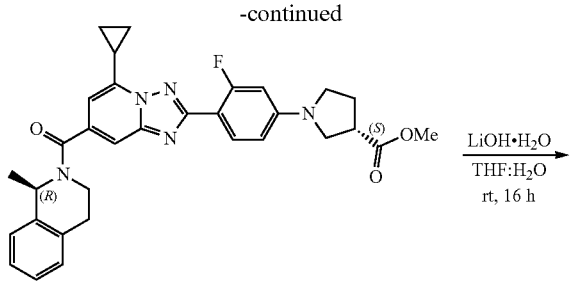

D5

Intermediate D5

Methyl (3S)-1-(4-{5-cyclopropyl-7-[(1R)-1-methyl-1,2,3,4-tetrahydroisoquinoline-2-carbonyl]-[1,2,4]triazolo[1,5-a]pyridin-2-yl}-3-fluorophenyl)pyrrolidine-3-carboxylate

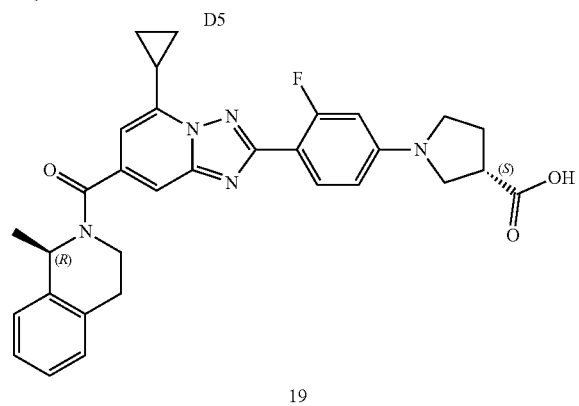

D5

A sealed tube was charged with intermediate D1 (85 mg; 168 μmol), (S)-methyl pyrrolidine-3-carboxylate hydrochloride [1099646-61-3] (33.4 mg, 0.20 mmol), cesium carbonate (164 mg, 505 μmol) and XantPhos (9.73 mg, 16.8 μmol) and purged with nitrogen. 1,4-Dioxane (2.5 mL) was added and the mixture was purged again with nitrogen. Palladium acetate (3.78 mg, 16.8 μmol) was added and the mixture was purged with nitrogen. The reaction mixture was stirred at 100° C. for 17 h. The reaction mixture was diluted with EtOAc and H₂O. The layers were separated and the aqueous phase was extracted with EtOAc (twice). The combined organic extracts were washed with brine, dried over MgSO₄, filtered and the solvent was evaporated in vacuo. The crude mixture was purified by preparative LC (irregular SiOH, 15-40 μm, 12 g Grace®, liquid injection (DCM), mobile phase gradient: heptane/EtOAc from 90:10 to 20:80) to afford intermediate D5 (82 mg, 88%) as a yellow oil.

Compound 19

(3S)-1-(4-{5-Cyclopropyl-7-[(1R)-1-methyl-1,2,3,4-tetrahydroisoquinoline-2-carbonyl]-[1,2,4]triazolo[1,5-a]pyridin-2-yl}-3-fluorophenyl)pyrrolidine-3-carboxylic Acid

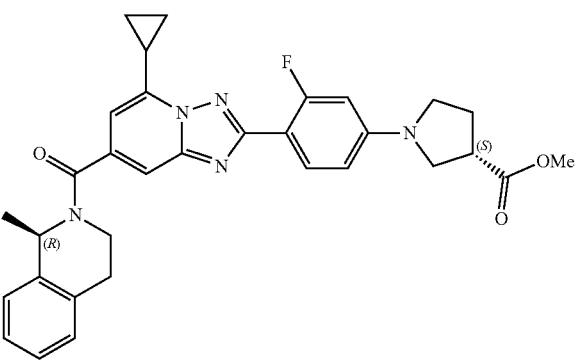

19

Lithium hydroxide monohydrate (18.6 mg, 0.44 mmol) was added to a solution of intermediate D5 (82.0 mg, 14.8 μmol) in THF (1.86 mL) and H₂O (580 μL). The reaction mixture was stirred at rt for 16 h. A 10% aqueous solution of KHSO₄ was added until pH 6 and the aqueous phase was extracted with EtOAc. The combined organic extracts were washed with H₂O, dried over MgSO₄, filtered and concentrated in vacuo. The crude mixture was purified twice by preparative LC (irregular SiOH, 15-40 μm, 12 g GraceResolv™, liquid injection (DCM), mobile phase gradient: heptane/EtOAc/AcOH from 80:20:0.5 to 0:97.5:2.5). The residue was co-evaporated with MeCN and dried under vacuum at 50° C. for 16 h to give an oil (60 mg, 96% purity). A third purification was performed by preparative LC (spherical C18 25 μm, 40 g YMC-ODS-25, dry loading (Celite®), mobile phase gradient: 0.2% aq·NH₄HCO₃/MeCN from 90:10 to 50:50). The product was taken up in MeCN to give compound 19 (48 mg, 60%) as a white solid.

Compound 20

(3S)-1-(4-{5-Cyclopropyl-7-[(1R)-1-methyl-1,2,3,4-tetrahydroisoquinoline-2-carbonyl]-[1,2,4]triazolo[1,5-a]pyridin-2-yl}-3-fluorophenyl)pyrrolidine-3-carboxamide

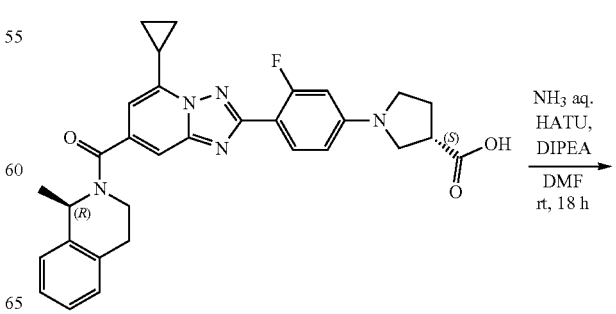

19

-continued

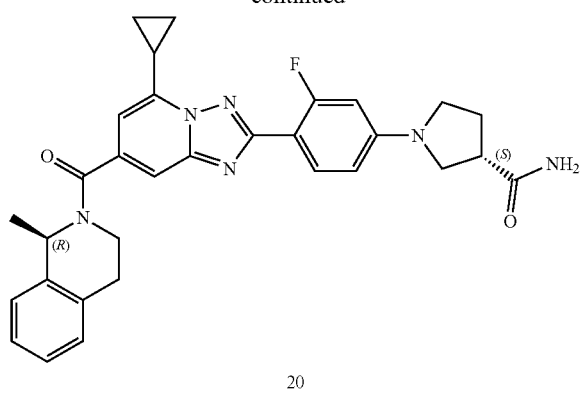

20

A mixture of compound 19 (180 mg, 334 µmol), HATU (190 mg, 500 µmol) and DIPEA (172 µL, 1.00 mmol) in DMF (9.2 mL) was stirred at rt for 1 h. Ammonia (28% in H₂O, 113 µL, 1.67 mmol) was added and the reaction mixture was stirred at rt for 18 h. The reaction mixture was diluted with H₂O and EtOAc. The layers were separated and the organic phase was washed with 1% aqueous solution of NaHCO₃ (twice), dried over MgSO₄, filtered and evaporated in vacuo. The crude mixture was purified by preparative LC (irregular SiOH, 30 µm, 12 g GraceResolv™, liquid injection (DCM), mobile phase gradient: DCM/i-PrOH from 100:0 to 80:20). The residue was taken up in EtOH and dried under vacuum at 50° C. for 16 h to give compound 20 (70 mg, 39%) as a white solid.

Pyrazolo[1,5-c]pyrimidines

Synthesis of the pyrazolo[1,5-c]pyrimidine Core

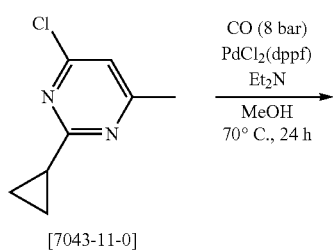

-continued

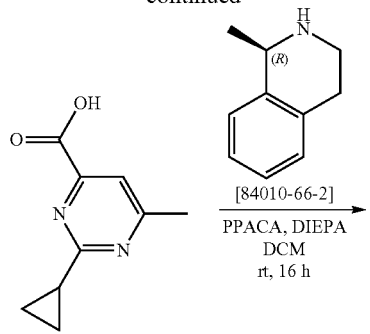

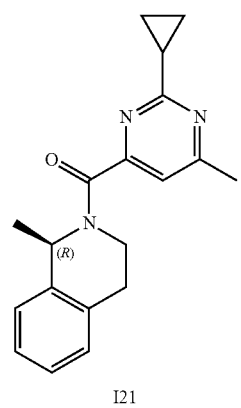

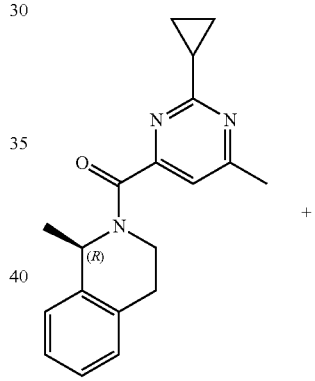

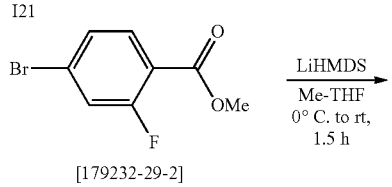

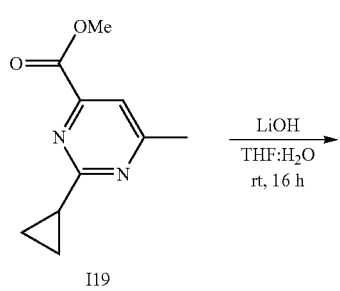

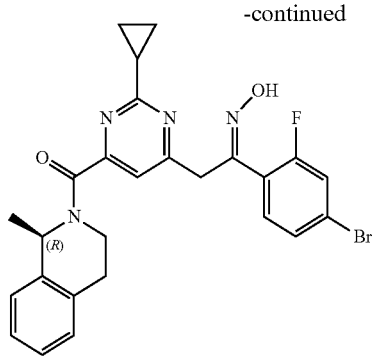

I23

1) TFAA, DME
0° C. to rt, 20 min
then Et₃N, 30 min
2) FeCl₂
80° C., 1 h

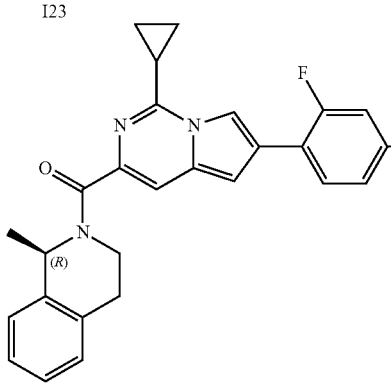

E1

Intermediate I19

Methyl 2-cyclopropyl-6-methylpyrimidine-4-carboxylate

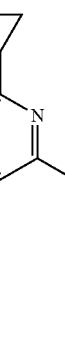

I19

In an autoclave, a mixture of 4-chloro-2-cyclopropyl-6-methylpyrimidine [7043-11-0] (1.00 g, 5.93 mmol) and Et₃N (1.6 mL, 11.8 mmol) in methanol (20 mL) was purged with nitrogen (3 times). [1,1'-Bis(diphenylphosphino)ferrocene]dichloropalladium (II) (217 mg, 297 µmol) was added. The mixture was purged with CO (3 times). The autoclave was pressurized with CO at 8 bars and the reaction mixture was stirred at 70° C. for 24 h. The reaction mixture was concentrated to dryness. The residue was diluted with DCM and H₂O. The layers were separated and the aqueous phase was extracted with DCM (twice). The combined organic extracts were dried over MgSO₄, filtered and concentrated to dryness. The crude mixture was purified by flash chromatography (irregular SiOH, 15-40 µm, 40 g GraceResolv™, dry loading (SiOH), mobile phase gradient: heptane/EtOAc from 90:10 to 40:60) to afford intermediate I19 (1.07 g, 94%) as a colorless oil.

Intermediate I20

2-Cyclopropyl-6-methylpyrimidine-4-carboxylic Acid

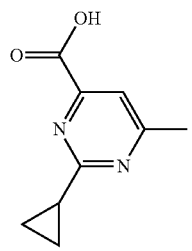

I20

Lithium hydroxide (266 mg, 11.1 mmol) was added to a solution of intermediate I19 (1.07 g, 5.57 mmol) in THF (36 mL) and H₂O (18 mL). The reaction mixture was stirred at rt for 16 h. A 10% aqueous solution of KHSO₄ was added until pH 3 and the mixture was diluted with EtOAc. The layers were separated and the organic phase was washed with brine and H₂O (twice), dried over MgSO₄, filtered and concentrated to dryness to afford intermediate I20 (678 mg, 68%) as a white solid.

Intermediate I21

(1R)-2-(2-Cyclopropyl-6-methylpyrimidine-4-carbonyl)-1-methyl-1,2,3,4-tetrahydroisoquinoline

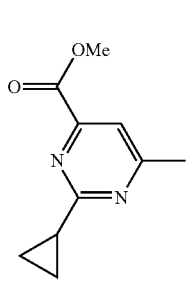

I21

PPACA [68957-94-8] (50 wt. % in DMF, 4.8 mL, 8.11 mmol) was added dropwise to a mixture of intermediate I20 (578 mg, 3.24 mmol) and (1R)-1-methyl-1,2,3,4-tetrahydroisoquinoline [84010-66-2] (554 mg, 3.76 mmol) at 0° C. A solution of DIPEA (2.8 mL, 16.2 mmol) in DCM (16 mL) was added and the reaction mixture was stirred at rt for 16 h. The reaction mixture was combined with another fraction (50 mg, 281 µmol) and diluted with EtOAc. The mixture was washed with a 1M aqueous solution of NaOH and brine (3 times), dried over MgSO₄, filtered and concentrated to dryness. The crude mixture was purified by preparative LC (irregular SiOH, 15-40 µm, 40 g GraceResolv™, liquid injection (DCM), mobile phase gradient: heptane/EtOAc from 80:20 to 30:70) to afford intermediate I21 (1.1 g) as a colorless oil.

Intermediate I22

1-(4-Bromo-2-fluorophenyl)-2-{2-cyclopropyl-6-[(1R)-1-methyl-1,2,3,4-tetrahydroisoquinoline-2-carbonyl]pyrimidin-4-yl}ethan-1-one

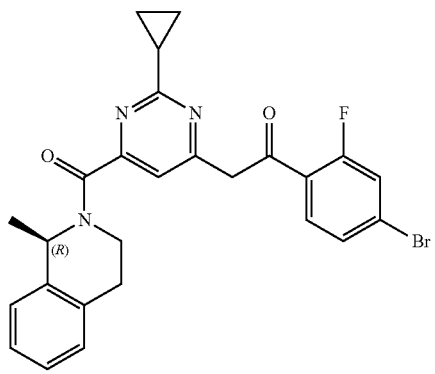

I22

Lithium bis(trimethylsilyl)amide (1.0 M in THF, 6.1 mL, 6.10 mmol) was added dropwise to a mixture of intermediate I21 (895 mg, 2.91 mmol) and methyl 4-bromo-2-fluorobenzoate [179232-29-2] (714 mg, 3.06 mmol) in 2-methyltetrahydrofuran (7.4 mL) at 0° C. The reaction mixture was left to warm up to rt and stirred at this temperature for 1.5 h. The reaction mixture was quenched by the addition of $H_2O$ at 0° C. The layers were separated and the aqueous phase was extracted with EtOAc (twice). The combined organic extracts were washed with brine, dried over $MgSO_4$, filtered and concentrated to dryness. The crude mixture was purified by flash chromatography (irregular SiOH, 15-40 μm, 40 g GraceResolv™, dry loading (SiOH), mobile phase gradient: heptane/EtOAc from 90:10 to 30:70) to afford intermediate I22 (1.38 g, 93%) as a yellow solid.

Intermediate I23

N-[1-(4-Bromo-2-fluorophenyl)-2-{2-cyclopropyl-6-[(1R)-1-methyl-1,2,3,4-tetrahydroisoquinoline-2-carbonyl]pyrimidin-4-yl}ethylidene]hydroxylamine

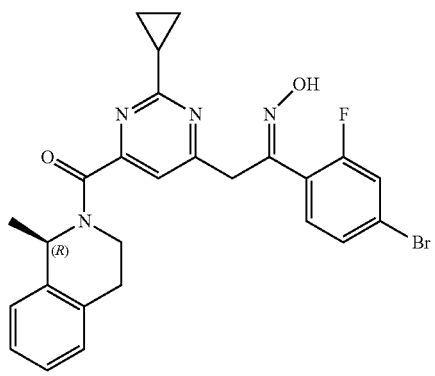

I23

Hydroxylamine hydrochloride (957 mg, 13.8 mmol) and acetic acid sodium salt (1.13 g, 13.8 mmol) were added to a suspension of intermediate I22 (1.40 g, 2.75 mmol) in MeCN (13 mL) and THF (13 mL). The reaction mixture was stirred at 70° C. for 20 h. The reaction mixture was diluted with $H_2O$ and EtOAc. The layers were separated and the organic phase was washed with brine (twice), dried over $MgSO_4$, filtered and concentrated to dryness. The crude mixture was purified by flash chromatography (irregular SiOH, 15-40 μm, 40 g GraceResolv™, dry loading (SiOH), mobile phase gradient: heptane/EtOAc from 90:10 to 20:80) to afford intermediate I23 (920 mg, 64%) as a yellow solid.

Intermediate E1

(1R)-2-[2-(4-Bromo-2-fluorophenyl)-7-cyclopropylpyrazolo[1,5-c]pyrimidine-5-carbonyl]-1-methyl-1,2,3,4-tetrahydroisoquinoline

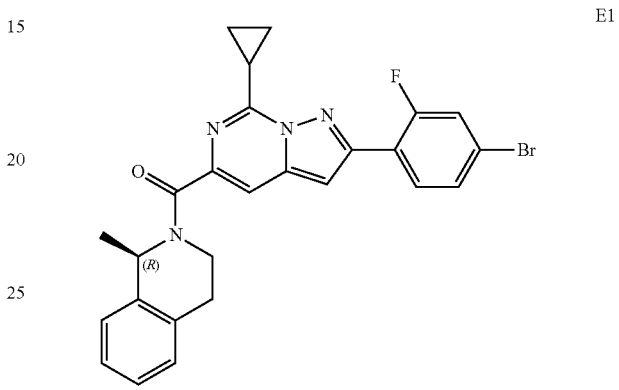

E1

Trifluoroacetic anhydride (244 μL, 1.76 mmol) was added dropwise to a solution of intermediate I23 (920 mg, 1.76 mmol) in DME (3.8 mL) at 0° C. The reaction mixture was warmed up to rt and stirred for 20 min. The mixture was cooled to 0° C. and $Et_3N$ (489 μL, 3.52 mmol) was added dropwise. The reaction mixture was warmed up to rt and stirred for 30 min. The mixture was cooled again to 0° C. and iron (II) chloride (223 mg, 1.76 mmol) was added. The reaction mixture was stirred at 80° C. for 1 h. The black mixture was quenched by the addition of a saturated aqueous solution of $NaHCO_3$ and diluted with EtOAc. The mixture was filtered over a pad of Celite®. The filtrate was decanted and the organic phase was washed with brine, dried over $MgSO_4$, filtered and concentrated to dryness. The crude mixture was purified by flash chromatography (irregular SiOH, 15-40 μm, 40 g GraceResolv™, liquid injection (DCM), mobile phase gradient: heptane/EtOAc from 90:10 to 60:40) to afford intermediate E1 (659 mg, 74%) as a yellow solid.

Synthesis of Final Compounds

Compound 21

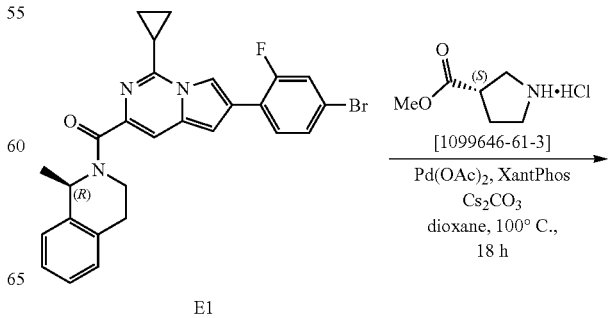

-continued

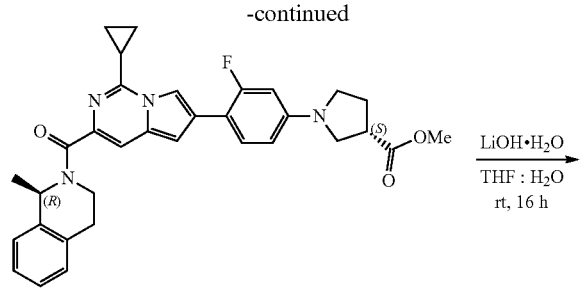

E2

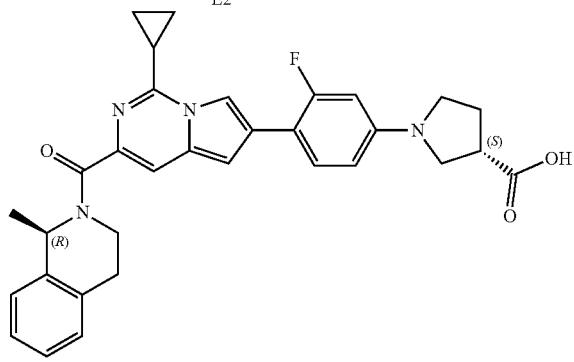

21

Intermediate E2

Methyl (3S)-1-(4-{7-cyclopropyl-5-[(1R)-1-methyl-1,2,3,4-tetrahydroisoquinoline-2-carbonyl]pyrazolo[1,5-c]pyrimidin-2-yl}-3-fluorophenyl)pyrrolidine-3-carboxylate

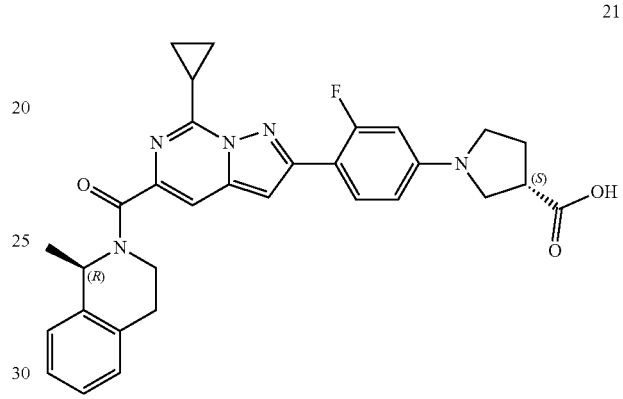

In a screw cap vial a mixture of intermediate E1 (659 mg, 1.30 mmol), (S)-methyl pyrrolidine-3-carboxylate hydrochloride [1099646-61-3] (316 mg, 1.56 mmol) and cesium carbonate (1.27 g, 3.91 mmol) in 1,4-dioxane (13.5 mL) was purged with nitrogen. XantPhos (75 mg; 130 μmol) and palladium acetate (29.3 mg, 130 μmol) were added and the reaction mixture was purged again with nitrogen. The reaction mixture was stirred at 100° C. for 18 h. The reaction mixture was filtered over a pad of Celite® and washed with EtOAc and H₂O. The filtrate was decanted and the organic phase was washed with H₂O (twice), dried over MgSO₄, filtered and concentrated to dryness. The crude mixture was purified by flash chromatography (irregular SiOH, 15-40 μm, 25 g GraceResolv™, liquid injection (DCM), mobile phase gradient: heptane/EtOAc from 90:10 to 60:40) to afford intermediate E2 (622 mg, 86%) as a yellow solid.

Compound 21

(3S)-1-(4-{7-Cyclopropyl-5-[(1R)-1-methyl-1,2,3,4-tetrahydroisoquinoline-2-carbonyl]pyrazolo[1,5-c]pyrimidin-2-yl}-3-fluorophenyl)pyrrolidine-3-carboxylic Acid

21

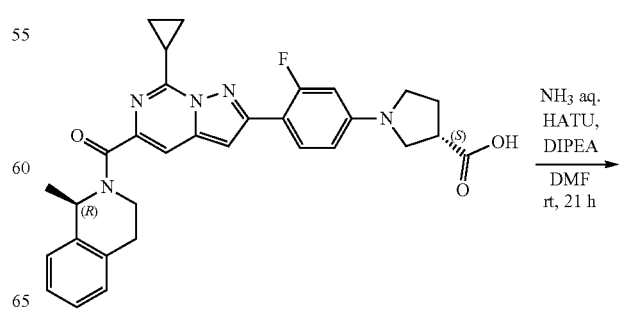

Lithium hydroxide monohydrate (10.9 mg, 0.26 mmol) was added to a solution of intermediate E2 (72.0 mg, 0.13 mmol) in THF (1 mL) and H₂O (0.5 mL). The reaction mixture was stirred at rt for 16 h. A 10% aqueous solution of KHSO₄ was added until pH 6 and the aqueous phase was extracted with EtOAc. The combined organic extracts were washed with H₂O, dried over MgSO₄, filtered and concentrated in vacuo. The residue was dried under high vacuum at 60° C. for 2 h to give compound 20 (53 mg, 76%) as a beige solid.

Compound 22

(3S)-1-(4-{7-Cyclopropyl-5-[(1R)-1-methyl-1,2,3,4-tetrahydroisoquinoline-2-carbonyl]pyrazolo[1,5-c]pyrimidin-2-yl}-3-fluorophenyl)pyrrolidine-3-carboxamide

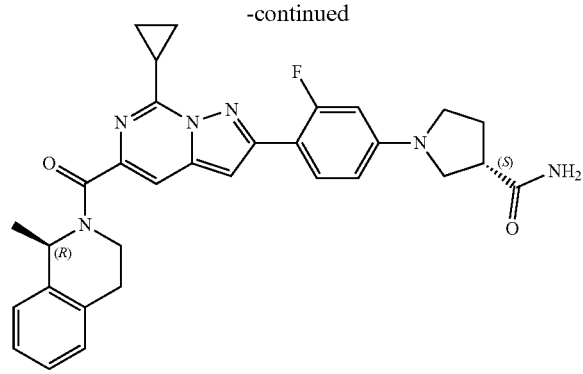

22

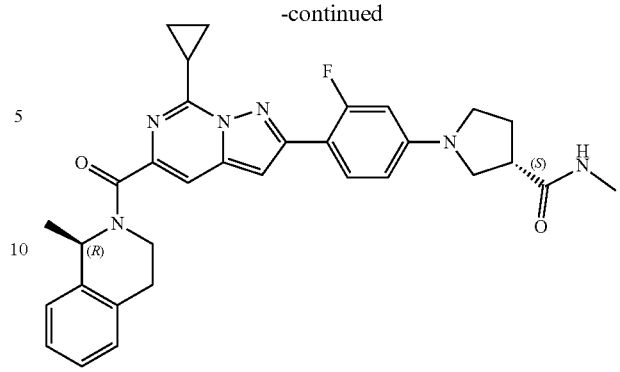

23

HATU (146 mg, 384 µmol) was added to a mixture of compound 21 (150 mg, 256 µmol, 92% purity) and DIPEA (132 µL, 767 µmol) in DMF (1.4 mL). The reaction mixture was stirred at rt for 10 min and ammonia (0.5 M in 1,4-dioxane, 7.6 mL, 3.84 mmol) was added. The reaction mixture was stirred at rt for 16 h. An additional amount of ammonia (0.5 M in 1,4-dioxane, 2.6 mL, 1.28 mmol) was added and the reaction mixture was stirred at rt for another 5 h. The reaction mixture was diluted with H₂O, brine and EtOAc. The layers were separated and the organic phase was washed with 1 M aqueous solution of NaOH (twice) and brine (3 times), dried over MgSO₄, filtered and concentrated in vacuo. The residue was diluted with a solution of DCM and MeOH (8:2) and the solid was filtered off to give a first fraction (16 mg). The filtrate was concentrated in vacuo and purified by flash chromatography (irregular SiOH, 15-40 µm, 12 g GraceResolv™, dry loading (SiOH), mobile phase gradient: DCM/MeOH from 98:2 to 80:20) to give a second fraction (20 mg). The aqueous layer was acidified with a 3M aqueous solution of HCl until pH 1 and then extracted with DCM (twice), dried over MgSO₄, filtered and concentrated in vacuo to give a third fraction (40 mg). All the fractions were combined and purified by flash chromatography (irregular SiOH, 15-40 µm, 12 g GraceResolv™, dry loading (SiOH), mobile phase gradient: DCM/MeOH from 98:2 to 80:20). The residue (34 mg) was dried under high vacuum at 60° C. for 16 h to give compound 22 (30 mg, 22%) as a beige solid.

Compound 23

(3S)-1-(4-{7-Cyclopropyl-5-[(1R)-1-methyl-1,2,3,4-tetrahydroisoquinoline-2-carbonyl]pyrazolo[1,5-c]pyrimidin-2-yl}-3-fluorophenyl)-N-methylpyrrolidine-3-carboxamide

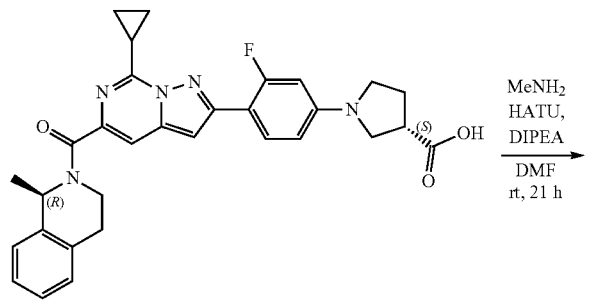

21

HATU (146 mg, 384 µmol) was added to a mixture of compound 21 (150 mg, 256 µmol, 92% purity) and DIPEA (154 µL, 895 µmol) in DMF (1.4 mL). The reaction mixture was stirred at rt for 10 min and methylamine (2.0 M in THF, 448 µL, 895 µmol) was added. The reaction mixture was stirred at rt for 16 h. Additional amount of methylamine (2.0 M in THF, 448 µL, 895 µmol) was added and the reaction mixture was stirred at rt for another 5 h. The reaction mixture was diluted with H₂O, brine and EtOAc. The layers were separated and the organic phase was washed with brine (3 times), dried over MgSO₄, filtered and concentrated in vacuo. The crude mixture was purified by flash chromatography (irregular SiOH, 15-40 µm, 12 g GraceResolv™, dry loading (SiOH), mobile phase gradient: heptane/EtOAc from 70:30 to 0:100). The residue was co-evaporated with MeCN then with EtOAc and dried under high vacuum at 60° C. for 16 h to give compound 23 (72 mg, 51%) as a yellow solid.

Imidazo[1,2-a]pyrimidines

Synthesis of Intermediates

Synthesis of Intermediate I2

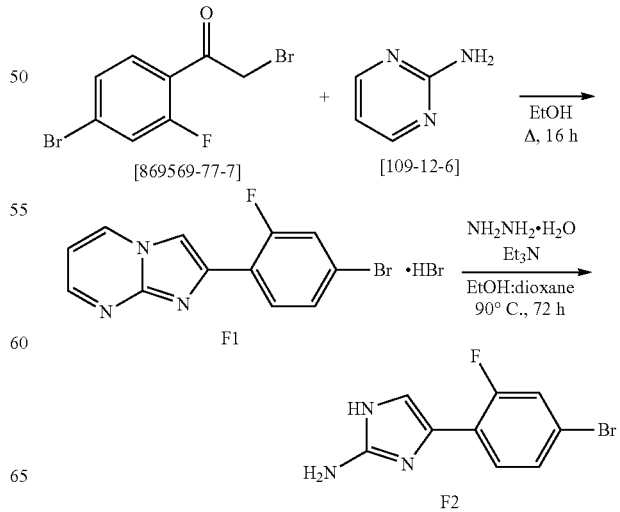

Intermediate F1

2-(4-Bromo-2-fluorophenyl)imidazo[1,2-a]pyrimidine Hydrobromide

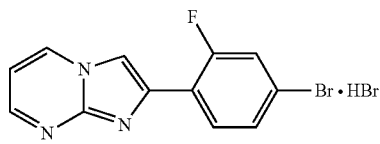

A mixture of 1-(4-bromo-2-fluorophenyl)-2-bromo-1-ethanone [869569-77-7] (5.00 g, 16.9 mmol) and 2-aminopyridine [109-12-6] (1.61 g, 16.9 mmol) in EtOH (300 mL) was stirred under reflux for 16 h. The reaction mixture was cooled to rt and the resulting precipitate was filtered off to afford a first crop of intermediate F1 (1.2 g, 19%). The filtrate was partially evaporated in vacuo and the precipitate was filtered off to afford a second crop of intermediate F1 (1.4 g, 22%).

Intermediate F2

4-(4-Bromo-2-fluorophenyl)-1H-imidazol-2-amine

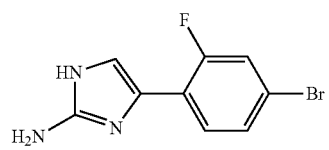

A mixture of intermediate F1 (2.25 g, 6.03 mmol), Et₃N (1.26 mL, 9.05 mmol) and hydrazine monohydrate (2.34 mL, 48.3 mmol) in EtOH (70 mL) and 1,4-dioxane (45 mL) was stirred at 90° C. for 72 h. The reaction mixture was concentrated to dryness. The residue was diluted with H₂O and EtOAc. The layers were separated and the aqueous phase was extracted with EtOAc (once). The combined organic extracts were washed with brine, dried over MgSO₄, filtered and the solvent was concentrated in vacuo. The residue (1.54 g) was taken up in DCM. The precipitate was filtered off and dried to afford intermediate F2 (1.01 g, 65%).

Synthesis of Intermediate I24

Methyl 4-cyclopropyl-2-hydroxy-4-oxobut-2-enoate

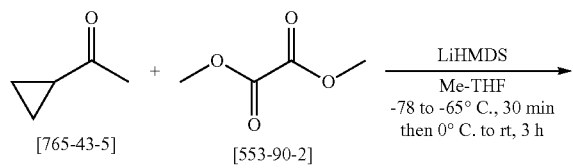

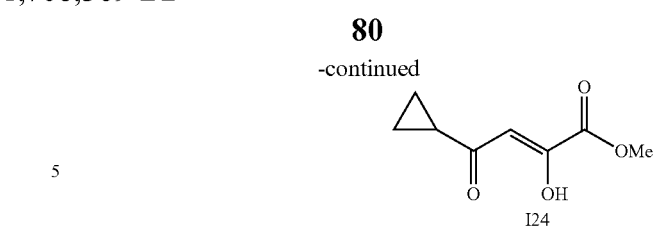

In a 6 L non-jacketed reactor equipped with mechanical stirring and under a nitrogen atmosphere, cyclopropyl methyl ketone [765-43-5] (255 mL, 2.73 mol) was added over 30 min to a mixture of lithium bis(trimethylsilyl)amide (500 g, 2.99 mol) in 2-methyltetrahydrofuran (3.5 L) at −78° C. [The temperature was maintained below −65° C. during the addition.] The reaction mixture was stirred at −70° C. for 30 min and added to a solution of dimethyl oxalate [553-90-2] (321 g, 2.72 mol) in 2-methyltetrahydrofuran (2.5 L) at 0° C. in a 10 L non-jacketed reactor equipped with mechanical stirring and under a nitrogen atmosphere. The resulting reaction mixture was stirred for 3 h and warmed to rt slowly. The reaction mixture was quenched by the addition of a 3N aqueous solution of HCl (2 L). The layers were separated and the aqueous phase was extracted with EtOAc (twice). The combined organic extracts were dried over MgSO₄, filtered and the solvent was evaporated in vacuo. The crude mixture (620 g) was purified by preparative LC (irregular SiOH, 15-40 μm, 750 g Grace®, liquid injection (DCM), mobile phase gradient: heptane/EtOAc from 90:10 to 70:30) to afford intermediate I24 (468 g, 96%) as a colorless oil. The product crystallized on standing.

Synthesis of Intermediate F3

Methyl 2-(4-bromo-2-fluorophenyl)-5-cyclopropylimidazo[1,2-a]pyrimidine-7-carboxylate

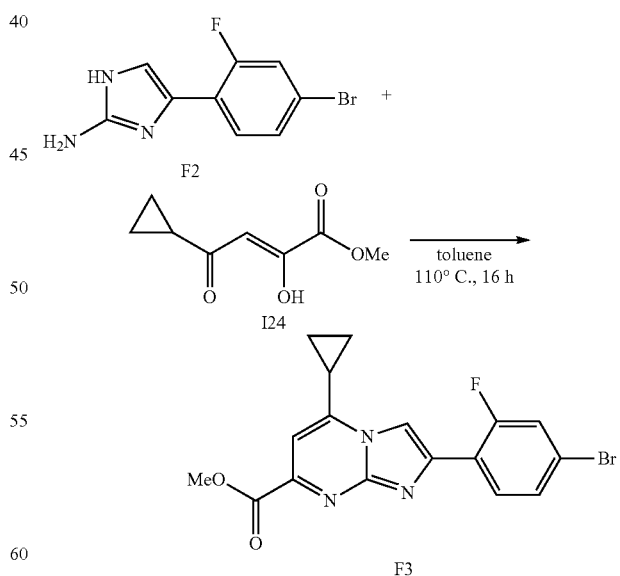

A mixture of intermediate F2 (653 mg, 2.55 mmol) and intermediate I24 (639 mg, 3.57 mmol) in toluene (29 mL) was stirred at 110° C. for 16 h. The solvent was evaporated to dryness. The residue was triturated in MeOH and the solid was filtered off to afford intermediate F3 (578 mg, 58%).

Synthesis of Intermediate F5

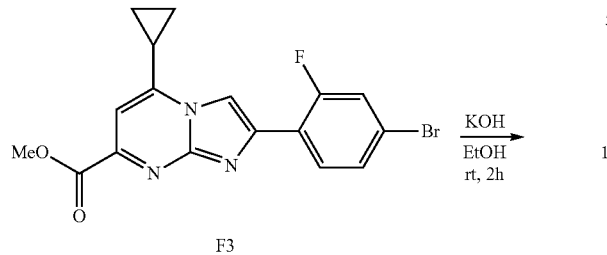

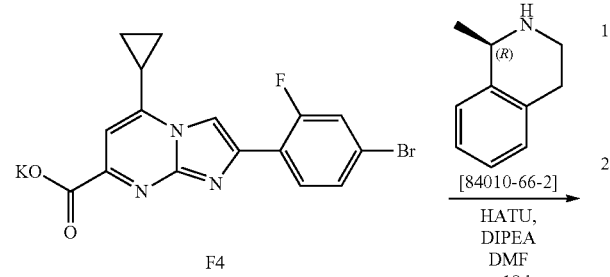

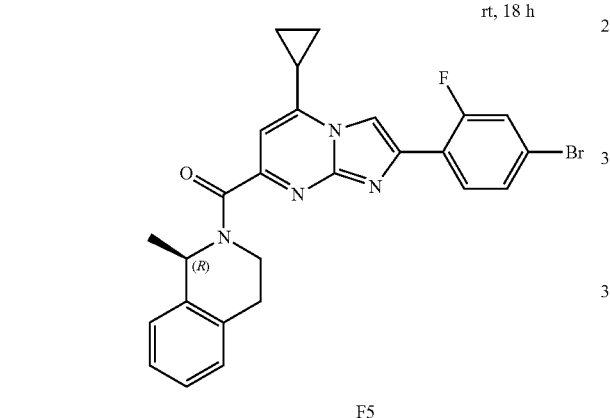

F5

Intermediate F4

Potassium 2-(4-bromo-2-fluorophenyl)-5-cyclopropylimidazo[1,2-a]pyrimidine-7-carboxylate

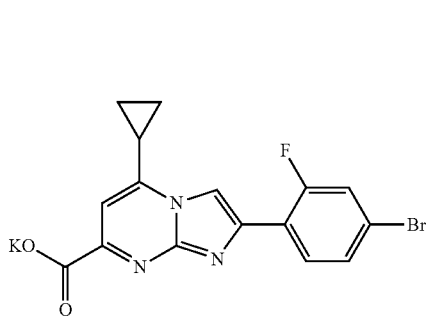

A mixture of intermediate F3 (528 mg, 1.35 mmol) and potassium hydroxide (152 mg, 2.71 mmol) in EtOH (20 mL) was stirred at rt for 2 h. The reaction mixture was combined with another fraction (50 mg, 128 µmol). The suspension was filtered off. The solid was dried and co-evaporated with toluene (twice) to afford intermediate F4 (484 mg, 79%).

Intermediate F5

(1R)-2-[2-(4-Bromo-2-fluorophenyl)-5-cyclopropylimidazo[1,2-a]pyrimidine-7-carbonyl]-1-methyl-1,2,3,4-tetrahydroisoquinoline

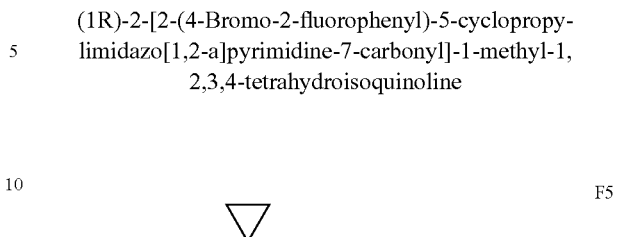

HATU (477 mg, 1.26 mmol) was added to a mixture of intermediate F4 (260 mg, 0.63 mmol), (R)-1-methyl-1,2,3,4-tetrahydroisoquinoline [84010-66-2] (111 mg, 0.75 mmol) and DIPEA (0.43 mL, 2.52 mmol) in DMF (4 mL). The reaction mixture was stirred at rt for 18 h. The reaction mixture was diluted with $H_2O$, brine and EtOAc. The layers were separated and the aqueous phase was extracted with EtOAc. The combined organic extracts were washed with brine (3 times), dried over $MgSO_4$, filtered and concentrated in vacuo. The crude mixture was purified by preparative LC (irregular SiOH, 15-40 µm, 24 g GraceResolv™, liquid injection (DCM), mobile phase gradient: heptane/EtOAc from 90:10 to 60:40) to give intermediate F5 (306 mg, 96%) as an off-white foam.

Synthesis of Intermediate F8

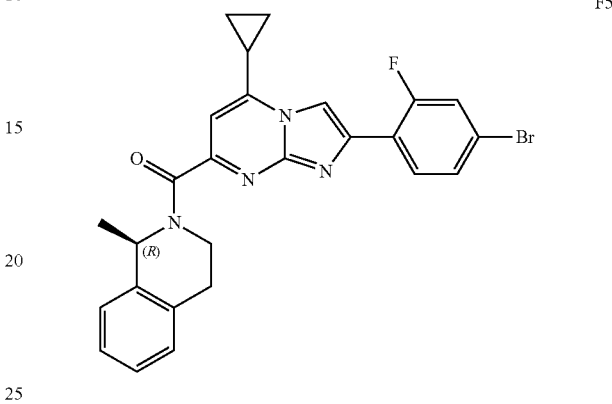

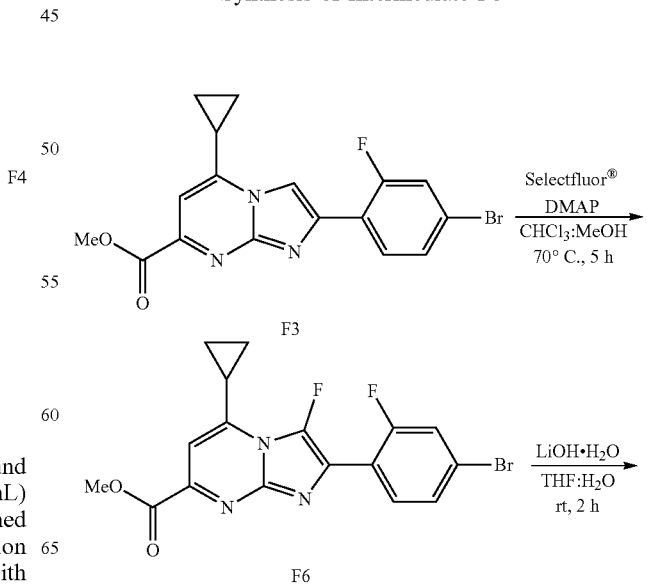

83
-continued

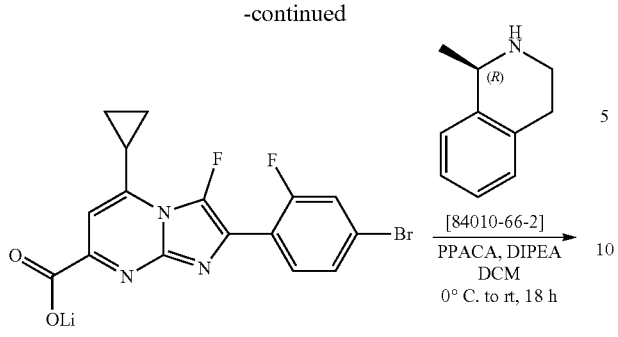

Intermediate F6

Methyl 2-(4-bromo-2-fluorophenyl)-5-cyclopropyl-3-fluoroimidazo[1,2-a]pyrimidine-7-carboxylate

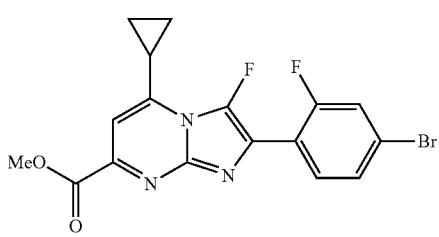

In a Schlenk tube, a mixture of intermediate F3 (242 mg, 0.62 mmol), Selectfluor® (264 mg, 744 µmol) and DMAP (83.0 mg, 0.68 mmol) in CHCl₃ (7.5 mL) and MeOH (7.5 mL) was stirred at 70° C. for 5 h. Additional amount of Selectfluor® (132 mg, 372 µmol) and DMAP (45.0 mg, 0.37 mmol) were added and the reaction mixture was stirred at 70° C. for 18 h. Extra amount of Selectfluor® (132 mg, 372 µmol) and DMAP (45.0 mg, 0.37 mmol) were added and the reaction mixture was stirred at 70° C. for another 22 h. The reaction mixture was concentrated in vacuo. The crude mixture was combined with another batch (269 mg, 0.69 mmol) and purified by preparative LC (irregular SiOH, 15-40 µm, 40 g GraceResolv™, liquid injection (DCM), mobile phase gradient: DCM/EtOAc from 90:10 to 70:30). A second purification was performed by preparative LC (irregular SiOH, 15-40 µm, 40 g GraceResolv™, liquid injection (DCM), mobile phase gradient: heptane/(EtOAc/MeOH 9:1) from 90:10 to 70:30) to afford intermediate F6 (153 mg, 29%).

84

Intermediate F7

Lithio 2-(4-bromo-2-fluorophenyl)-5-cyclopropyl-3-fluoroimidazo[1,2-a]pyrimidine-7-carboxylate

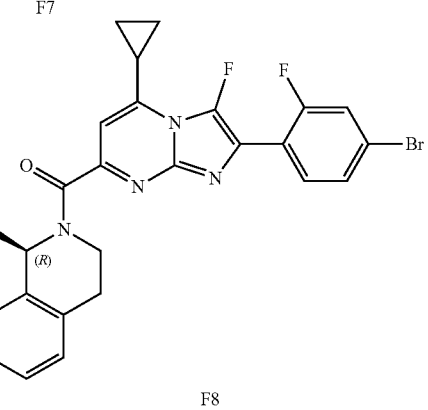

Lithium hydroxide monohydrate (47.2 mg, 1.12 mmol) was added to a solution of intermediate F6 (153 mg, 375 µmol) in THF (11 mL) and H₂O (2.5 mL). The reaction mixture was stirred at rt for 2 h. The reaction mixture was concentrated to dryness and co-evaporated with toluene (twice) to afford intermediate F7 (153 mg, quant.) as a yellowish solid.

Intermediate F8

(1R)-2-[2-(4-Bromo-2-fluorophenyl)-5-cyclopropyl-3-fluoroimidazo[1,2-a]pyrimidine-7-carbonyl]-1-methyl-1,2,3,4-tetrahydroisoquinoline

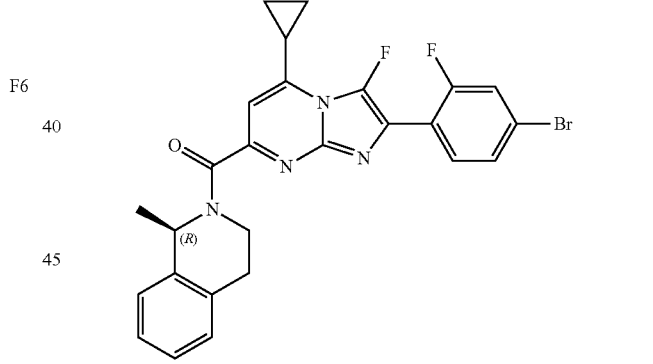

A mixture of intermediate F7 (138 mg, 0.35 mmol), (R)-1-methyl-1,2,3,4-tetrahydroisoquinoline [84010-66-2] (62.0 mg, 0.42 mmol) and DIPEA (304 µL, 1.76 mmol) in DCM (1 mL) was stirred at 0° C. PPACA (50 wt. % in EtOAc, 521 µL, 875 µmol) was added slowly. The reaction mixture was stirred at 0° C. for 10 min and at rt for 18 h. Additional amount of (R)-1-methyl-1,2,3,4-tetrahydroisoquinoline (26.0 mg, 0.18 mmol) and PPACA (50 wt. % in EtOAc, 208 µL, 350 µmol) were added at 0° C. and the reaction mixture was stirred at rt for another 22 h. The reaction mixture was diluted with H₂O. The layers were separated and the organic phase was extracted. The combined organic extracts were dried over MgSO₄, filtered and concentrated in vacuo. The crude mixture was purified by preparative LC (irregular SiOH, 15-40 µm, 12 g GraceResolv™, liquid injection (DCM), mobile phase gradient: heptane/EtOAc from 90:10 to 60:40) to afford intermediate F8 (80 mg, 44%) as a yellowish gum.

Synthesis of Final Compounds
Compound 24
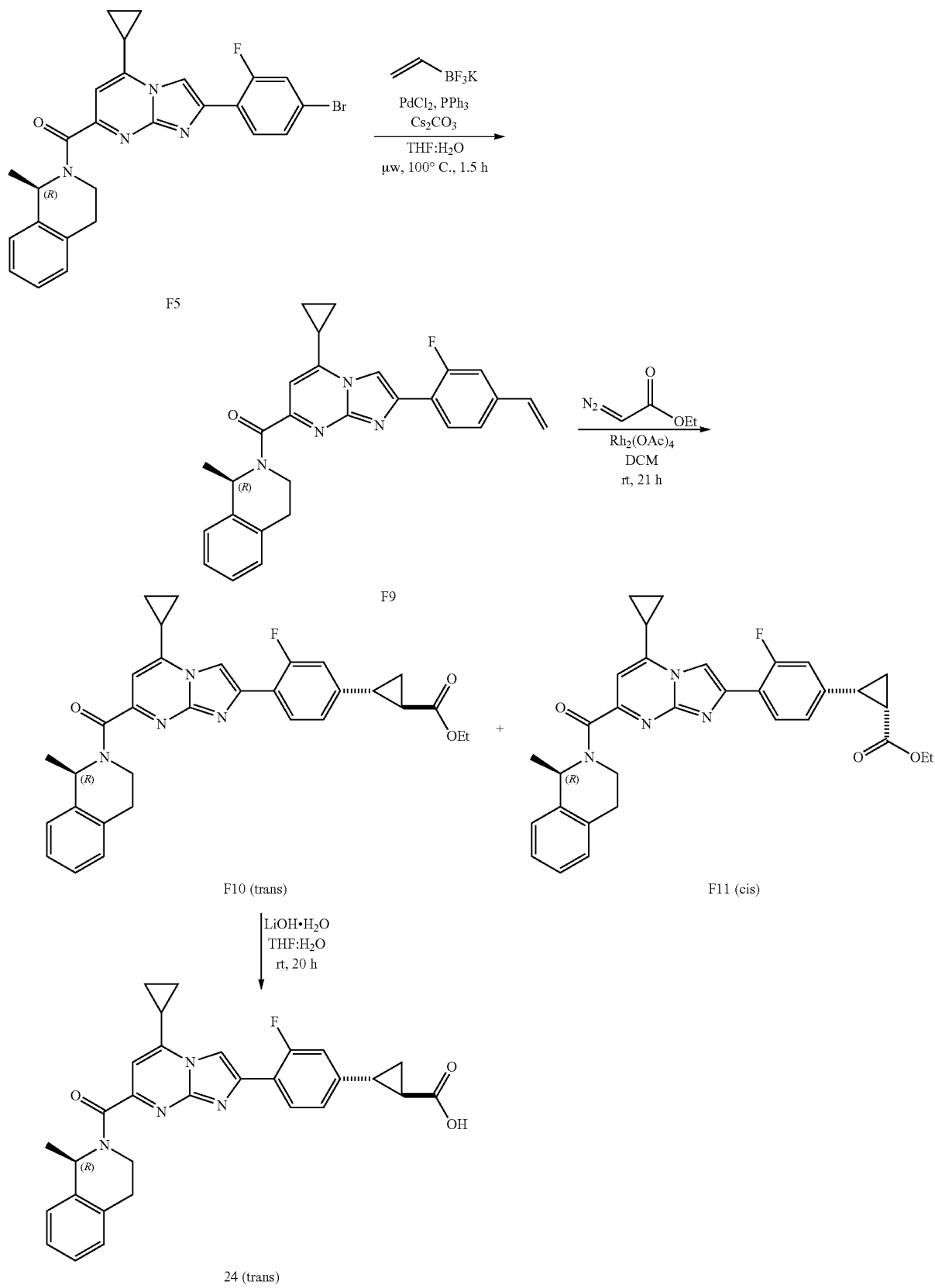

Intermediate F9

(1R)-2-[5-Cyclopropyl-2-(4-ethenyl-2-fluorophenyl)imidazo[1,2-a]pyrimidine-7-carbonyl]-1-methyl-1,2,3,4-tetrahydroisoquinoline

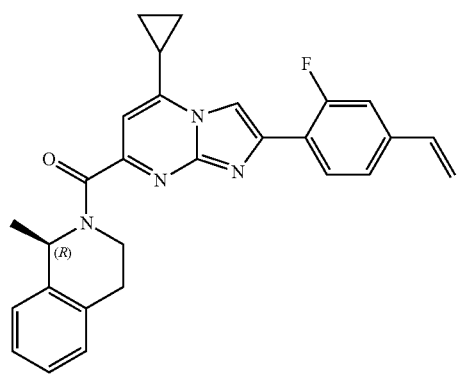

F9

Palladium(II) chloride (5.00 mg, 28.8 µmol) was added to a degassed mixture of intermediate F5 (324 mg, 641 µmol), potassium vinyltrifluoroborate (258 mg, 1.92 mmol), cesium carbonate (909 mg, 2.79 mmol) and triphenylphosphine (22.0 mg, 83.8 µmol) in THF and H₂O (9:1, 10 mL). The reaction mixture was heated at 100° C. using a single mode microwave (Biotage® Initiator EXP 60) with a power output ranging from 0 to 400 W for 1.5 h. Additional amount of palladium(II) chloride (5.00 mg, 28.8 µmol) and triphenylphosphine (22.0 mg, 83.8 µmol) were added and the reaction mixture was heated at 100° C. using a single mode microwave (Biotage® Initiator EXP 60) with a power output ranging from 0 to 400 W for 1.5 h. The reaction mixture was diluted with EtOAc and H₂O. The layers were separated and the organic phase was washed with H₂O, dried over MgSO₄, filtered and concentrated in vacuo. The crude mixture was purified by preparative LC (regular SiOH, 30 µm, 12 g Interchim®, liquid injection (DCM), mobile phase gradient: heptane/EtOAc from 90:10 to 60:40) to afford intermediate F9 (207 mg, 71%) as an off-white solid.

Intermediate F10 and F11

F10: Ethyl trans-2-(4-{5-cyclopropyl-7-[(1R)-1-methyl-1,2,3,4-tetrahydroisoquinoline-2-carbonyl]imidazo[1,2-a]pyrimidin-2-yl}-3-fluorophenyl)cyclopropane-1-carboxylate F11: Ethyl cis-2-(4-{5-cyclopropyl-7-[(1R)-1-methyl-1,2,3,4-tetrahydroisoquinoline-2-carbonyl]imidazo[1,2-a]pyrimidin-2-yl}-3-fluorophenyl)cyclopropane-1-carboxylate

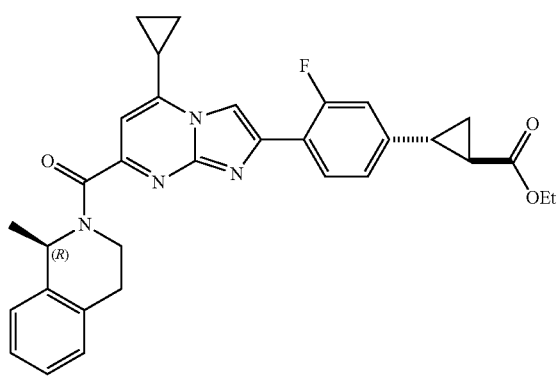

F10 (trans)

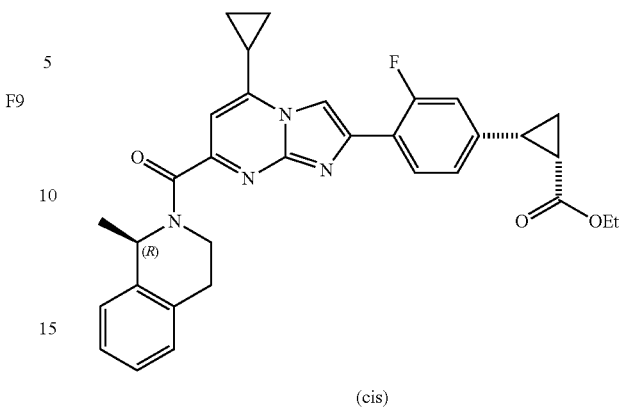

F11 (cis)

Under a nitrogen atmosphere a solution of ethyl diazoacetate [623-73-4] (150 µL, 1.21 mmol) in DCM (4 mL) was added with a syringe pump over 40 min to a mixture of intermediate F9 (182 mg, 402 µmol) and rhodium acetate dimer (9.00 mg, 40.7 µmol) in DCM (9 mL). The reaction mixture was stirred at rt for 3 h. An additional amount of ethyl diazoacetate (150 µL, 1.21 mmol) in DCM (4 mL) was added with a syringe pump over 40 min and the reaction mixture was stirred at rt for 18 h. The reaction mixture was concentrated in vacuo. The crude mixture was purified by preparative LC (irregular SiOH, 15-40 µm, 24 g GraceResolv™, liquid injection (DCM), mobile phase gradient: heptane/EtOAc from 90:10 to 70:30) to give 3 fractions as a mixture of diastereoisomers (76 mg). The fractions were purified again by preparative LC (irregular SiOH, 15-40 µm, 40 g GraceResolv™, liquid injection (DCM), mobile phase gradient: heptane/EtOAc from 100:0 to 70:30) to afford intermediate F10 (25 mg, 12%), intermediate F1 (11 mg, 5%) and a mixture of intermediates F10 and F11 (7 mg, 3%).

Compound 24 trans-2-(4-{5-Cyclopropyl-7-[(1R)-1-methyl-1,2,3,4-tetrahydroisoquinoline-2-carbonyl]imidazo[1,2-a]pyrimidin-2-yl}-3-fluorophenyl)cyclopropane-1-carboxylic Acid

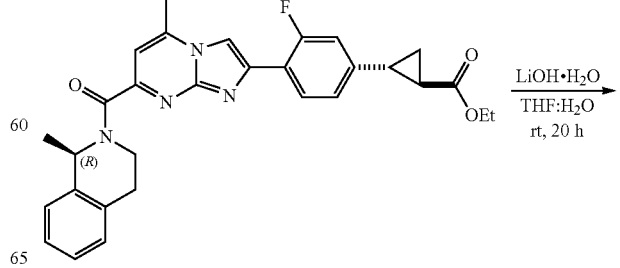

-continued

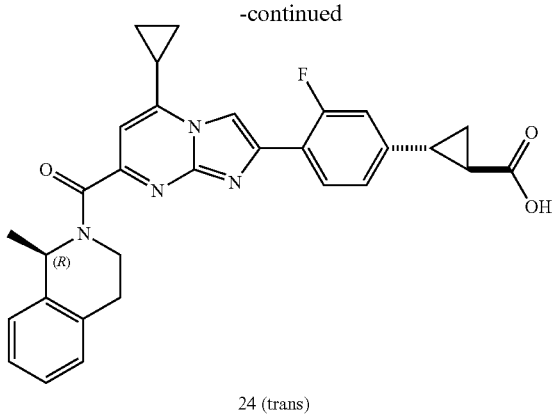

24 (trans)

Lithium hydroxide monohydrate (5.87 mg, 0.14 mmol) was added to a solution of intermediate F10 (25.0 mg, 46.4 μmol) in THF (0.8 mL) and H$_2$O (0.4 mL). The reaction mixture was stirred at rt for 20 h. The reaction mixture was diluted with brine and a 10% aqueous solution of KHSO$_4$ and DCM were added. The layers were separated and the aqueous phase was extracted with DCM (twice). The combined organic extracts were washed with a solution of water and brine (1:1), dried over MgSO$_4$, filtered and evaporated in vacuo. The crude mixture was purified by preparative LC (irregular SiOH, 15-40 μm, 4 g GraceResolv™, liquid injection (DCM), mobile phase gradient: DCM/MeOH from 100:0 to 96:4). The residue (19 mg) was purified by reverse phase (spherical C18, 25 μm, 40 g YMC-ODS-25, dry loading (Celite®), mobile phase gradient: 0.2% aq·NH$_4$HCO$_3$/MeCN from 85:15 to 45:55). The fractions containing the product were combined and a 1N aqueous solution of HCl was added until pH 1. The aqueous layer was extracted with DCM (3 times). The combined organic extracts were dried over MgSO$_4$, filtered and concentrated in vacuo. The solid (14 mg) was purified by achiral SFC (Stationary phase: CHIRALPAK AS-H 5 μm, 250*20 mm, mobile phase: 70% CO$_2$, 30% MeOH). The residue was solubilized in MeOH (2 mL), extended with water (10 mL) and freeze-dried to give compound 24 (7 mg, 30%) as a white fluffy solid.

Compounds 25 and 26

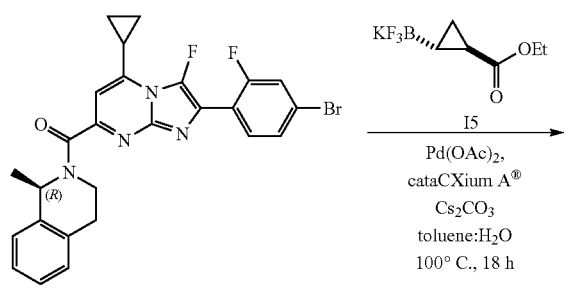

F8

-continued

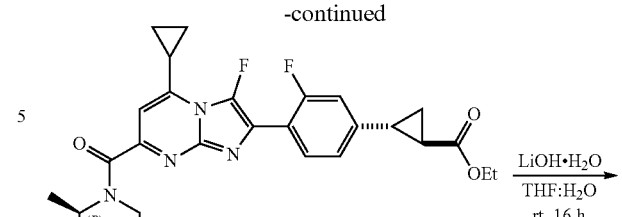

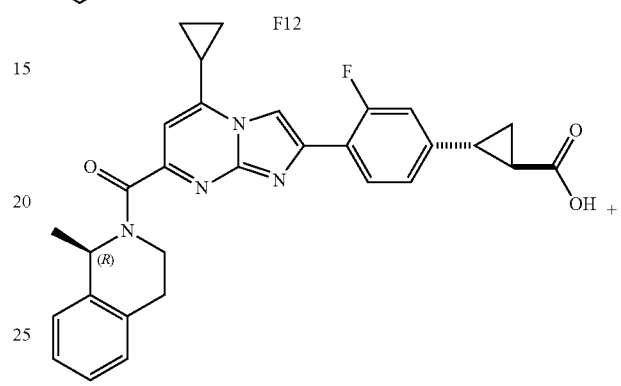

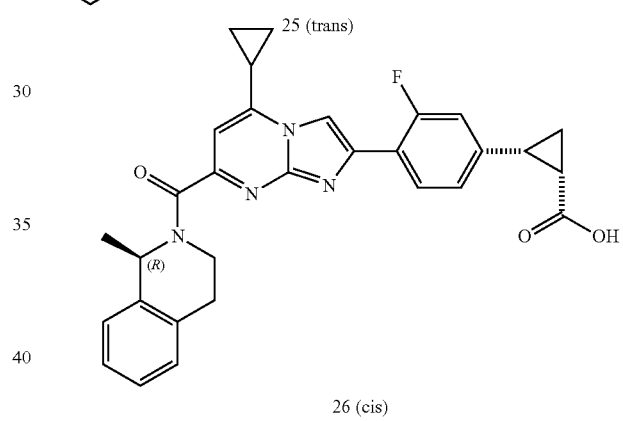

Intermediate F12

Ethyl trans-2-(4-{5-cyclopropyl-3-fluoro-7-[(1R)-1-methyl-1,2,3,4-tetrahydroisoquinoline-2-carbonyl]imidazo[1,2-a]pyrimidin-2-yl}-3-fluorophenyl)cyclopropane-1-carboxylate

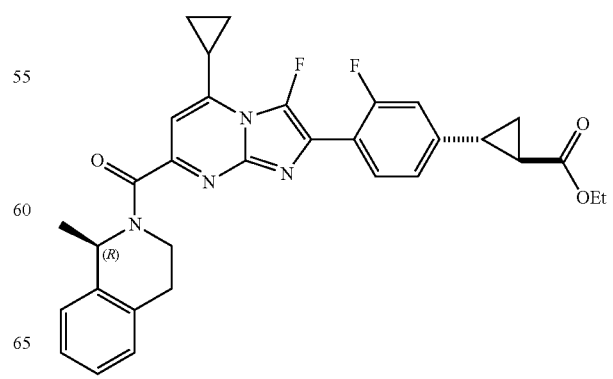

F12

To a mixture of intermediate F8 (70.0 mg, 134 µmol), intermediate I5 (cis:trans 12:88, 32.4 mg, 147 µmol) and cesium carbonate (121 mg, 372 µmol) in toluene (1.5 mL) and H$_2$O (150 µL) under a nitrogen atmosphere were added cataCxium A® (11.1 mg, 31.0 µmol) and palladium acetate (5.06 mg, 22.5 µmol). The reaction mixture was purged with nitrogen and stirred at 100° C. for 18 h. The reaction mixture was diluted with EtOAc and H$_2$O. The layers were separated and the aqueous phase was extracted with EtOAc. The combined organic extracts were washed with brine, dried over MgSO$_4$, filtered and concentrated in vacuo. The crude mixture was purified by preparative LC (irregular SiOH, 15-40 µm, 12 g GraceResolv™, liquid injection (DCM), mobile phase gradient: heptane/EtOAc from 100:0 to 70:30) to afford intermediate F12 (cis:trans 85:15, 56 mg, 75%) as a colorless gum.

Compounds 25 and 26

25: trans-2-(4-{5-cyclopropyl-3-fluoro-7-[(1R)-1-methyl-1,2,3,4-tetrahydroisoquinoline-2-carbonyl]imidazo[1,2-a]pyrimidin-2-yl}-3-fluorophenyl)cyclopropane-1-carboxylic Acid 26: cis-2-(4-{5-cyclopropyl-3-fluoro-7-[(1R)-1-methyl-1,2,3,4-tetrahydroisoquinoline-2-carbonyl]imidazo[1,2-a]pyrimidin-2-yl}-3-fluorophenyl)cyclopropane-1-carboxylic Acid

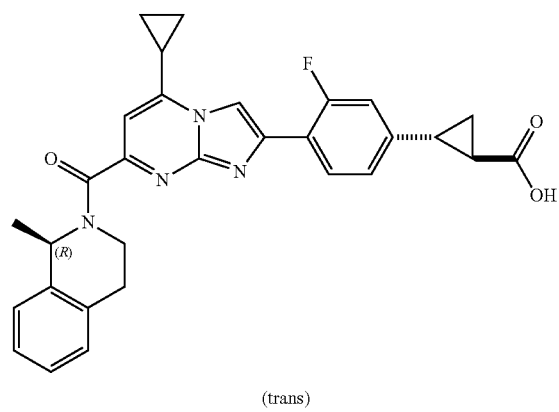

Lithium hydroxide monohydrate (12.7 mg, 302 µmol) was added to a solution of intermediate F12 (cis:trans 85:15, 56.0 mg, 101 µmol) in THF (1.8 mL) and H$_2$O (0.3 mL). The reaction mixture was stirred at rt for 16 h. The reaction mixture was diluted with brine and a 10% aqueous solution of KHSO$_4$ was added. The aqueous phase was extracted with EtOAc (twice). The combined organic extracts were washed with H$_2$O, dried over MgSO$_4$, filtered and concentrated in vacuo. The crude mixture was purified by achiral SFC (Stationary phase: DIETHYLAMINOPROPYL 5 µm 150× 30 mm, Mobile phase: 50% CO$_2$, 50% MeOH) to give 2 fractions: A and B. Fraction A (15 mg) was solubilized in MeCN (2 mL), extended with water (10 mL) and freeze-dried to give compound 25 (15 mg, 28%) as a yellowish fluffy solid. Fraction B (18 mg) was solubilized in MeCN (2 mL), extended with water (10 mL) and freeze-dried to give compound 26 (18 mg, 34%) as a yellowish fluffy solid.

Compound 27

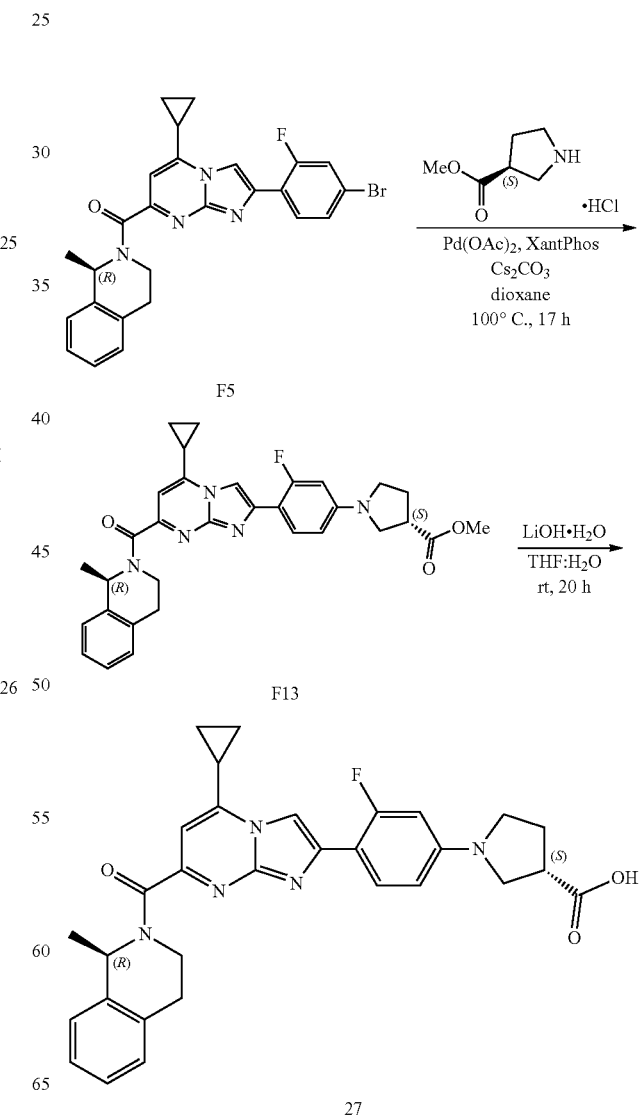

Intermediate F13

Methyl (3S)-1-(4-{5-cyclopropyl-7-[(1R)-1-methyl-1,2,3,4-tetrahydroisoquinoline-2-carbonyl]imidazo[1,2-a]pyrimidin-2-yl}-3-fluorophenyl)pyrrolidine-3-carboxylate

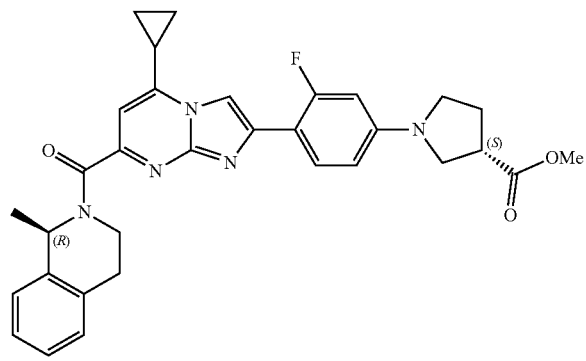

F13

A sealed tube was charged with intermediate F5 (251 mg, 497 μmol), (S)-methyl pyrrolidine-3-carboxylate hydrochloride [1099646-61-3] (98.7 mg, 596 μmol), cesium carbonate (485 mg, 1.49 mmol) and XantPhos (28.7 mg, 49.7 μmol) and purged with nitrogen. 1,4-Dioxane (7.5 mL) was added and the mixture was purged again with nitrogen. Palladium acetate (11.2 mg, 49.7 μmol) was added. The reaction mixture was purged with nitrogen and stirred at 100° C. for 17 h. The reaction mixture was diluted with EtOAc and H₂O. The layers were separated and the aqueous phase was extracted with EtOAc (twice). The combined organic extracts were washed with brine, dried over MgSO₄, filtered and the solvent was evaporated in vacuo. The crude mixture was purified by preparative LC (irregular SiOH, 15-40 μm, 12 g Grace®, liquid injection (DCM), mobile phase gradient: heptane/EtOAc from 90:10 to 50:50) to afford intermediate F13 (187 mg, 68%) as a yellow foam.

Compound 27

(3S)-1-(4-{5-Cyclopropyl-7-[(1R)-1-methyl-1,2,3,4-tetrahydroisoquinoline-2-carbonyl]imidazo[1,2-a]pyrimidin-2-yl}-3-fluorophenyl)pyrrolidine-3-carboxylic Acid

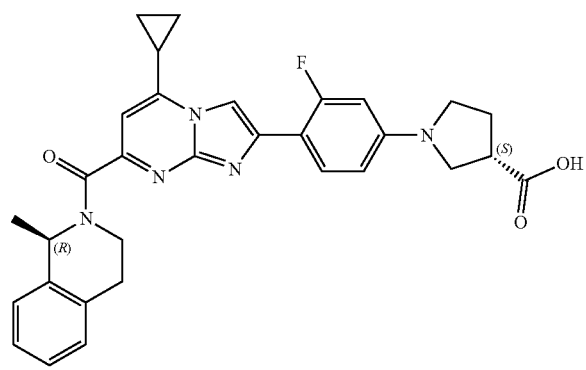

27

Lithium hydroxide monohydrate (40.0 mg, 953 μmol) was added to a solution of intermediate F13 (175 mg, 316 μmol) in THF (4.2 mL) and H₂O (1.8 mL). The reaction mixture was stirred at rt for 20 h. The reaction mixture was diluted with brine and a 10% aqueous solution of KHSO₄ and DCM were added. The layers were separated and the aqueous phase was extracted with DCM (twice). The combined organic extracts were washed with a solution of H₂O and brine (1:1), dried over MgSO₄, filtered and concentrated in vacuo. The crude mixture was triturated in MeOH. The solid was filtered off and dried under high vacuum at 50° C. for 3 h to give compound 27 (146 mg, 86%) as a yellow solid.

Compound 28

(3S)-1-(4-{5-Cyclopropyl-7-[(1R)-1-methyl-1,2,3,4-tetrahydroisoquinoline-2-carbonyl]imidazo[1,2-a]pyrimidin-2-yl}-3-fluorophenyl)pyrrolidine-3-carboxamide

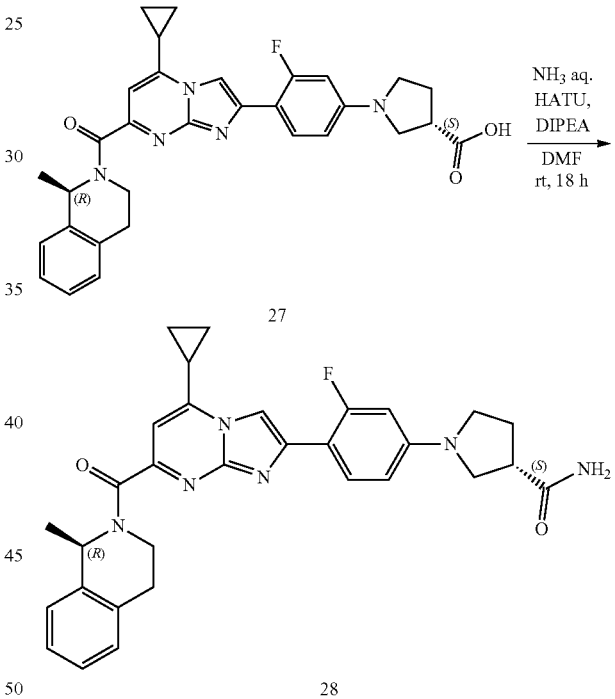

A mixture of compound 27 (107 mg, 198 μmol), HATU (113 mg, 297 μmol) and DIPEA (107 μL, 0.62 mmol) in DMF (5.4 mL) was stirred at rt for 1 h. Ammonia (28% in H₂O, 68 μL, 1.00 mmol) was added and the reaction mixture was stirred at rt for 18 h. The reaction mixture was diluted with H₂O and EtOAc. The layers were separated and the aqueous phase was extracted with EtOAc (twice). The combined organic extracts were washed with brine (3 times), dried over MgSO₄, filtered and concentrated in vacuo. The crude mixture was purified by preparative LC (irregular SiOH, 15-40 μm, 12 g GraceResolv™, liquid injection (DCM), mobile phase gradient: DCM/MeOH from 100:0 to 96:4). The residue was triturated in MeOH. The solid was filtered off and dried under high vacuum at 50° C. for 20 h to give compound 28 (71 mg, 66%) as a yellow solid.

C. Compound Identification

¹H-NMR

¹H-NMR spectra were recorded on a Bruker Avance DRX 400 spectrometer using internal deuterium lock and equipped with reverse double-resonance (¹H, ¹³C, SEI) probe head with z gradients and operating at 400 MHz for proton and 100 MHz for carbon and a Bruker Avance 500 MHz spectrometer equipped with a Bruker 5 mm BBFO probe head with z gradients and operating at 500 MHz for proton and 125 MHz for carbon.

NMR spectra were recorded at ambient temperature unless otherwise stated.

Data are reported as follow: chemical shift in parts per million (ppm) relative to TMS (δ=0 ppm) which was used as internal standard, integration, multiplicity (s=singulet, d=doublet, t=triplet, q=quartet, quin=quintuplet, sex=sextuplet, m=multiplet, b=broad, or a combination of these), coupling constant(s) J in Hertz (Hz).

Compound 1
Major Rotamer (80%)
¹H NMR (500 MHz, DMSO-$d_6$) δ ppm 12.37 (br s, 1H), 7.93 (s, 1H), 7.80 (t, J=8.4 Hz, 1H), 7.54 (s, 1H), 7.16-7.34 (m, 4H), 7.14 (dd, J=12.8, 1.4 Hz, 1H), 7.11 (dd, J=8.2, 1.6 Hz, 1H), 7.05 (s, 1H), 6.51 (br s, 1H), 5.47-5.61 (m, 1H), 3.83-3.98 (m, 1H), 3.38-3.59 (m, 1H), 2.98-3.10 (m, 1H), 2.95 (q, J=7.3 Hz, 2H), 2.78 (br d, J=15.8 Hz, 1H), 2.43-2.48 (m, 1H), 1.87-1.93 (m, 1H), 1.52 (br d, J=6.6 Hz, 3H), 1.40-1.49 (m, 2H), 1.37 (br t, J=6.9 Hz, 3H).

Minor Rotamer (20%)
¹H NMR (500 MHz, DMSO-$d_6$) δ ppm 12.37 (br s, 1H), 7.93 (s, 1H), 7.80 (t, J=8.4 Hz, 1H), 7.54 (s, 1H), 7.16-7.34 (m, 4H), 7.14 (dd, J=12.8, 1.4 Hz, 1H), 7.11 (dd, J=8.2, 1.6 Hz, 1H), 7.05 (s, 1H), 6.51 (br s, 1H), 4.94-5.11 (m, 1H), 4.39-4.60 (m, 1H), 3.38-3.59 (m, 1H), 2.98-3.10 (m, 1H), 2.95 (q, J=7.3 Hz, 2H), 2.78 (br d, J=15.8 Hz, 1H), 2.43-2.48 (m, 1H), 1.87-1.93 (m, 1H), 1.52 (br d, J=6.6 Hz, 3H), 1.40-1.49 (m, 2H), 1.37 (br t, J=6.9 Hz, 3H).

Compound 2
¹H NMR (500 MHz, DMSO-$d_6$) δ ppm 7.86 (s, 1H), 7.75 (t, J=8.4 Hz, 1H), 7.48 (s, 1H), 7.27-7.40 (br s, 1H), 7.13-7.23 (m, 4H), 6.98-7.07 (m, 3H), 6.54-6.85 (br s, 1H), 6.48 (s, 1H), 5.37 (br s, 1H), 4.10 (br s, 1H), 3.41 (br t, J=11.2 Hz, 1H), 2.91-3.03 (m, 4H), 2.78 (br d, J=16.1 Hz, 1H), 2.27-2.33 (m, 1H), 1.89-1.95 (m, 1H), 1.52 (d, J=6.6 Hz, 3H), 1.37 (t, J=7.4 Hz, 3H), 1.19-1.25 (m, 1H).

Compound 3
¹H NMR (400 MHz, DMSO-$d_6$) δ ppm 12.51 (br s, 1H), 7.79 (s, 1H), 7.67 (t, J=8.8 Hz, 1H), 7.49 (s, 1H), 7.21-7.34 (m, 1H), 7.17 (br s, 3H), 6.94 (s, 1H), 6.39-6.51 (m, 3H), 5.48 (s, 1H), 3.94 (s, 1H), 3.41-3.54 (m, 3H), 3.33-3.40 (m, 2H), 3.17-3.26 (m, 1H), 2.97-3.08 (m, 1H), 2.89-2.97 (m, 2H), 2.77 (br d, J=15.2 Hz, 1H), 2.12-2.28 (m, 2H), 1.52 (br d, J=6.6 Hz, 3H), 1.36 (br t, J=7.3 Hz, 3H).

Compound 4
Major Rotamer (70%)
¹H NMR (500 MHz, DMSO-$d_6$) δ ppm 12.39 (br s, 1H), 8.07 (t, J=8.0 Hz, 1H), 7.76 (br s, 1H), 7.32 (br s, 1H), 7.06-7.26 (m, 6H), 6.86 (br s, 1H), 5.58 (br s, 1H), 3.71-3.84 (m, 1H), 3.43-3.54 (m, 1H), 3.16-3.26 (m, 2H), 2.93-3.09 (m, 1H), 2.70-2.87 (m, 1H), 1.90-1.97 (m, 1H), 1.36-1.55 (m, 8H), 1.23 (br s, 1H).

Minor Rotamer (30%)
¹H NMR (500 MHz, DMSO-$d_6$) δ ppm 12.39 (br s, 1H), 8.07 (t, J=8.0 Hz, 1H), 7.76 (br s, 1H), 7.06-7.26 (m, 7H), 6.79 (br s, 1H), 4.90 (br s, 1H), 4.55 (br s, 1H), 3.43-3.54 (m, 1H), 3.16-3.26 (m, 2H), 2.93-3.09 (m, 1H), 2.70-2.87 (m, 1H), 1.90-1.97 (m, 1H), 1.36-1.55 (m, 8H), 1.23 (br s, 1H).

Compound 5
Major Rotamer (70%)
¹H NMR (500 MHz, DMSO-$d_6$) δ ppm 12.06 (br s, 1H), 7.97 (t, J=7.9 Hz, 1H), 7.26 (br d, J=7.6 Hz, 1H), 6.96-7.20 (m, 6H), 6.55-6.70 (m, 1H), 5.58 (q, J=6.5 Hz, 1H), 3.51-4.08 (m, 4H), 3.34-3.47 (m, 1H), 2.74-3.13 (m, 4H), 2.60-2.70 (m, 1H), 1.80-1.88 (m, 1H), 1.45 (d, J=6.9 Hz, 3H), 1.27-1.42 (m, 5H).

Minor Rotamer (30%)
¹H NMR (500 MHz, DMSO-$d_6$) δ ppm 12.06 (br s, 1H), 7.96 (t, J=7.6 Hz, 1H), 6.96-7.20 (m, 7H), 6.55-6.70 (m, 1H), 4.65-4.79 (m, 1H), 4.52-4.60 (m, 1H), 3.51-4.08 (m, 3H), 3.34-3.47 (m, 1H), 2.74-3.13 (m, 4H), 2.60-2.70 (m, 1H), 1.80-1.88 (m, 1H), 1.27-1.42 (m, 8H).

Compound 6
Major Rotamer (70%)
¹H NMR (400 MHz, DMSO-$d_6$) δ ppm 12.39 (br s, 1H), 8.07 (t, J=7.8 Hz, 1H), 7.32 (d, J=7.6 Hz, 1H), 7.09-7.27 (m, 6H), 6.65 (d, J=6.1 Hz, 1H), 5.62 (q, J=6.6 Hz, 1H), 3.65 (br dd, J=13.9, 3.8 Hz, 1H), 3.44-3.56 (m, 1H), 2.82-2.98 (m, 1H), 2.68-2.78 (m, 2H), 1.89-2.00 (m, 1H), 1.52 (d, J=7.1 Hz, 3H), 1.39-1.48 (m, 2H), 1.11-1.19 (m, 2H), 0.97-1.08 (m, 2H).

Minor Rotamer (30%)
¹H NMR (400 MHz, DMSO-$d_6$) δ ppm 12.39 (br s, 1H), 8.06 (t, J=7.8 Hz, 1H), 7.09-7.27 (m, 7H), 6.65 (d, J=6.1 Hz, 1H), 4.82 (q, J=6.6 Hz, 1H), 4.59 (br d, J=13.6 Hz, 1H), 3.24-3.29 (m, 1H), 2.82-2.98 (m, 2H), 2.68-2.78 (m, 1H), 1.89-2.00 (m, 1H), 1.39-1.49 (m, 5H), 1.11-1.19 (m, 2H), 0.97-1.08 (m, 2H).

Compound 7
Major Rotamer (65%)
¹H NMR (500 MHz, DMSO-$d_6$) δ ppm 7.96 (t, J=8.8 Hz, 1H), 7.67 (br s, 1H), 7.31 (br s, 1H), 7.14-7.28 (m, 3H), 6.94 (d, J=4.1 Hz, 1H), 6.77 (br s, 1H), 6.51 (dd, J=8.8, 2.2 Hz, 1H), 6.43 (dd, J=14.7, 2.0 Hz, 1H), 5.58 (br s, 1H), 3.78 (br d, J=10.4 Hz, 1H), 3.47 (br d, J=6.9 Hz, 3H), 3.14-3.24 (m, 3H), 3.08-3.15 (m, 1H), 2.90-3.07 (m, 1H), 2.75 (br d, J=17.3 Hz, 1H), 2.11-2.24 (m, 2H), 1.52 (d, J=6.6 Hz, 3H), 1.34-1.46 (br s, 3H).

Minor Rotamer (35%)
¹H NMR (500 MHz, DMSO-$d_6$) δ ppm 7.96 (t, J=8.8 Hz, 1H), 7.67 (br s, 1H), 7.14-7.28 (m, 3H), 7.10 (br s, 1H), 6.94 (d, J=4.1 Hz, 1H), 6.70 (br s, 1H), 6.51 (dd, J=8.8, 2.2 Hz, 1H), 6.43 (dd, J=14.7, 2.0 Hz, 1H), 4.90 (br s, 1H), 4.55 (br s, 1H), 3.47 (br d, J=6.9 Hz, 3H), 3.14-3.24 (m, 2H), 3.08-3.15 (m, 1H), 2.90-3.07 (m, 2H), 2.79-2.87 (m, 1H), 2.11-2.24 (m, 2H), 1.52 (d, J=6.6 Hz, 3H), 1.34-1.46 (br s, 3H).

Compound 8
Major Rotamer (60%)
¹H NMR (500 MHz, DMSO-$d_6$) δ ppm 7.97 (t, J=8.8 Hz, 1H), 7.68 (br s, 1H), 7.51 (br s, 1H), 7.08-7.35 (m, 4H), 7.00 (br s, 1H), 6.95 (d, J=3.8 Hz, 1H), 6.78 (br s, 1H), 6.51 (dd, J=8.8, 1.9 Hz, 1H), 6.43 (dd, J=14.8, 1.6 Hz, 1H), 5.58 (br s, 1H), 3.78 (br d, J=8.5 Hz, 1H), 3.44-3.53 (m, 2H), 3.35-3.44 (m, 2H), 3.14-3.24 (m, 2H), 3.08 (br quin, J=7.6 Hz, 1H), 2.92-3.12 (m, 1H), 2.75 (br d, J=14.8 Hz, 1H), 2.15-2.25 (m, 1H), 2.05-2.14 (m, 1H), 1.52 (d, J=6.6 Hz, 3H), 1.41 (br s, 3H).

Minor Rotamer (30%)
¹H NMR (500 MHz, DMSO-$d_6$) δ ppm 7.97 (t, J=8.8 Hz, 1H), 7.68 (br s, 1H), 7.51 (br s, 1H), 7.08-7.35 (m, 4H), 7.00 (br s, 1H), 6.95 (d, J=3.8 Hz, 1H), 6.71 (br s, 1H), 6.51 (dd, J=8.8, 1.9 Hz, 1H), 6.43 (dd, J=14.8, 1.6 Hz, 1H), 4.90 (br s, 1H), 4.55 (br s, 1H), 3.44-3.53 (m, 1H), 3.35-3.44 (m, 2H), 3.27-3.31 (m, 1H), 3.14-3.24 (m, 2H), 3.08 (br quin, J=7.6 Hz, 1H), 2.92-3.12 (m, 1H), 2.79-2.88 (br s, 1H), 2.15-2.25 (m, 1H), 2.05-2.14 (m, 1H), 1.52 (d, J=6.6 Hz, 3H), 1.41 (br s, 3H).

Compound 9
Major Rotamer (65%)
$^1$H NMR (500 MHz, DMSO-$d_6$) δ ppm 7.91-8.01 (m, 1H), 7.33 (br d, J=7.6 Hz, 1H), 7.23 (br t, J=7.6 Hz, 1H), 7.07-7.21 (m, 2H), 6.84-7.00 (m, 1H), 6.32-6.74 (m, 3H), 5.63-5.72 (m, 1H), 4.63-4.72 (m, 1H), 3.44-3.55 (m, 3H), 3.32-3.38 (m, 2H), 3.13-3.22 (m, 3H), 2.85-3.01 (m, 1H), 2.66-2.78 (m, 1H), 2.37 (br s, 3H), 2.13-2.27 (m, 2H), 1.54 (br d, J=6.0 Hz, 3H), 1.32-1.45 (m, 3H).

Minor Rotamer (35%)
$^1$H NMR (500 MHz, DMSO-$d_6$) δ ppm 7.91-8.01 (m, 1H), 7.07-7.21 (m, 4H), 6.84-7.00 (m, 1H), 6.32-6.74 (m, 3H), 4.74-4.79 (m, 1H), 3.44-3.55 (m, 3H), 3.32-3.38 (m, 3H), 3.13-3.22 (m, 3H), 2.85-3.01 (m, 2H), 2.31 (br s, 3H), 2.13-2.27 (m, 2H), 1.32-1.45 (m, 6H).

Compound 10
Major Rotamer (70%)
$^1$H NMR (500 MHz, DMSO-$d_6$) δ ppm 7.98 (t, J=8.8 Hz, 1H), 7.51 (br s, 1H), 7.32 (br d, J=7.6 Hz, 1H), 7.23 (br t, J=7.1 Hz, 1H), 7.09-7.21 (m, 2H), 6.96-7.06 (m, 3H), 6.50-6.58 (m, 1H), 6.45 (br dd, J=14.8, 1.9 Hz, 1H), 5.62 (q, J=6.2 Hz, 1H), 3.65 (br d, J=14.8 Hz, 1H), 3.50 (br t, J=8.8 Hz, 2H), 3.34-3.44 (m, 3H), 3.09 (quin, J=7.5 Hz, 1H), 2.82-2.95 (m, 1H), 2.68-2.77 (m, 2H), 2.16-2.24 (m, 1H), 2.05-2.15 (m, 1H), 1.52 (d, J=6.6 Hz, 3H), 1.15 (br d, J=8.5 Hz, 2H), 0.96-1.08 (m, 2H).

Minor Rotamer (30%)
$^1$H NMR (500 MHz, DMSO-$d_6$) δ ppm 7.97 (t, J=8.8 Hz, 1H), 7.51 (br s, 1H), 7.09-7.21 (m, 4H), 6.96-7.06 (m, 3H), 6.50-6.58 (m, 1H), 6.45 (br dd, J=14.8, 1.9 Hz, 1H), 4.81 (q, J=6.6 Hz, 1H), 4.55-4.63 (m, 1H), 3.50 (br t, J=8.8 Hz, 2H), 3.34-3.44 (m, 2H), 3.24-3.30 (m, 1H), 3.09 (quin, J=7.5 Hz, 1H), 2.82-2.95 (m, 2H), 2.68-2.77 (m, 1H), 2.16-2.24 (m, 1H), 2.05-2.15 (m, 1H), 1.42 (br d, J=6.6 Hz, 3H), 1.15 (br d, J=8.5 Hz, 2H), 0.96-1.08 (m, 2H).

Compound 11
$^1$H NMR (500 MHz, DMSO-$d_6$, 77° C.) δ ppm 12.03 (br s, 1H), 8.32 (d, J=3.5 Hz, 1H), 8.17 (t, J=8.2 Hz, 1H), 7.50 (s, 1H), 7.12-7.23 (m, 6H), 6.66 (s, 1H), 5.37 (br s, 1H), 4.00 (br s, 1H), 3.42 (br s, 1H), 2.97 (ddd, J=16.7, 11.4, 6.0 Hz, 1H), 2.77 (br d, J=16.1 Hz, 1H), 2.29-2.37 (m, 1H), 1.88-1.94 (m, 1H), 1.52 (d, J=6.6 Hz, 3H), 1.48 (br dt, J=9.3, 4.8 Hz, 1H), 1.38-1.44 (m, 1H), 1.13-1.17 (m, 2H), 0.86-0.92 (m, 2H).

Compound 12
Major Rotamer (75%)
$^1$H NMR (500 MHz, DMSO-$d_6$) δ ppm 8.62 (s, 1H), 8.33 (d, J=4.1 Hz, 1H), 8.19 (t, J=8.0 Hz, 1H), 7.62 (br s, 1H), 7.30 (br s, 1H), 7.09-7.25 (m, 5H), 6.95 (br s, 1H), 6.84 (br s, 1H), 5.54 (br s, 1H), 3.82 (br s, 1H), 3.46 (br s, 1H), 3.03 (br s, 1H), 2.77 (br d, J=15.8 Hz, 1H), 2.53-2.62 (m, 1H), 2.25-2.33 (m, 1H), 1.87-1.98 (m, 1H), 1.51 (br d, J=6.6 Hz, 3H), 1.36-1.42 (m, 1H), 1.27-1.33 (m 1H), 1.04-1.17 (m. 4H).

Minor Rotamer (25%)
$^1$H NMR (500 MHz, DMSO-$d_6$) δ ppm 8.62 (s, 1H), 8.33 (d, J=4.1 Hz, 1H), 8.19 (t, J=8.0 Hz, 1H), 7.62 (br s, 1H), 7.09-7.25 (m, 6H), 6.95 (br s, 1H), 6.84 (br s, 1H), 4.95 (br s, 1H), 4.51 (br s, 1H), 3.46 (br s, 1H), 3.03 (br s, 1H), 2.77 (br d, J=15.8 Hz, 1H), 2.53-2.62 (m, 1H), 2.25-2.33 (m, 1H), 1.87-1.98 (m, 1H), 1.51 (br d, J=6.6 Hz, 3H), 1.36-1.42 (m, 1H), 1.27-1.33 (m, 1H), 1.04-1.17 (m, 4H).

Compound 13
Major Rotamer (70%)
$^1$H NMR (500 MHz, DMSO-$d_6$) δ ppm 8.17 (br d, J=2.8 Hz, 1H), 8.07 (br t, J=8.8 Hz, 1H), 7.50 (br s, 2H), 7.31 (br s, 1H), 7.04-7.25 (m, 3H), 6.99 (br s, 1H), 6.69 (br s, 1H), 6.50 (br d, J=8.5 Hz, 1H), 6.44 (d, J=14.5 Hz, 1H), 5.57 (br s, 1H), 3.74 (br s, 1H), 3.35-3.56 (m, 4H), 3.20-3.31 (m, 1H), 3.08 (quin, J=7.5 Hz, 1H), 3.00 (br s, 1H), 2.68-2.86 (m, 1H), 2.33 (br s, 1H), 2.15-2.24 (m, 1H), 2.04-2.15 (m, 1H), 1.52 (br d, J=6.6 Hz, 3H), 1.12 (br s, 2H), 0.89 (br s, 2H).

Minor Rotamer (30%)
$^1$H NMR (500 MHz, DMSO-$d_6$) δ ppm 8.17 (br d, J=2.8 Hz, 1H), 8.07 (br t, J=8.8 Hz, 1H), 7.50 (br s, 2H), 7.04-7.25 (m, 4H), 6.99 (br s, 1H), 6.62 (br s, 1H), 6.50 (br d, J=8.5 Hz, 1H), 6.44 (d, J=14.5 Hz, 1H), 4.89 (br s, 1H), 4.54 (br s, 1H), 3.35-3.56 (m, 4H), 3.20-3.31 (m, 1H), 3.08 (quin, J=7.5 Hz, 1H), 3.00 (br s, 1H), 2.68-2.86 (m, 1H), 2.33 (br s, 1H), 2.15-2.24 (m, 1H), 2.04-2.15 (m, 1H), 1.52 (br d, J=6.6 Hz, 3H), 1.12 (br s, 2H), 0.89 (br s, 2H).

Compound 14
Major Rotamer (65%)
$^1$H NMR (500 MHz, DMSO-$d_6$) δ ppm 12.52 (br s, 1H), 8.98 (br s, 1H), 8.80 (br d, J=3.5 Hz, 1H), 8.29 (br s, 1H), 8.06 (t, J=8.8 Hz, 1H), 7.84 (d, J=3.2 Hz, 1H), 7.71 (br s, 1H), 7.62-7.70 (m, 1H), 7.28-7.36 (m, 1H), 7.09-7.27 (m, 3H), 7.04 (br s, 1H), 6.52 (dd, J=8.8, 2.2 Hz, 1H), 6.42 (dd, J=14.7, 2.0 Hz, 1H), 5.61 (br d, J=5.0 Hz, 1H), 3.89 (br d, J=10.4 Hz, 1H), 3.43-3.58 (m, 2H), 3.28-3.40 (m, 3H), 3.21 (br quin, J=7.1 Hz, 1H), 2.93-3.11 (m, 1H), 2.70-2.87 (m, 1H), 2.12-2.27 (m, 2H), 1.54 (br s, 3H).

Minor Rotamer (35%)
$^1$H NMR (500 MHz, DMSO-$d_6$) δ ppm 12.52 (br s, 1H), 8.98 (br s, 1H), 8.80 (br d, J=3.5 Hz, 1H), 8.29 (br s, 1H), 8.06 (t, J=8.8 Hz, 1H), 7.84 (d, J=3.2 Hz, 1H), 7.71 (br s, 1H), 7.62-7.70 (m, 1H), 7.09-7.27 (m, 4H), 6.97 (br s, 1H), 6.52 (dd, J=8.8, 2.2 Hz, 1H), 6.42 (dd, J=14.7, 2.0 Hz, 1H), 5.04 (br s, 1H), 4.57 (br s, 1H), 3.43-3.58 (m, 2H), 3.28-3.40 (m, 3H), 3.21 (br quin, J=7.1 Hz, 1H), 2.93-3.11 (m 1H), 2.70-2.87 (m 1H), 2.12-2.27 (m 2H), 1.54 (br s, 3H).

Compound 15
Major Rotamer (70%)
$^1$H NMR (500 MHz, DMSO-$d_6$) δ ppm 8.91-9.03 (m, 1H), 8.80 (br d, J=3.2 Hz, 1H), 8.30 (br s, 1H), 8.06 (t, J=8.8 Hz, 1H), 7.83 (d, J=3.2 Hz, 1H), 7.71 (br s, 1H), 7.62-7.69 (m, 1H), 7.44-7.56 (m, 1H), 7.31 (br s, 1H), 7.09-7.26 (m, 3H), 7.03 (br s, 1H), 6.94-7.01 (m, 1H), 6.50 (dd, J=8.8, 2.2 Hz, 1H), 6.38 (dd, J=15.1, 1.9 Hz, 1H), 5.61 (br d, J=4.7 Hz, 1H), 3.89 (br d, J=11.0 Hz, 1H), 3.50-3.59 (m, 1H), 3.47 (br t, J=8.8 Hz, 1H), 3.35-3.41 (m, 2H), 3.25-3.32 (m, 1H), 2.96-3.12 (m, 2H), 2.70-2.88 (m, 1H), 2.14-2.24 (m, 1H), 2.02-2.14 (m, 1H), 1.54 (br s, 3H).

Minor Rotamer (30%)
$^1$H NMR (500 MHz, DMSO-$d_6$) δ ppm 8.91-9.03 (m, 1H), 8.80 (br d, J=3.2 Hz, 1H), 8.30 (br s, 1H), 8.06 (t, J=8.8 Hz, 1H), 7.83 (d, J=3.2 Hz, 1H), 7.71 (br s, 1H), 7.62-7.69 (m, 1H), 7.44-7.56 (m, 1H), 7.09-7.26 (m, 4H), 6.94-7.01 (m, 2H), 6.50 (dd, J=8.8, 2.2 Hz, 1H), 6.38 (dd, J=15.1, 1.9 Hz, 1H), 5.04 (br s, 1H), 4.57 (br s, 1H), 3.47 (br t, J=8.8 Hz, 2H), 3.35-3.41 (m, 2H), 3.25-3.32 (m, 1H), 2.96-3.12 (m, 2H), 2.70-2.88 (m, 1H), 2.14-2.24 (m, 1H), 2.02-2.14 (m, 1H), 1.54 (br s, 3H).

Compound 16
Major Rotamer (70%)
$^1$H NMR (500 MHz, DMSO-$d_6$) δ ppm 12.42 (br s, 1H), 8.10 (br t, J=7.9 Hz, 1H), 7.76 (s, 1H), 7.32 (br d, J=7.6 Hz, 1H), 7.14-7.28 (m, 5H), 6.90 (s, 1H), 5.59 (q, J=6.6 Hz, 1H), 3.65 (br dd, J=13.2, 3.2, 1H), 3.40-3.48 (m, 1H), 2.93-3.04

(m, 1H), 2.73-2.87 (m, 1H), 2.69 (br d, J=16.4 Hz, 1H), 2.53-2.55 (m, 1H), 1.94-2.00 (m, 1H), 1.50-1.55 (m, 3H), 1.44-1.50 (m, 2H), 1.15-1.27 (m, 4H).

Minor Rotamer (30%)

$^1$H NMR (500 MHz, DMSO-d$_6$) δ ppm 12.42 (br s, 1H), 8.10 (br t, J=7.9 Hz, 1H), 7.73 (s, 1H), 7.14-7.28 (m, 4H), 7.08-7.13 (m, 1H), 7.03-7.07 (m, 1H), 6.84 (s, 1H), 4.79 (q, J=6.9 Hz, 1H), 4.53-4.59 (m, 1H), 3.23-3.29 (m, 1H), 2.93-3.04 (m, 1H), 2.73-2.87 (m, 2H), 2.53-2.55 (m, 1H), 1.94-2.00 (m, 1H), 1.50-1.55 (m, 3H), 1.44-1.50 (m, 2H), 1.15-1.27 (m, 4H).

Compound 17

Major Rotamer (70%)

$^1$H NMR (500 MHz, DMSO-d$_6$) δ ppm 12.03 (br s, 1H), 8.03-8.10 (m, 1H), 7.76 (s, 1H), 7.32 (br d, J=7.6 Hz, 1H), 7.28 (d, J=8.5 Hz, 1H), 7.13-7.26 (m, 4H), 6.91 (s, 1H), 5.59 (q, J=6.5 Hz, 1H), 3.65 (br dd, J=13.6, 4.1 Hz, 1H), 3.41-3.49 (m, 1H), 2.93-3.05 (m, 1H), 2.73-2.81 (m, 1H), 2.65-2.73 (m, 2H), 2.08-2.15 (m, 1H), 1.58-1.64 (m, 1H), 1.53 (br d, J=6.9 Hz, 3H), 1.38 (td, J=8.1, 4.9 Hz, 1H), 1.16-1.27 (m, 4H).

Minor Rotamer (30%)

$^1$H NMR (500 MHz, DMSO-d$_6$) δ ppm 12.03 (br s, 1H), 8.03-8.10 (m, 1H), 7.74 (s, 1H), 7.28 (d, J=8.5 Hz, 1H), 7.13-7.26 (m, 3H), 7.04-7.13 (m, 1H), 6.85 (s, 1H), 4.79 (q, J=6.6 Hz, 1H), 4.56 (br dd, J=12.5, 4.9 Hz, 1H), 3.22-3.29 (m, 1H), 2.93-3.05 (m, 1H), 2.81-2.87 (m, 1H), 2.73-2.81 (m, 1H), 2.65-2.73 (m, 2H), 2.08-2.15 (m, 1H), 1.58-1.64 (m, 1H), 1.49 (br d, J=6.6 Hz, 3H), 1.38 (td, J=8.1, 4.9 Hz, 1H), 1.16-1.27 (m, 4H).

Compound 18

Major Rotamer (70%)

$^1$H NMR (500 MHz, DMSO-d$_6$) δ ppm 8.11 (t, J=7.9 Hz, 1H), 7.75 (s, 1H), 7.64 (br s, 1H), 7.32 (br d, J=7.3 Hz, 1H), 7.14-7.25 (m, 5H), 6.98 (br s, 1H), 6.90 (s, 1H), 5.59 (q, J=6.7 Hz, 1H), 3.64 (br dd, J=13.9, 3.5 Hz, 1H), 3.40-3.48 (m, 1H), 2.93-3.04 (m, 1H), 2.74-2.80 (m, 1H), 2.69 (br d, J=16.4 Hz, 1H), 2.31-2.35 (m, 1H), 1.94-1.99 (m, 1H), 1.53 (br d, J=6.9 Hz, 3H), 1.41 (br dt, J=9.5, 4.5 Hz, 1H), 1.32-1.37 (m, 1H), 1.15-1.27 (m, 4H).

Minor Rotamer (30%)

$^1$H NMR (500 MHz, DMSO-d$_6$) δ ppm 8.11 (t, J=7.9 Hz, 1H), 7.73 (s, 1H), 7.64 (br s, 1H), 7.14-7.25 (m, 4H), 7.08-7.13 (m, 1H), 7.03-7.07 (m, 1H), 6.98 (br s, 1H), 6.84 (s, 1H), 4.78 (q, J=6.9 Hz, 1H), 4.53-4.60 (m, 1H), 3.23-3.30 (m, 1H), 2.93-3.04 (m, 1H), 2.80-2.87 (m, 1H), 2.74-2.80 (m, 1H), 2.31-2.35 (m, 1H), 1.94-1.99 (m, 1H), 1.48 (br d, J=6.3 Hz, 3H), 1.41 (br dt, J=9.5, 4.5 Hz, 1H), 1.32-1.37 (m, 1H), 1.15-1.27 (m, 4H).

Compound 19

Major Rotamer (65%)

$^1$H NMR (500 MHz, DMSO-d$_6$) δ ppm 12.63 (br s, 1H), 8.02 (br t, J=8.7 Hz, 1H), 7.66 (s, 1H), 7.32 (br d, J=7.6 Hz, 1H), 7.21-7.25 (m, 1H), 7.14-7.21 (m, 2H), 6.81 (s, 1H), 6.54 (dd, J=8.8, 1.9 Hz, 1H), 6.46 (dd, J=14.2, 1.6 Hz, 1H), 5.58 (q, J=6.3 Hz, 1H), 3.65 (br dd, J=13.4, 3.6 Hz, 1H), 3.48-3.57 (m, 2H), 3.36-3.47 (m, 3H), 3.16-3.24 (m, 1H), 2.93-3.05 (m, 1H), 2.73-2.81 (m, 1H), 2.69 (br d, J=15.8 Hz, 1H), 2.14-2.29 (m, 2H), 1.52 (br d, J=6.6 Hz, 3H), 1.13-1.27 (m, 4H).

Minor Rotamer (35%)

$^1$H NMR (500 MHz, DMSO-d$_6$) δ ppm 12.63 (br s, 1H), 8.02 (br t, J=8.7 Hz, 1H), 7.64 (br s, 1H), 7.14-7.21 (m, 2H), 7.03-7.13 (m, 2H), 6.75 (s, 1H), 6.54 (dd, J=8.8, 1.9 Hz, 1H), 6.46 (dd, J=14.2, 1.6 Hz, 1H), 4.78 (q, J=7.3 Hz, 1H), 4.52-4.60 (m 1H), 3.48-3.57 (m 2H), 3.36-3.47 (m, 3H), 3.16-3.24 (m, 1H), 2.93-3.05 (m, 1H), 2.81-2.86 (m, 1H), 2.73-2.81 (m, 1H), 2.14-2.29 (m, 2H), 1.49 (br d, J=6.3 Hz, 3H), 1.13-1.27 (m, 4H).

Compound 20

Major Rotamer (70%)

$^1$H NMR (400 MHz, DMSO-d$_6$) δ ppm 8.01 (br t, J=8.6 Hz, 1H), 7.66 (s, 1H), 7.51 (br s, 1H), 7.32 (d, J=7.6 Hz, 1H), 7.14-7.26 (m, 3H), 7.00 (br s, 1H), 6.81 (s, 1H), 6.52 (dd, J=8.8, 1.3 Hz, 1H), 6.43 (br d, J=14.1 Hz, 1H), 5.58 (q, J=7.1 Hz, 1H), 3.65 (br d, J=13.6 Hz, 1H), 3.48-3.54 (m, 1H), 3.37-3.48 (m, 3H), 3.34-3.37 (m, 1H), 3.09 (quin, J=7.6 Hz, 1H), 2.92-3.04 (m, 1H), 2.73-2.87 (m, 1H), 2.69 (br d, J=17.7 Hz, 1H), 2.16-2.26 (m, 1H), 2.05-2.15 (m, 1H), 1.52 (br d, J=6.6 Hz, 3H), 1.19-1.27 (m, 2H), 1.08-1.18 (m, 2H).

Minor Rotamer (30%)

$^1$H NMR (400 MHz, DMSO-d$_6$) δ ppm 8.01 (br t, J=8.6 Hz, 1H), 7.63 (br s, 1H), 7.51 (br s, 1H), 7.14-7.26 (m, 2H), 7.04-7.14 (m, 2H), 7.00 (br s, 1H), 6.75 (br s, 1H), 6.52 (dd, J=8.8, 1.3 Hz, 1H), 6.43 (br d, J=14.1 Hz, 1H), 4.78 (q, J=5.6 Hz, 1H), 4.51-4.60 (m, 1H), 3.48-3.54 (m, 1H), 3.37-3.48 (m, 3H), 3.21-3.28 (m, 1H), 3.09 (quin, J=7.6 Hz, 1H), 2.92-3.04 (m, 1H), 2.73-2.87 (m, 2H), 2.16-2.26 (m, 1H), 2.05-2.15 (m, 1H), 1.49 (br d, J=6.6 Hz, 3H), 1.19-1.27 (m, 2H), 1.08-1.18 (m, 2H).

Compound 21

Major Rotamer (65%)

$^1$H NMR (500 MHz, DMSO-d$_6$) δ ppm 12.56 (br s, 1H), 8.02 (t, J=8.8 Hz, 1H), 7.75 (s, 1H), 7.30 (d, J=7.6 Hz, 1H), 7.17-7.24 (m, 2H), 7.06-7.17 (m, 1H), 7.02 (d, J=3.8 Hz, 1H), 6.55 (br d, J=8.8 Hz, 1H), 6.49 (br dd, J=14.7, 2.0 Hz, 1H), 5.50 (q, J=6.7 Hz, 1H), 3.94 (br dd, J=13.4, 4.3 Hz, 1H), 3.52-3.58 (m, 1H), 3.46-3.52 (m, 1H), 3.34-3.43 (m, 3H), 3.19-3.30 (m, 2H), 3.01-3.10 (m, 1H), 2.77 (br d, J=16.4 Hz, 1H), 2.22-2.29 (m, 1H), 2.14-2.22 (m, 1H), 1.50 (d, J=6.9 Hz, 3H), 1.20-1.38 (m, 4H).

Minor Rotamer (35%)

$^1$H NMR (500 MHz, DMSO-d$_6$) δ ppm 12.56 (br s, 1H), 8.02 (t, J=9.0 Hz, 1H), 7.67 (s, 1H), 7.17-7.24 (m, 2H), 7.06-7.17 (m, 2H), 6.98 (d, J=3.5 Hz, 1H), 6.55 (br d, J=8.8 Hz, 1H), 6.49 (br dd, J=14.7, 2.0 Hz, 1H), 5.06 (q, J=6.6 Hz, 1H), 4.50 (br dd, J=12.6, 5.0 Hz, 1H), 3.52-3.58 (m, 1H), 3.46-3.52 (m, 1H), 3.34-3.43 (m, 3H), 3.19-3.30 (m, 2H), 2.86-2.96 (m, 1H), 2.80-2.86 (m, 1H), 2.22-2.29 (m, 1H), 2.14-2.22 (m, 1H), 1.56 (d, J=6.6 Hz, 3H), 1.20-1.38 (m, 4H).

Compound 22

Major Rotamer (65%)

$^1$H NMR (400 MHz, DMSO-d$_6$) δ ppm 8.02 (t, J=8.8 Hz, 1H), 7.74 (s, 1H), 7.52 (br s, 1H), 7.30 (br d, J=6.8 Hz, 1H), 7.17-7.25 (m, 2H), 7.05-7.16 (m, 1H), 6.96-7.05 (m, 2H), 6.53 (br d, J=8.8 Hz, 1H), 6.46 (br dd, J=15.2, 1.6 Hz, 1H), 5.50 (q, J=6.4 Hz, 1H), 3.95 (br dd, J=13.9, 4.2 Hz, 1H), 3.50 (br t, J=8.7 Hz, 1H), 3.35-3.46 (m, 3H), 3.20-3.31 (m, 2H), 3.00-3.14 (m, 2H), 2.73-2.87 (m, 1H), 2.15-2.25 (m, 1H), 2.05-2.15 (m, 1H), 1.50 (d, J=6.7 Hz, 3H), 1.25-1.39 (m, 4H).

Minor Rotamer (35%)

$^1$H NMR (400 MHz, DMSO-d$_6$) δ ppm 8.02 (t, J=8.8 Hz, 1H), 7.67 (s, 1H), 7.52 (br s, 1H), 7.17-7.25 (m, 2H), 7.05-7.16 (m, 2H), 6.96-7.05 (m, 2H), 6.53 (br d, J=8.8 Hz, 1H), 6.46 (br dd, J=15.2, 1.6 Hz, 1H), 5.05 (q, J=6.9 Hz, 1H), 4.46-4.54 (m, 1H), 3.50 (br t, J=8.7 Hz, 1H), 3.35-3.46 (m, 3H), 3.20-3.31 (m, 2H), 3.00-3.14 (m, 1H), 2.73-2.87 (m, 2H), 2.15-2.25 (m, 1H), 2.05-2.15 (m, 1H), 1.56 (br d, J=6.5 Hz, 3H), 1.25-1.39 (m, 4H).

Compound 23
Major Rotamer (65%)
¹H NMR (500 MHz, DMSO-d$_6$) δ ppm 7.96-8.06 (m, 2H), 7.74 (s, 1H), 7.30 (br d, J=7.3 Hz, 1H), 7.17-7.26 (m, 2H), 7.06-7.16 (m, 1H), 7.01 (br d, J=2.8 Hz, 1H), 6.53 (br d, J=8.2 Hz, 1H), 6.45 (br d, J=15.1 Hz, 1H), 5.50 (q, J=6.3 Hz, 1H), 3.94 (br d, J=9.5 Hz, 1H), 3.51 (t, J=8.2 Hz, 1H), 3.34-3.47 (m, 3H), 3.19-3.29 (m, 2H), 3.01-3.13 (m, 2H), 2.73-2.85 (m, 1H), 2.62 (br d, J=4.4 Hz, 3H), 2.05-2.24 (m, 2H), 1.50 (br d, J=6.6 Hz, 3H), 1.21-1.39 (m, 4H).

Minor Rotamer (35%)
¹H NMR (500 MHz, DMSO-d$_6$) δ ppm 7.96-8.06 (m, 2H), 7.67 (s, 1H), 7.17-7.26 (m, 2H), 7.06-7.16 (m, 2H), 6.98 (br d, J=2.8 Hz, 1H), 6.53 (br d, J=8.2 Hz, 1H), 6.45 (br d, J=15.1 Hz, 1H), 5.06 (q, J=6.7 Hz, 1H), 4.46-4.54 (m, 1H), 3.51 (t, J=8.2 Hz, 1H), 3.34-3.47 (m, 3H), 3.19-3.29 (m, 2H), 3.01-3.13 (m, 1H), 2.73-2.85 (m, 2H), 2.62 (br d, J=4.4 Hz, 3H), 2.05-2.24 (m, 2H), 1.56 (br d, J=6.3 Hz, 3H), 1.21-1.39 (m, 4H).

Compound 24
Major Rotamer (65%)
¹H NMR (500 MHz, DMSO-d$_6$) δ ppm 12.42 (br s, 1H), 8.38-8.43 (m, 1H), 8.19 (br t, J=8.0 Hz, 1H), 7.33 (d, J=7.6 Hz, 1H), 7.15-7.26 (m, 5H), 6.98 (s, 1H), 5.60 (q, J=6.6 Hz, 1H), 3.91 (br dd, J=13.7, 3.9 Hz, 1H), 3.44-3.52 (m, 1H), 2.99-3.08 (m, 1H), 2.73 (br d, J=15.8 Hz, 1H), 2.52-2.59 (m, 2H), 1.87-2.03 (m, 2H), 1.53 (d, J=6.6 Hz, 3H), 1.38-1.50 (m, 2H), 1.02-1.17 (m. 3H).

Minor Rotamer (35%)
¹H NMR (500 MHz, DMSO-d$_6$) δ ppm 12.42 (br s, 1H), 8.38-8.43 (m, 1H), 8.19 (br t, J=8.0 Hz, 1H), 7.15-7.26 (m, 4H), 7.10-7.15 (m, 1H), 7.07 (d, J=7.3 Hz, 1H), 6.93 (s, 1H), 5.04 (q, J=6.6 Hz, 1H), 4.57 (br dd, J=12.5, 3.9 Hz, 1H), 3.23-3.30 (m, 1H), 2.83-2.97 (m, 1H), 2.52-2.59 (m, 3H), 1.87-2.03 (m, 2H), 1.59 (d, J=6.9 Hz, 3H), 1.38-1.50 (m, 2H), 1.02-1.17 (m, 3H).

Compound 25
Major Rotamer (65%)
¹H NMR (500 MHz, DMSO-d$_6$) δ ppm 7.82 (t, J=8.0 Hz, 1H), 7.32 (d, J=7.6 Hz, 1H), 7.11-7.26 (m, 5H), 6.98 (s, 1H), 5.59 (q, J=6.8 Hz, 1H), 3.91 (br dd, J=13.6, 3.8 Hz, 1H), 3.44-3.52 (m, 1H), 2.98-3.07 (m, 1H), 2.83-2.96 (m, 1H), 2.73 (br d, J=16.1 Hz, 1H), 2.57-2.63 (m, 1H), 2.39-2.47 (m, 2H), 1.88-1.94 (m, 1H), 1.53 (d, J=6.6 Hz, 3H), 1.43-1.49 (m, 1H), 1.39 (br s, 1H), 1.11-1.18 (m, 3H).

Minor Rotamer (35%)
¹H NMR (500 MHz, DMSO-d$_6$) δ ppm 7.82 (t, J=8.0 Hz, 1H), 7.11-7.26 (m, 5H), 7.04 (d, J=7.3 Hz, 1H), 6.93 (s, 1H), 5.03 (q, J=6.6 Hz, 1H), 4.55 (br dd, J=12.8, 3.9 Hz, 1H), 3.44-3.52 (m, 1H), 2.98-3.07 (m, 1H), 2.83-2.96 (m, 1H), 2.57-2.63 (m, 1H), 2.39-2.47 (m, 3H), 1.88-1.94 (m, 1H), 1.58 (d, J=6.6 Hz, 3H), 1.43-1.49 (m, 1H), 1.39 (br s, 1H), 1.11-1.18 (m, 3H).

Compound 26
Major Rotamer (65%)
¹H NMR (500 MHz, DMSO-d$_6$) δ ppm 7.53-7.61 (m, 1H), 7.32 (d, J=7.3 Hz, 1H), 7.05-7.26 (m, 6H), 5.54-5.63 (m, 1H), 3.84-3.93 (m, 1H), 3.44-3.54 (m, 1H), 2.97-3.08 (m, 1H), 2.82-2.97 (m, 1H), 2.73 (br dd, J=16.2, 2.4 Hz, 1H), 2.39-2.46 (m, 2H partially obscured by DMSO peak), 1.92 (br s, 1H), 1.67-1.76 (m, 1H), 1.53 (d, J=6.9 Hz, 3H), 1.43-1.49 (m, 1H), 1.34-1.41 (m, 1H), 0.83-1.06 (m, 3H).

Minor Rotamer (35%)
¹H NMR (500 MHz, DMSO-d$_6$) δ ppm 7.53-7.61 (m, 1H), 7.05-7.26 (m, 7H), 5.04 (quin, J=7.0 Hz, 1H), 4.52-4.58 (m, 1H), 3.44-3.54 (m, 1H), 2.97-3.08 (m, 1H), 2.82-2.97 (m, 1H), 2.39-2.46 (m, 3H partially obscured by DMSO peak), 1.92 (br s, 1H), 1.67-1.76 (m, 1H), 1.59 (dd, J=10.9, 6.8 Hz, 3H), 1.43-1.49 (m, 1H), 1.34-1.41 (m, 1H), 0.83-1.06 (m, 3H).

Compound 27
Major Rotamer (65%)
¹H NMR (500 MHz, DMSO-d$_6$) δ ppm 12.55 (br s, 1H), 8.19-8.24 (m, 1H), 8.09 (t, J=9.0 Hz, 1H), 7.32 (d, J=7.6 Hz, 1H), 7.15-7.26 (m 3H), 6.93 (s, 1H), 6.55 (dt, J=8.8, 2.7 Hz, 1H), 6.49 (dd, J=14.8, 1.6 Hz, 1H), 5.60 (q, J=6.6 Hz, 1H), 3.93 (br dd, J=13.7, 3.9 Hz, 1H), 3.43-3.57 (m, 3H), 3.34-3.43 (m, 2H), 3.20-3.26 (m, 1H), 3.01-3.10 (m, 1H), 2.74 (br d, J=15.8 Hz, 1H), 2.14-2.29 (m, 2H), 1.53 (d, J=6.9 Hz, 3H), 1.19-1.26 (m, 2H), 1.02-1.13 (m, 2H).

Minor Rotamer (35%)
¹H NMR (500 MHz, DMSO-d$_6$) δ ppm 12.55 (br s, 1H), 8.19-8.24 (m, 1H), 8.09 (t, J=9.0 Hz, 1H), 7.15-7.26 (m, 2H), 7.10-7.15 (m, 1H), 7.08 (d, J=7.6 Hz, 1H), 6.89 (s, 1H), 6.55 (dt, J=8.8, 2.7 Hz, 1H), 6.49 (dd, J=14.8, 1.6 Hz, 1H), 5.07 (q, J=6.6 Hz, 1H), 4.57 (br dd, J=12.3, 4.4 Hz, 1H), 3.43-3.57 (m, 2H), 3.34-3.43 (m, 2H), 3.26-3.31 (m, 1H), 3.20-3.26 (m, 1H), 2.83-2.97 (m, 2H), 2.14-2.29 (m, 2H), 1.59 (d, J=6.6 Hz, 3H), 1.19-1.26 (m, 2H), 1.02-1.13 (m, 2H).

Compound 28
Major Rotamer (65%)
¹H NMR (400 MHz, DMSO-d$_6$) δ ppm 8.20 (br s, 1H), 8.08 (br t, J=8.8 Hz, 1H), 7.50 (br s, 1H), 7.32 (d, J=7.1 Hz, 1H), 7.05-7.27 (m, 3H), 7.00 (br s, 1H), 6.93 (s, 1H), 6.53 (br d, J=9.1 Hz, 1H), 6.46 (br d, J=14.7 Hz, 1H), 5.60 (q, J=6.4 Hz, 1H), 3.93 (br dd, J=13.9, 4.3 Hz, 1H), 3.34-3.55 (m, 4H), 3.22-3.30 (m, 1H partially obscured by H2O peak), 3.02-3.13 (m, 2H), 2.73 (br d, J=16.7 Hz, 1H), 2.15-2.25 (m, 1H), 2.04-2.15 (m, 1H), 1.53 (d, J=7.1 Hz, 3H), 1.17-1.29 (m, 2H), 0.98-1.14 (m, 2H).

Minor Rotamer (35%)
¹H NMR (400 MHz, DMSO-d$_6$) δ ppm 8.20 (br s, 1H), 8.08 (br t, J=8.8 Hz, 1H), 7.50 (br s, 1H), 7.05-7.27 (m, 4H), 7.00 (br s, 1H), 6.88 (s, 1H), 6.53 (br d, J=9.1 Hz, 1H), 6.46 (br d, J=14.7 Hz, 1H), 5.06 (q, J=6.6 Hz, 1H), 4.53-4.62 (m, 1H), 3.34-3.55 (m, 4H), 3.22-3.30 (m, 1H partially obscured by H$_2$O peak), 3.02-3.13 (m, 1H), 2.82-2.97 (m, 2H), 2.15-2.25 (m, 1H), 2.04-2.15 (m, 1H), 1.59 (d, J=6.6 Hz, 3H), 1.17-1.29 (m, 2H), 0.98-1.14 (m, 2H).

LC-MS Data
General Procedure
The High Performance Liquid Chromatography (HPLC) measurement was performed using a LC pump, a diode-array (DAD) or a UV detector and a column as specified in the respective methods. If necessary, additional detectors were included (see table of methods below). Flow from the column was brought to the Mass Spectrometer (MS) which was configured with an atmospheric pressure ion source. It is within the knowledge of the skilled person to set the tune parameters (e.g. scanning range, dwell time . . . ) in order to obtain ions allowing the identification of the compound's nominal monoisotopic molecular weight (MW). Data acquisition was performed with appropriate software.

Compounds are described by their experimental retention times (Rt) and ions. If not specified differently in the table of data, the reported molecular ion corresponds to the [M+H]⁺ (protonated molecule) and/or [M−H]⁻ (deprotonated molecule). Incase the compound was not directly ionizable the type of adduct is specified (i.e. [M+NH$_4$]⁺, [M+HCOO]³¹, etc. . . . ). For molecules with multiple isotopic patterns (Br, CL), the reported value is the one obtained for the lowest isotope mass. All results were obtained with experimental uncertainties that are commonly associated with the method used.

Hereinafter, "SQD" means Single Quadrupole Detector, "RT" room temperature, "BEH" bridged ethylsiloxane/silica hybrid, "HSS" High Strength Silica, "DAD" Diode Array Detector.

TABLE

LCMS Method codes (Flow expressed in mL/min; column temperature (T) in °C.; Run time in minutes).

| Method code | Instrument | Column | Mobile phase | gradient | Flow Column T | Run time |
|---|---|---|---|---|---|---|
| A | Waters: Acquity UPLC ® - DAD and Quattro Micro ™ | Waters: BEH C18 (1.7 μm, 2.1 × 100 mm) | A: 95% $CH_3COONH_4$ 7 mM/5% $CH_3CN$, B: $CH_3CN$ | 84.2% A for 0.49 min, to 10.5% A in 2.18 min, held for 1.94 min, back to 84.2% A in 0.73 min, held for 0.73 min. | 0.343 40 | 6.2 |
| B | Waters: Acquity ® H-Class - DAD and SQD2 ™ | Waters: BEH C18 (1.7 μm, 2.1 × 100 mm) | A: 95% $CH_3COONH_4$ 7 mM/5% $CH_3CN$, B: $CH_3CN$ | 84.2% A to 10.5% A in 2.18 min, held for 1.96 min, back to 84.2% A in 0.73 min, held for 0.73 min. | 0.343 40 | 6.1 |
| C | Waters: Acquity UPLC ® H-Class - DAD and SQD2 ™ | Waters BEH ® C18 (1.7 μm, 2.1 × 50 mm) | A: 95% $CH_3COONH_4$ 7 mM/5% $CH_3CN$, B: $CH_3CN$ | From 95% A to 5% A in 1 min, held for 1.6 min, back to 95% A in 0.2 min, held for 0.5 min. | 0.5 40 | 3.3 |

| Co. No. | Rt | MW (theor) | BPM1 [M + H]+ | LC/GC/MS Method |
|---|---|---|---|---|
| 1 | 2.68 | 496.2 | 497.2 | A |
| 2 | 3.19 | 495.2 | 496.3 | A |
| 3 | 2.71 | 525.2 | 526.3 | A |
| 4 | 2.61 | 497.2 | 498.3 | A |
| 5 | 2.52 | 527.2 | 528.6 | B |
| 6 | 2.69 | 527.2 | 528.3 | A |
| 7 | 2.66 | 526.2 | 527.3 | A |
| 8 | 3.2 | 525.3 | 526.3 | A |
| 9 | 2.7 | 540.3 | 541.4 | A |
| 10 | 3.27 | 555 | 556.3 | A |
| 11 | 1.19 | 509.2 | 510.4 | C |
| 12 | 2.98 | 508.2 | 509.3 | A |
| 13 | 2.94 | 537.2 | 538.4 | A |
| 14 | 2.21 | 575.2 | 576.4 | A |
| 15 | 2.56 | 574.2 | 575.5 | A |
| 16 | 2.37 | 510.2 | 511.3 | A |
| 17 | 2.37 | 510.2 | 511.3 | A |
| 18 | 2.83 | 509.2 | 510.3 | A |
| 19 | 2.4 | 539.2 | 540.3 | A |
| 20 | 2.73 | 538.2 | 539.5 | B |
| 21 | 2.69 | 539.2 | 540.4 | A |
| 22 | 3.21 | 538.2 | 539.4 | A |
| 23 | 3.33 | 552.2 | 553.5 | A |
| 24 | 2.34 | 510.2 | 511.2 | A |
| 25 | 2.37 | 528.2 | 529.3 | A |
| 26 | 2.31 | 528.2 | 529.4 | A |
| 27 | 2.39 | 539.2 | 540.3 | A |
| 28 | 2.81 | 538.2 | 539.3 | A |

Optical Rotation

The optical rotation was measured using a polarimeter with light at the wavelength of the D-line of sodium (589 nm) at a temperature of 20° C. in DMF as solvent.

| Co. No. | $[\alpha]_D^{20}$ | c (w/v %) |
|---|---|---|
| 1 | +109.29° | 0.28 |
| 2 | +129.07° | 0.258 |
| 3 | +7.69° | 0.234 |
| 8 | −30.77° | 0.26 |
| 9 | −24.07° | 0.27 |
| 10 | −56.43° | 0.28 |
| 14 | +14.16° | 0.219 |
| 15 | −29.28° | 0.222 |
| 19 | +4.44° | 0.27 |
| 20 | −29.74° | 0.252 |
| 21 | +37.88° | 0.264 |
| 22 | +4.96° | 0.262 |
| 23 | −6.08° | 0.296 |

-continued

| Co. No. | $[\alpha]_D^{20}$ | c (w/v %) |
|---|---|---|
| 27 | +42.19° | 0.32 |
| 28 | −10° | 0.25 |

E. Pharmacological Examples

E.1 Antiviral Activity

Black 384-well clear-bottom microtiter plates (Corning, Amsterdam, The Netherlands) were filled via acoustic drop ejection using the echo liquid handler (Labcyte, Sunnyvale, Calif.). 200 nL of compound stock solutions (100% DMSO) were transferred to the assay plates. 9 serial 4-fold dilutions of compound were made, creating per quadrant the same compound concentration. The assay was initiated by adding 10 μL of culture medium to each well (RPMI medium without phenol red, 10% FBS-heat inactivated, 0.04% gentamycin (50 mg/mL). All addition steps are done by using a multidrop dispenser (Thermo Scientific, Erembodegem, Belgium). Next, rgRSV224 virus (MOI=1) diluted in culture medium was added to the plates. rgRSV224 virus is an engineered virus that includes an additional GFP gene (Hallak L K, Spillmann D, Collins P L, Peeples M E. Glycosaminoglycan sulfation requirements for respiratory syncytial virus infection; Journal of virology (2000), 74(22), 10508-13) and was in-licensed from the NIH (Bethesda, Md., USA). Finally, 20 μL of a HeLa cell suspension (3,000 cells/well) were plated. Medium, virus- and mock-infected controls were included in each test. The wells contain 0.05% DMSO per volume. Cells were incubated at 37° C. in a 5% CO2 atmosphere. Three days post-virus exposure, viral replication was quantified by measuring GFP expression in the cells by an in house developed MSM laser microscope (Tibotec, Beerse, Belgium). The $EC_{50}$ was defined as the 50% inhibitory concentration for GFP expression. In parallel, compounds were incubated for three days in a set of white 384-well microtiter plates (Corning) and the cytotoxicity of compounds in HeLa cells was determined by measuring the ATP content of the cells using the ATPlite kit (Perkin Elmer, Zaventem, Belgium) according to the manufacturer's instructions. The $CC_{50}$ was defined as the 50% concentration for cytotoxicity.

TABLE antiviral data (averaged data of several repeat experiments)

| Co. No. | RSV HELA $EC_{50}$ (μM) | TOX HELA $CC_{50}$ (μM) |
| --- | --- | --- |
| 1 | 0.195 | 45.10 |
| 2 | 0.344 | 52.70 |
| 3 | 0.218 | 44.00 |
| 4 | 0.219 | 57.60 |
| 5 | 1.700 | 47.20 |
| 6 | 0.090 | 50.20 |
| 7 | 0.064 | 48.00 |
| 8 | 0.054 | 53.40 |
| 9 | 0.596 | 50.60 |
| 10 | 0.062 | 40.40 |
| 11 | 0.197 | 39.90 |
| 12 | 0.203 | 59.00 |
| 13 | 0.294 | 23.40 |
| 14 | 1.150 | 52.80 |
| 15 | 0.480 | 20.60 |
| 16 | 0.182 | 79.40 |
| 17 | 2.010 | >100 |
| 18 | 0.178 | 47.90 |
| 19 | 0.100 | 60.90 |
| 20 | 0.102 | 45.60 |
| 21 | 0.564 | 29.80 |
| 22 | 0.870 | >100 |
| 23 | 0.882 | >100 |
| 24 | 0.105 | 69.70 |
| 25 | 0.112 | 22.30 |
| 26 | 3.420 | 77.20 |
| 27 | 0.159 | 40.40 |
| 28 | 0.112 | 22.30 |

F. Prophetic Composition Examples

"Active ingredient" as used throughout these examples relates to a final compound of Formula (I), the pharmaceutically acceptable salts thereof, the solvates and the stereochemically isomeric forms and the tautomers thereof.

Typical examples of recipes for the formulation of the invention are as follows:

F.1. Tablets

| Active ingredient | 5 to 50 mg |
| --- | --- |
| Di calcium phosphate | 20 mg |

-continued

| Lactose | 30 mg |
| --- | --- |
| Talcum | 10 mg |
| Magnesium stearate | 5 mg |
| Potato starch | ad 200 mg |

In this Example, active ingredient can be replaced with the same amount of any of the compounds according to the present invention, in particular by the same amount of any of the exemplified compounds.

F.2. Suspension

An aqueous suspension is prepared for oral administration so that each 1 milliliter contains 1 to 5 mg of one of the active compounds, 50 mg of sodium carboxymethyl cellulose, 1 mg of sodium benzoate, 500 mg of sorbitol and water ad 1 ml.

F.3. Injectable

A parenteral composition is prepared by stirring 1.5% by weight of active ingredient of the invention in 10% by volume propylene glycol in water.

F.4. Ointment

| Active ingredient | 5 to 1000 mg |
| --- | --- |
| Stearyl alcohol | 3 g |
| Lanoline | 5 g |
| White petroleum | 15 g |
| Water | ad 100 g |

In this Example, active ingredient can be replaced with the same amount of any of the compounds according to the present invention, in particular by the same amount of any of the exemplified compounds.

The invention claimed is:

1. A compound of formula (I):

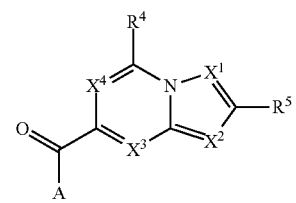

or a pharmaceutically acceptable acid addition salt or stereochemically isomeric form thereof, wherein:

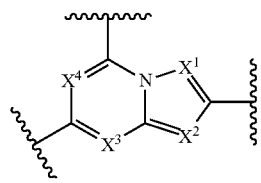

is formula (a), formula (b), formula (c), formula (d), formula (e), or formula (f):

(a)

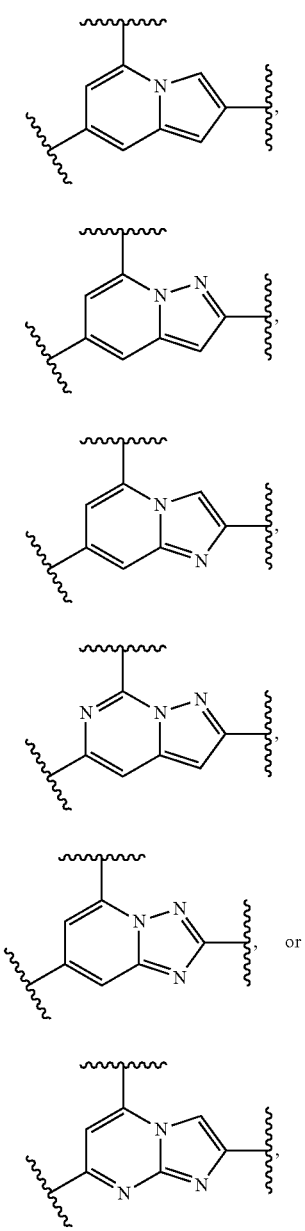

wherein each CH is optionally substituted with halo, $C_{1-4}$ alkyl, or $OC_{1-4}$ alkyl;

A is formula (a-1), formula (a-2), formula (a-3), or formula (a-4):

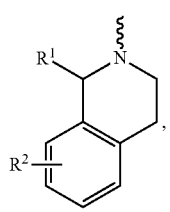

(a-1)

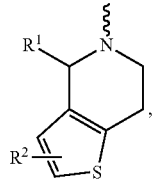

(a-2)

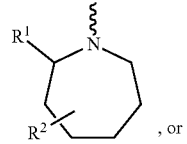

(a-3)

, or

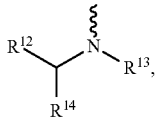

(a-4)

wherein:
$R^1$ is $CH_3$ or $CH_2CH_3$;
$R^2$ is H, halo, or $C_{1-4}$ alkyl;
$R^{12}$ is $C_{1-2}$ alkyl;
$R^{13}$ is $C_{1-6}$ alkyl; and
$R^{14}$ is $C_{1-6}$ alkyl;
$R^4$ is $C_{1-6}$ alkyl, $C_{1-4}$ alkylene-Heteroaryl$^1$, N($C_{1-6}$ alkyl)$_2$, $C_{3-6}$ cycloalkyl, pyrrolidinyl, phenyl, or Heteroaryl$^1$;
  wherein the phenyl is optionally substituted with one, two, or three substituents independently selected from the group consisting of halo, CN, $C_{1-4}$ alkyl, $C_{1-4}$ polyhaloalkyl, OH, and $OC_{1-4}$ alkyl, and
  wherein the Heteroaryl$^1$ is thienyl, pyridinyl, or pyrimidinyl, wherein the thienyl, pyridinyl, or pyrimidinyl is optionally substituted with one or two substituents independently selected from the group consisting of halo, $C_{1-4}$ alkyl, C(O)NH$_2$, and NH$_2$;
$R^5$ is formula (b-1), formula (b-2), or formula (b-3):

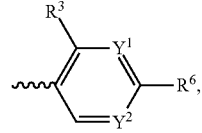

(b-1)

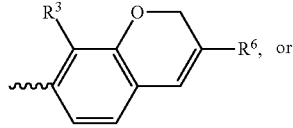

(b-2)

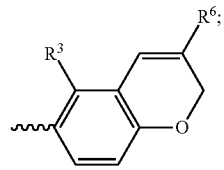

(b-3)

wherein:
$Y^1$ is CH, CF, or N;
$Y^2$ is CH, CF, or N;
$R^3$ is halo; and
$R^6$ is (i), (ii), (iii), or (iv):
(i) $C_{2-6}$ alkenyl, wherein the $C_{2-6}$ alkenyl is substituted with one or two substituents independently selected from the group consisting of $C_{1-6}$ alkyl, C(O)NR$^8$R$^9$, and C(O)OR$^7$;

(ii) NR⁹C(O)-Heterocyclyl;
    wherein the Heterocyclyl is azetidinyl, pyrrolidinyl, piperidinyl, or homopiperidinyl; and
    wherein the azetidinyl, pyrrolidinyl, piperidinyl, or homopiperidinyl is substituted with one or two substituents independently selected from the group consisting of halo, OH, and OC$_{1-4}$ alkyl; or
(iii) C$_{3-6}$ cycloalkyl, wherein the C$_{3-6}$ cycloalkyl is substituted with one or two substituents independently selected from the group consisting of:
    (a) C$_{1-6}$ alkyl;
        wherein the C$_{1-6}$ alkyl is optionally substituted with one, two, or three substituents independently selected from the group consisting of halo, C(O)NH$_2$, C(O)OH, OH, and C$_{3-6}$ cycloalkyl;
        wherein the C$_{3-6}$ cycloalkyl substituent is optionally substituted with one or two substituents independently selected from the group consisting of halo, C$_{1-4}$ alkyl, C$_{1-4}$ alkylene-C(O)OH, and C(O)OH;
    (b) C$_{3-6}$ alkenyl, wherein the C$_{3-6}$ alkenyl is optionally substituted with one or two substituents independently selected from the group consisting of C$_{1-6}$ alkyl, C(O)NR⁸R⁹, C(O)OR⁷, and OH; and
    (c) CN, C(O)NR¹⁰R¹¹, C(O)NR⁹C(O)S(O)$_2$R⁸, C(O)NR⁹S(O)$_2$R⁸, C(O)OR⁷, NR⁸R⁹, NR⁹C(O)C$_{1-4}$ alkyl, NR⁹C(O)NR⁸R⁹, NR⁹C(O)OR⁸, NR⁹C(O)C$_{3-6}$ cycloalkyl, NR⁹S(O)$_2$R⁸, OH, OC(O)NR¹⁰R¹¹, S(O)$_2$R⁸, S(O)$_2$NR¹⁰R¹¹, S(O)$_2$NR⁹C(O)R⁸, or Heteroaryl²;
        wherein each Heteroaryl² is independently pyrrolyl, pyrazolyl, or thiazolyl;
        wherein each pyrrolyl, pyrazolyl, or thiazolyl is optionally and independently substituted with one or two substituents independently selected from the group consisting of halo, C$_{1-4}$ alkyl, C(O)NR⁸R⁹, and C(O)OR⁷; or
(iv) Heterocyclyl;
    wherein the Heterocyclyl is azetidinyl, pyrrolidinyl, piperidinyl, or homopiperidinyl; and
    wherein the azetidinyl, pyrrolidinyl, piperidinyl, or homopiperidinyl is substituted with one or two substituents independently selected from the group consisting of:
    (a) C$_{1-6}$ alkyl;
        wherein the C$_{1-6}$ alkyl is optionally substituted with one, two, or three substituents independently selected from the group consisting of halo, C(O)NH$_2$, C(O)OH, OH, and C$_{3-6}$ cycloalkyl; and
        wherein the C$_{3-6}$ cycloalkyl substituent is optionally substituted with one or two substituents independently selected from the group consisting of halo, C$_{1-4}$ alkyl, C$_{1-4}$ alkylene-C(O)OH, and C(O)OH;
    (b) C$_{3-6}$ alkenyl, wherein the C$_{3-6}$ alkenyl is optionally substituted with one or two substituents independently selected from the group consisting of C$_{1-6}$ alkyl, C(O)NR⁸R⁹, C(O)OR⁷, and OH; and
    (c) CN, C(O)NR¹⁰R¹¹, C(O)NR⁹C(O)S(O)$_2$R⁸, C(O)NR⁹S(O)$_2$R⁸, C(O)OR⁷, NR⁸R⁹, NR⁹C(O)C$_{1-4}$ alkyl, NR⁹C(O)NR⁸R⁹, NR⁹C(O)OR⁸, NR⁹C(O)C$_{3-6}$ cycloalkyl, NR⁹S(O)$_2$R⁸, OH, OC(O)NR¹⁰R¹¹, S(O)$_2$R⁸, S(O)$_2$NR¹⁰R¹¹, S(O)$_2$NR⁹C(O)R⁸, or Heteroaryl²;
        wherein each Heteroaryl² is independently pyrrolyl, pyrazolyl, or thiazolyl;
        wherein each pyrrolyl, pyrazolyl, or thiazolyl is optionally and independently substituted with one or two substituents independently selected from the group consisting of halo, C$_{1-4}$ alkyl, C(O)NR⁸R⁹, and C(O)OR⁷;

each R⁷ is independently H or C$_{1-4}$ alkyl;
each R⁸ is independently C$_{1-4}$ alkyl, C$_{1-4}$ polyhaloalkyl, or C$_{3-6}$ cycloalkyl;
each R⁹ is independently H or C$_{1-4}$ alkyl;
each R¹⁰ is independently H, CN, C$_{1-4}$ alkyl, C$_{1-4}$ polyhaloalkyl, C$_{3-6}$ alkenyl, or C$_{3-6}$ cycloalkyl;
    wherein each C$_{1-4}$ alkyl is optionally and independently substituted with one substituent selected from the group consisting of CN and OH; and
    wherein each C$_{3-6}$ cycloalkyl is optionally and independently substituted with one C$_{1-4}$ alkyl substituent; and
each R¹¹ is independently H, CN, C$_{1-4}$ alkyl, C$_{1-4}$ polyhaloalkyl, C$_{3-6}$ alkenyl, or C$_{3-6}$ cycloalkyl;
    wherein each C$_{1-4}$ alkyl is optionally and independently substituted with one substituent selected from the group consisting of CN and OH; and
    wherein each C$_{3-6}$ cycloalkyl is optionally and independently substituted with one C$_{1-4}$ alkyl substituent.

2. The compound of claim 1, or a pharmaceutically acceptable acid addition salt or stereochemically isomeric form thereof, wherein

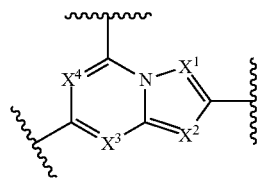

is formula (c):

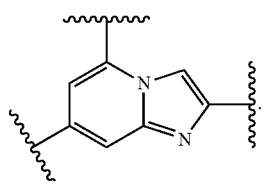

(c)

3. The compound of claim 1, or a pharmaceutically acceptable acid addition salt or stereochemically isomeric form thereof, wherein

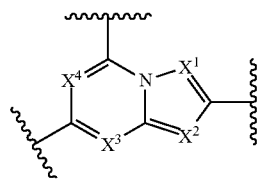

is formula (e):

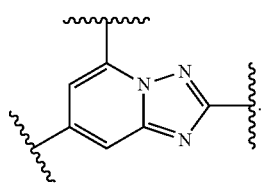

(e)

4. The compound of claim 1, or a pharmaceutically acceptable acid addition salt or stereochemically isomeric form thereof, wherein A is formula (a-1):

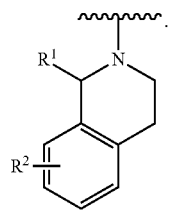

(a-1)

5. The compound of claim 1, or a pharmaceutically acceptable acid addition salt or stereochemically isomeric form thereof, wherein A is formula (a-2):

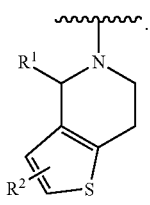

(a-2)

6. The compound of claim 1, or a pharmaceutically acceptable acid addition salt or stereochemically isomeric form thereof, wherein $R^1$ is $CH_3$.

7. The compound of claim 1, or a pharmaceutically acceptable acid addition salt or stereochemically isomeric form thereof, wherein $R^2$ is H.

8. The compound of claim 1, or a pharmaceutically acceptable acid addition salt or stereochemically isomeric form thereof, wherein $R^4$ is $C_{1-4}$ alkyl.

9. The compound of claim 1, or a pharmaceutically acceptable acid addition salt or stereochemically isomeric form thereof, wherein $R^4$ is $CH_2CH_3$.

10. The compound of claim 1, or a pharmaceutically acceptable acid addition salt or stereochemically isomeric form thereof, wherein $R^4$ is $C_{3-6}$ cycloalkyl.

11. The compound of claim 1, or a pharmaceutically acceptable acid addition salt or stereochemically isomeric form thereof, wherein $R^4$ is cyclopropyl.

12. The compound of claim 1, or a pharmaceutically acceptable acid addition salt or stereochemically isomeric form thereof, wherein $R^4$ is Heteroaryl$^1$.

13. The compound of claim 1, or a pharmaceutically acceptable acid addition salt or stereochemically isomeric form thereof, wherein $R^4$ is pyridinyl.

14. The compound of claim 1, or a pharmaceutically acceptable acid addition salt or stereochemically isomeric form thereof, wherein $R^5$ is formula (b-1):

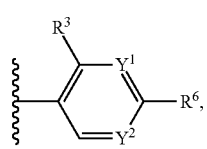

(b-1)

wherein:
$Y^1$ is CH; and
$Y^2$ is CH.

15. The compound of claim 14, or a pharmaceutically acceptable acid addition salt or stereochemically isomeric form thereof, wherein $R^3$ is F.

16. The compound of claim 1, or a pharmaceutically acceptable acid addition salt or stereochemically isomeric form thereof, wherein $R^6$ is $C_{3-6}$ cycloalkyl or pyrrolidinyl, wherein the $C_{3-6}$ cycloalkyl or pyrrolidinyl is substituted with one or two substituents independently selected from the group consisting of $C(O)NR^{10}R^{11}$ and $C(O)OR^7$.

17. The compound of claim 1, wherein the compound is selected from the group consisting of:
(1S,2S)-2-(4-{5-Ethyl-7-[(1R)-1-methyl-1,2,3,4-tetrahydroisoquinoline-2-carbonyl]indolizin-2-yl}-3-fluorophenyl)cyclopropane-1-carboxylic acid;
(1S,2S)-2-(4-{5-Ethyl-7-[(1R)-1-methyl-1,2,3,4-tetrahydroisoquinoline-2-carbonyl]-7,8-dihydroindolizin-2-yl}-3-fluorophenyl)cyclopropane-1-carboxamide;
(3S)-1-(4-{5-Ethyl-7-[(1R)-1-methyl-1,2,3,4-tetrahydroisoquinoline-2-carbonyl]indolizin-2-yl}-3-fluorophenyl)pyrrolidine-3-carboxylic acid;
trans-2-(4-{7-ethyl-5-[(1R)-1-methyl-1,2,3,4-tetrahydroisoquinoline-2-carbonyl]pyrazolo[1,5-a]pyridin-2-yl}-3-fluorophenyl)cyclopropane-1-carboxylic acid;
trans-2-(4-{7-Ethyl-4-methoxy-5-[(1R)-1-methyl-1,2,3,4-tetrahydroisoquinoline-2-carbonyl]pyrazolo[1,5-a]pyridin-2-yl}-3-fluorophenyl)cyclopropane-1-carboxylic acid;
trans-2-(4-{7-Cyclopropyl-4-fluoro-5-[(1R)-1-methyl-1,2,3,4-tetrahydroisoquinoline-2-carbonyl]pyrazolo[1,5-a]pyridin-2-yl}-3-fluorophenyl)cyclopropane-1-carboxylic acid;
(3S)-1-(4-{7-Cyclopropyl-5-[(1R)-1-methyl-1,2,3,4-tetrahydroisoquinoline-2-carbonyl]pyrazolo[1,5-a]pyridin-2-yl}-3-fluorophenyl)pyrrolidine-3-carboxylic acid;
(3S)-1-(4-{7-Cyclopropyl-5-[(1R)-1-methyl-1,2,3,4-tetrahydroisoquinoline-2-carbonyl]pyrazolo[1,5-a]pyridin-2-yl}-3-fluorophenyl)pyrrolidine-3-carboxamide;
(3S)-1-(4-{7-Ethyl-4-methyl-5-[(1R)-1-methyl-1,2,3,4-tetrahydroisoquinoline-2-carbonyl]pyrazolo[1,5-a]pyridin-2-yl}-3-fluorophenyl)pyrrolidine-3-carboxylic acid;
(3S)-1-(4-{7-Cyclopropyl-4-fluoro-5-[(1R)-1-methyl-1,2,3,4-tetrahydroisoquinoline-2-carbonyl]pyrazolo[1,5-a]pyridin-2-yl}-3-fluorophenyl)pyrrolidine-3-carboxamide;
trans-2-(4-{5-Cyclopropyl-7-[(1R)-1-methyl-1,2,3,4-tetrahydroisoquinoline-2-carbonyl]-[1,2,4]triazolo[1,5-a]pyridin-2-yl}-3-fluorophenyl)cyclopropane-1-carboxylic acid;
cis-2-(4-{5-Cyclopropyl-7-[(1R)-1-methyl-1,2,3,4-tetrahydroisoquinoline-2-carbonyl]-[1,2,4]triazolo[1,5-a]pyridin-2-yl}-3-fluorophenyl)cyclopropane-1-carboxylic acid;
trans-2-(4-{5-Cyclopropyl-7-[(1R)-1-methyl-1,2,3,4-tetrahydroisoquinoline-2-carbonyl]-[1,2,4]triazolo[1,5-a]pyridin-2-yl}-3-fluorophenyl)cyclopropane-1-carboxamide;
(3S)-1-(4-{5-Cyclopropyl-7-[(1R)-1-methyl-1,2,3,4-tetrahydroisoquinoline-2-carbonyl]-[1,2,4]triazolo[1,5-a]pyridin-2-yl}-3-fluorophenyl)pyrrolidine-3-carboxylic acid;
(3S)-1-(4-{5-Cyclopropyl-7-[(1R)-1-methyl-1,2,3,4-tetrahydroisoquinoline-2-carbonyl]-[1,2,4]triazolo[1,5-a]pyridin-2-yl}-3-fluorophenyl)pyrrolidine-3-carboxamide;

(3S)-1-(4-{7-Cyclopropyl-5-[(1R)-1-methyl-1,2,3,4-tetrahydroisoquinoline-2-carbonyl]pyrazolo[1,5-c]pyrimidin-2-yl}-3-fluorophenyl)pyrrolidine-3-carboxylic acid;

(3S)-1-(4-{7-Cyclopropyl-5-[(1R)-1-methyl-1,2,3,4-tetrahydroisoquinoline-2-carbonyl]pyrazolo[1,5-c]pyrimidin-2-yl}-3-fluorophenyl)pyrrolidine-3-carboxamide;

(3S)-1-(4-{7-Cyclopropyl-5-[(1R)-1-methyl-1,2,3,4-tetrahydroisoquinoline-2-carbonyl]pyrazolo[1,5-c]pyrimidin-2-yl}-3-fluorophenyl)-N-methylpyrrolidine-3-carboxamide;

trans-2-(4-{5-Cyclopropyl-7-[(1R)-1-methyl-1,2,3,4-tetrahydroisoquinoline-2-carbonyl] imidazo[1,2-a]pyrimidin-2-yl}-3-fluorophenyl)cyclopropane-1-carboxylic acid;

trans-2-(4-{5-cyclopropyl-3-fluoro-7-[(1R)-1-methyl-1,2,3,4-tetrahydroisoquinoline-2-carbonyl] imidazo[1,2-a]pyrimidin-2-yl}-3-fluorophenyl)cyclopropane-1-carboxylic acid;

cis-2-(4-{5-cyclopropyl-3-fluoro-7-[(1R)-1-methyl-1,2,3,4-tetrahydroisoquinoline-2-carbonyl] imidazo[1,2-a]pyrimidin-2-yl}-3-fluorophenyl)cyclopropane-1-carboxylic acid;

(3S)-1-(4-{5-Cyclopropyl-7-[(1R)-1-methyl-1,2,3,4-tetrahydroisoquinoline-2-carbonyl] imidazo[1,2-a]pyrimidin-2-yl}-3-fluorophenyl)pyrrolidine-3-carboxylic acid; and (3S)-1-(4-{5-Cyclopropyl-7-[(1R)-1-methyl-1,2,3,4-tetrahydroisoquinoline-2-carbonyl] imidazo[1,2-a]pyrimidin-2-yl}-3-fluorophenyl)pyrrolidine-3-carboxamide;

or a pharmaceutically acceptable acid addition salt thereof.

18. A pharmaceutical composition comprising a pharmaceutically acceptable carrier and a therapeutically effective amount of the compound of claim 1, or a pharmaceutically acceptable acid addition salt or stereochemically isomeric form thereof.

19. A method for treating a respiratory syncytial virus infection in a subject in need thereof, wherein the method comprises administering to the subject a therapeutically effective amount of the compound of claim 1, or a pharmaceutically acceptable acid addition salt or stereochemically isomeric form thereof.

20. A process for preparing the pharmaceutical composition of claim 18, wherein the process comprises intimately mixing a pharmaceutically acceptable carrier with a therapeutically effective amount of the compound of claim 1, or a pharmaceutically acceptable acid addition salt or stereochemically isomeric form thereof.

* * * * *